(12) United States Patent
Bolli et al.

(10) Patent No.: US 7,723,378 B2
(45) Date of Patent: May 25, 2010

(54) HYDROGENATED BENZO (C) THIOPHENE DERIVATIVES AS IMMUNOMODULATORS

(75) Inventors: Martin Bolli, Allschwil (CH); David Lehmann, Basel (CH); Boris Mathys, Egerkingen (CH); Claus Mueller, Weil Am Rhein (DE); Oliver Nayler, Arlesheim (CH); Jörg Velker, Huningue (FR); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 117 days.

(21) Appl. No.: 11/909,429

(22) PCT Filed: Mar. 20, 2006

(86) PCT No.: PCT/IB2006/050845

§ 371 (c)(1),
(2), (4) Date: Sep. 21, 2007

(87) PCT Pub. No.: WO2006/100631

PCT Pub. Date: Sep. 28, 2006

(65) Prior Publication Data

US 2008/0176926 A1 Jul. 24, 2008

(30) Foreign Application Priority Data

Mar. 23, 2005 (WO) ............... PCT/EP2005/003071

(51) Int. Cl.
*A61K 31/38* (2006.01)
(52) U.S. Cl. .................... 514/443; 514/444; 549/49
(58) Field of Classification Search ............... 514/443, 514/444; 549/49
See application file for complete search history.

(56) References Cited

U.S. PATENT DOCUMENTS

| 4,808,599 | A | 2/1989 | Dubroeucq et al. |
| 6,156,787 | A | 12/2000 | Broughton et al. |
| 2007/0259918 | A1 | 11/2007 | Orchard |
| 2008/0064740 | A1 | 3/2008 | Bolli |
| 2008/0194670 | A1 | 8/2008 | Bolli |
| 2008/0300294 | A1 | 12/2008 | Bolli |
| 2008/0318955 | A1 | 12/2008 | Bolli |
| 2009/0005421 | A1 | 1/2009 | Bolli |

FOREIGN PATENT DOCUMENTS

| EP | 0 310 321 | | 4/1989 |
| EP | 0 476 646 | A | 3/1992 |
| WO | WO-91/15583 | A1 | 10/1991 |
| WO | WO-99/46277 | A1 | 9/1999 |
| WO | WO 03/062248 | | 7/2003 |
| WO | WO 03/105771 | | 12/2003 |
| WO | WO-2004/035538 | | 4/2004 |
| WO | WO 2004/103279 | | 12/2004 |
| WO | WO 2005/032465 | | 4/2005 |
| WO | WO 2005/058848 | | 6/2005 |
| WO | WO 2007/085451 | | 8/2007 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Fujii et al., "Transition Metal-Catalyzed Intramolecular Cyclization of 1,5- and 1,6-Dienes via Direct Cleavage and Addition of the Carbon-Hydrogen Bond," Bull. Chem. Soc. Jpn., vol. 71, 1998, pp. 285-298.
T. Hla, et al., "An Abundant Transcript Induced in Differentiating Human Endothelial Cells Encodes a Polypeptide with Structural Similiarites to G-protein-coupled Receptors," J. Biol Chem, 265 (1990), pp. 9308-9313.
Philip L. Gould, "Salt selection for basic drugs," Int. J. Pharm., 33 (1986), pp. 201-217.
Mark Gibson, Editor, Pharmaceutical Preformulation and Formulation, IHS Health Group, Englewood, CO, USA, 2001.
Alfonso R. Gennaro, "Remington: The Science and Practice of Pharmacy," 20th Edition, Philadelphia College of Pharmacy and Science.
M. Mentzel, et al., "N-Metroxy-N-methylamides (Weinreb Amides) in Modern Organic Synthesis," Journal fuer Praktische Chemie/Chemiker-Zeitung 339 (1997), pp. 517-524.
J. Singh, et al., "The Growing Synthetic Utility of Weinreb's Amide," Journal fuer Praktische Chemie (Weinheim, Germany, 342 (2000), pp. 340-347.
V.K. Khlestkin, et al., "Recent Advances in the Application of N,O-Dialkylhydroxylamines in Organic Chemistry," Current Organic Chemistry 7, (2003), pp. 967-993.
A.R. Gangloff, et al., "Synthesis of 3,5-disubstituted-1,2,4-oxadiazoles using tetrabutylammonium fluoride as a mild and efficient catalyst," Tetrahedron Letters, 42 (2001), pp. 1441-1443.
T. Suzuki, et al., "Synthesis of the Selective 5-Hydroxytryptamine 4 ($5$-$HT_4$) Receptor Agonist (+)-(S)-2-Chloro-5-methoxy-4-[5-(2-piperidylmethyl)-1,2,4-oxadiaz-3-yl]aniline" Chem. Pharm. Bull., 47 (1999), pp. 120-122.
R.F. Poulain, et al., "Parallel synthesis of 1,2,4-oxadiazoles from carboxylic acids using an improved, uronium-based, activation," Tetrahedron Letters, 42 (2001), pp. 1495-1498.
R.M. Srivastava, et al., "Synthesis of 3-aryl-5-[thien-3-YL methtyl]-1,2,4-oxadiazoles," Synthetic Communications, 29 (1999), pp. 1437-1450.
E.O. John, et al., "Reactions of (Difluoroamino) difluoroacetonitrile and (Difluoroamino) difluoroacetamidoxime," Inorganic Chemistry, 27 (1988), pp. 3100-3104.
B. Kaboudin, et al., "One-pot synthesis of 1,2,4-oxadiazoles mediated by microwave irradiation under solvent-free condition," Heterocycles, vol. 60 (2003), pp. 2287-2292.
A. Hamze, et al., "Synthesis of a Various 3-Substituted 1,2,4-Oxadiazole-Containing Chiral $\beta^{3\text{-}and}$ $\alpha$-Amino Acids from Fmoc-Protected Aspartic Acid," J. Org. Chem. 68 (2003), pp. 7316-7321.

(Continued)

*Primary Examiner*—Kamal A Saeed
*Assistant Examiner*—Valerie Rodriguez-Garcia
(74) *Attorney, Agent, or Firm*—Hoxie & Associates LLC

(57) ABSTRACT

The invention relates to novel thiophene derivatives, their preparation and their use as pharmaceutically active compounds particularly as immunosuppressant agents.

20 Claims, No Drawings

OTHER PUBLICATIONS

J. Cui, et al., "Design and Synthesis of Highly Constrained Factor Xa Inhibitors: Amidine-Substituted Bis(benzoyl)-[1,3]-diazepan-2-ones and Bis(benzylidene)-bis (gem-dimethyl)cycloketones," Bioorg. Med. Chem. 11 (2003), pp. 3379-3392.

T.W. Greene, et al., "Protective Groups in Organic Synthesis," 3rd Edition, Wiley New York, 1991.

P.J. Kocienski, Protecting Group, Thieme Stuttgart, 1994.

R.E. Mewshaw, "Vilsmeier Reagents: Preparation of β-Halo-α,β-unsaturated ketones," Tetrahedron Letters, vol. 30, No. 29 (1989), pp. 3753-3756.

F.A. Lakhvich, et al., Zhurnal Organicheskoi Khimii 25 (1989), pp. 2541-2549.

C. Kashima, et al., "Preparation of 2,6-Bis(I-menthopyrzol-3-yl) pyridines and their Catalytic Activity for Asymmetric Diels Alder Reaction," Journal of Heterocyclic Chemistry 40 (2003), pp. 773-782.

I. Yavari, et al., "A new synthesis of highly functionalized 2H-pyran derivatives," Tetrahedron 59 (2003), pp. 2001-2005.

J.P. Konopelski, et al., "Carbanion Stabilization by Distal Silyloxy Groups. Origin of the High Diastereoselectivity in the Formation of Quaternary Centers with Aryllead(IV) Triacetate Reagents," Organic Letters, vol. 4, No. 23 (2002), pp. 4121-4124.

C. Wiles, et al., "The regioselective preparation of 1,3-diketones," Tetrahedron Letters 43 (2002), pp. 2945-2948.

R. Faure, et al., "Synthesis, $^1H$ and $^{13}C$ NMR Study of Pyrazoles Derives From Chiral Cyclohexanomes (3-Methylcyclohexanone, Menthone, Pulegone, Dihydrocarvone and Carvone)," Hetrocycles, vol. 57 (2002), pp. 307-316.

M. Hammadi, et al., "Clay Catalysis: Stork's Alkylation and Acylation of Cyclohexanone Without Isolation of Enamine," Synthetic Communications 26 (1996), pp. 2901-2904.

M.E. Flaugh, et al., "Acid-Catalyzed Annelation of α-Alkyl Aldehydes and α,β-Unsaturated Ketones. A One-Pot Synthesis of 4,4-Dimethyl-2-cyclohexen-1-one," Journal of Organic Chemistry 45 (1980), pp. 5399-5400.

N.R. Natale, et al., "An Efficient, General Synthesis of Spiroalkenes and Related Derivatives," Organic Preparations and Procedures International 9 (1997), pp. 103-108.

L.M. Rice, et al., "Spirans XX. Synthesis of 8,8-Dialkylazaspiro [4.5] decanes and 9,9-Dialkylazaspiro [5.5] undecanes," Journal of Heterocyclic Chemistry 10, (1973), pp. 731-735.

Wen-Dar Liu, et al., "Synthesis of 2,5-Disubstituted Thienosultines and Their Thermal Reactions with Dienophiles and Nucleophiles," Journal of Organic Chemistry 67 (2002), pp. 9267-9275.

D.W. Knight, et al., "Formation and Reactivity of Dianions Derived From 2-and 3-Thiophencarboxylic Acids," Tetrahedron Letters 21 (1980), pp. 5051-5054.

R. Raap, "Preparation of 5-Aminomethyl-2-thienylacetic Acid from 1-Methylthio-2-(2'-thienyl)ethyne," Canadian Journal of Chemistry 49 (1971), pp. 2155-2157.

F. Wuerthner, et al., "Dimerization of Merocyanine Dyes. Structural and Energetic Characterization of Dipolar Dye Aggregates and Implications for Nonlinear Optical Materials," J. Am. Chem. Soc. 124 (2002), pp. 9431-9447.

G.A. Diaz-Quijada, et al., "Investigation of Barriers To Conformational Interchange in Oligothiophenes and Oligo(Thienyl)furans," Journal of Physical Chemistry A 106 (2002), pp. 1266-1276.

G.Karminski-Zamola, et al., "Synthesis of Some Furyl- and Thienylacrylates or Diacrylates and Acrylic Acids by the Palladium Catalysed Vinylation of Substituted Bromofurans and Bromothiophenes," Heterocycles 38 (1994), pp. 759-767.

R.H. Mitchell, et al., "N-Bromosuccinimide—Chloroform, a more convenient method to nuclear brominate reactive aromatic hydrocarbons," Organic Preparations and Procedures International 29 (1997) pp. 715-719.

K. Yamagata, et al., "Studies on Heterocyclic Enaminonitriles. II.[1)] Synthesis and Aromatization of 2-Amino-3-cyano-4,5-dihydrothiophenes," Chemical & Pharmaceutical Bulletin 30 (1982), pp. 4396-4401.

B. Xu, et al., "Acyclic Analogues of Adenosine Bisphophates as P2Y Receptor Antagonists: Phosphate Substitution Leads to Multiple Pathways of Inhibition of Platelet Aggregation," J. Med. Chem. 45 (2002), pp. 5694-5709.

G. Trapani, et al., "Propofol Analogues. Synthesis, Relationships between Structure and Affinity at $GABA_A$ Receptor in Rat Brain and Differential Electrophysiological Profile at Recombinant Human $GABA_A$ Receptors," J. Med. Chem. 41 (1998) pp. 1846-1854.

A.K. Chakraborti, et al., "One-Pot Synthesis of Nitriles from Aldehydes Under Microwave Irradiation: Influence of the Medium and Mode of Microwave Irradiation on Production Formation," Tetrahedron 55 (1999), pp. 13265-13268.

E. Meyer, et al., "Synthesis of New 1,2,4- and 1,3,4-Oxadiazole Derivatives," Synthesis 2003, pp. 899-905.

R. Breslow, et al., "Antihyrophobic Cosolvent Effects for Alkylation Reactions in Water Solution, Particularly Oxygen versus Carbon Alkylations of Phenoxide Ions," J. Am. Chem. Soc. 124 (2002), pp. 3622-3635.

K.C Nicolaou, et al., "Carbocyclic Thromboxane $A_2$ 1," J. Am. Chem. Soc. 102 (1980), pp. 1404-1409.

Dubus et al., Ann. Chim., 1975, vol. 10; pp. 331-336.

Rudolph M.J., et al., "Design and Synthesis of 4,5-Disubstituted-thiophene-2-amidines as Potent Urokinase Inhibitors", Bioorganic & Medicinal Chemistry Letters, 12, (2002), pp. 491-495.

Subasinghe, N.L. et al., "Structure-Based Design, Synthesis and SAR of a Novel Series of Thiopheneamidine Urokinase Plasminogen Activator Inhibitors", Bioorganic & Medicinal Chemistry Letters, 11, (2001), pp. 1379-1382.

* cited by examiner

HYDROGENATED BENZO (C) THIOPHENE DERIVATIVES AS IMMUNOMODULATORS

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies. A further aspect of the invention relates to novel compounds of Formulae (II) and (III) that serve as intermediates to prepare compounds of Formula (I).

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see Examples).

The following paragraphs provide definitions of the various chemical moieties that make up the compounds according to the invention and are intended to apply uniformly throughout the specification and claims unless an otherwise expressly set out definition provides a broader definition.

The term $C_{1-5}$-alkyl, alone or in combination with other groups, means saturated, branched or preferably straight chain groups with one to five carbon atoms, preferably one to three carbon atoms. Examples of $C_{1-5}$-alkyl groups are methyl, ethyl, n-propyl, iso-propyl, n-butyl, iso-butyl, sec-butyl, tert-butyl, and n-pentyl.

The term $C_{1-5}$-alkoxy, alone or in combination with other groups, means an R—O group, wherein R is a $C_{1-5}$-alkyl. Preferred examples of $C_{1-5}$-alkoxy groups are methoxy, ethoxy, propoxy, iso-propoxy, iso-butoxy, sec-butoxy and tert-butoxy.

The term hydroxy-$C_{2-5}$-alkoxy, alone or in combination with other groups, means a straight or branched alkoxy chain bearing a hydroxy group whereby there are at least two carbon atoms between the hydroxy group and the oxygen of the $C_{2-5}$-alkoxy group. Examples of hydroxy-$C_{2-5}$-alkoxy groups are 2-hydroxy-ethoxy, 3-hydroxy-propoxy, 2-hydroxy-propoxy, 4-hydroxy-butoxy, 3-hydroxy-1-methyl-propoxy, 3-hydroxy-butoxy, etc.

The term mono- or di-($C_{1-5}$-alkyl)amino means an R'—NH— or an R'—NR"— group, respectively, wherein R' and R" are each independently a $C_{1-5}$-alkyl group. Preferred examples of mono- or di-($C_{1-5}$-alkyl)amino groups are methylamino, ethylamino, N,N-dimethylamino, and N-methyl-N-ethyl-amino.

The term halogen means fluoro, chloro, bromo or iodo, preferably fluoro or chloro.

If the group A of Formula (I) represents an asymmetric bivalent group, such a group is connected in a way that the beginning part of the group A is linked to the thiophene ring of Formula (I) (that means that for example the —CO part of —CONH—CH$_2$— is linked to the thiophene ring of Formula (I)).

Where the plural form is used for compounds, salts, pharmaceutical compositions, diseases and the like, this is intended to mean also a single compound, salt, or the like.

Any reference hereinbefore or hereinafter to a compound of Formula (I), (II) or (III) is to be understood as referring also to configurational isomers such as optically pure enantiomers, mixtures of enantiomers such as racemates, diastereomers, mixtures of diastereomers, diastereomeric racemates, and mixtures of diastereomeric racemates, as well as salts (especially pharmaceutically acceptable salts) and solvent complexes (including hydrates) of such compounds, and morphological forms, as appropriate and expedient.

Salts are preferably the pharmaceutically acceptable salts of the compounds of Formula (I).

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or poly-acid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, trifluoroacetic acid, and the like that are non toxic to living organisms or in case the compound of Formula (I) is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", Int. J. Pharm. (1986), 33, 201-217.

The compounds of Formulae (I), (II) and (III) may contain asymmetric carbon atoms. Substituents at a double bond or a ring may be present in cis-(=Z—) or trans (=E-) form unless indicated otherwise. The compounds of Formulae (I), (II) and (III) may thus be present as mixtures of stereoisomers or preferably as pure stereoisomers. Mixtures of stereoisomers may be separated in a manner known per se, e.g. by column chromatography, thin layer chromatography, HPLC or crystallization.

i) The invention relates to novel thiophene compounds of the Formula (I),

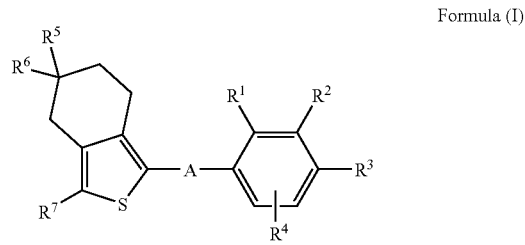

Formula (I)

wherein

A represents —CONH—CH$_2$—, —CO—CH=CH—, —CO—CH$_2$CH$_2$—, —CO—CH$_2$—O—, —CO—CH$_2$—NH—,

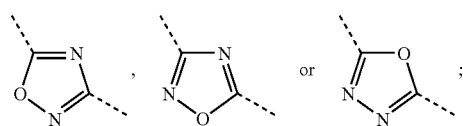

$R^1$ represents hydrogen, $C_{1-5}$-alkyl, $C_{1-5}$-alkoxy, or halogen;

$R^2$ represents hydrogen, $C_{1-5}$-alkyl, $C_{1-5}$-alkoxy, trifluoromethyl, trifluoromethoxy or halogen;

$R^3$ represents hydrogen, hydroxy-$C_{1-5}$-alkyl, 2,3-dihydroxypropyl, di-(hydroxy-$C_{1-5}$-alkyl)-$C_{1-5}$-alkyl, —CH$_2$—(CH$_2$)$_k$—NR$^{31}$R$^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —CH$_2$—(CH$_2$)$_n$—CONR$^{31}$R$^{32}$, —CO—NHR$^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —(CH$_2$)$_n$CH(OH)—CH$_2$—NR$^{31}$R$^{32}$, hydroxy, $C_{1-5}$-alkoxy, fluoro-$C_{1-5}$-alkoxy, hydroxy-$C_{2-5}$-alkoxy, di-(hydroxy-$C_{1-5}$-alkyl)-$C_{1-5}$-alkoxy, 1-glyceryl, 2-glyceryl, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]- ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-($C_{1-5}$-alkylcarbamoyl)propoxy, 3-(2-hydroxyethylcarbamoyl) propoxy, —$OCH_2$—CH(OH)—$CH_2$—$NR^{31}R^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$—$NHSO_2R^{33}$ —$OCH_2$—CH(OH)—$CH_2$—$NHSO_2R^{33}$, —$CH_2$—$(CH_2)_k$—$NHCOR^{34}$, —$(CH_2)_n$CH(OH)—$CH_2$—$NHCOR^{34}$, —$OCH_2$—$(CH_2)_m$—$NHCOR^{34}$, —$OCH_2$—CH(OH)—$CH_2$—$NHCOR^{34}$, or —$SO_2NHR^{31}$;

$R^{31}$ represents hydrogen, methyl, ethyl, 1-propyl, 2-propyl, 2-hydroxyethyl, 2-hydroxy-1-hydroxymethyl-ethyl, 2,3-dihydroxypropyl, 2-$C_{1-5}$-alkoxyethyl, 3-hydroxypropyl, 3-$C_{1-5}$-alkoxypropyl, 2-aminoethyl, 2-($C_{1-5}$-alkylamino) ethyl, 2-(di-($C_{1-5}$-alkyl)amino)ethyl, carboxymethyl, $C_{1-5}$-alkylcarboxymethyl, 2-carboxyethyl, or 2-($C_{1-5}$-alkylcarboxy)ethyl;

$R^{32}$ represents hydrogen, methyl, or ethyl;

$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

$R^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;
m represents the integer 1 or 2;
n represents 0, 1, or 2;
$R^4$ represents hydrogen, $C_{1-5}$-alkyl or halogen;
$R^5$ represents methyl or ethyl;
$R^6$ represents methyl or ethyl;
or $R^5$ and $R^6$ together form a carbocyclic 3-, 4-, or 5-membered ring; and $R^7$ represents hydrogen, methyl, ethyl, n-propyl, isopropyl, trifluoromethyl, hydroxymethyl, methoxymethyl, methoxy, methylthio, hydroxycarbonyl, aminocarbonyl, mono- or di-($C_{1-5}$-alkyl)aminocarbonyl, amino, mono- or di-($C_{1-5}$-alkyl) amino;

and configurational isomers such as optically pure enantiomers, mixtures of enantiomers such as racemates, diastereomers, mixtures of diastereomers, diastereomeric racemates, and mixtures of diastereomeric racemates, as well as salts and solvent complexes of such compounds, and morphological forms.

ii) A particular embodiment of the invention relates to thiophene derivatives according to embodiment i), wherein A represents

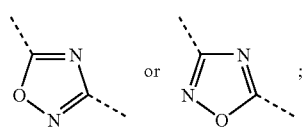

$R^3$ represents hydrogen, hydroxy-$C_{1-5}$-alkyl, 2,3-dihydroxypropyl, di-(hydroxy-$C_{1-5}$-alkyl)-$C_{1-5}$-alkyl, —$CH_2$—$(CH_2)_k$—$NR^{31}R^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —$CH_2$—$(CH_2)_n$—$CONR^{31}R^{32}$, —CO—$NHR^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —$(CH_2)_n$CH(OH)—$CH_2$—$NR^{31}R^{32}$, hydroxy, $C_{1-5}$-alkoxy, fluoro-$C_{1-5}$-alkoxy, hydroxy-$C_{2-5}$-alkoxy, di-(hydroxy-$C_{1-5}$-alkyl)-$C_{1-5}$-alkoxy, 1-glyceryl, 2-glyceryl, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$- alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-($C_{1-5}$-alkylcarbamoyl)propoxy, 3-(2-hydroxyethylcarbamoyl) propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_n$CH(OH)—CH$_2$—NHSO$_2$R$^{33}$—OCH$_2$—(CH$_2$)$_m$NHSO$_2$R$^{33}$—OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$; and $R^{31}$ represents hydrogen, methyl, ethyl, 1-propyl, 2-propyl, 2-hydroxyethyl, 2-hydroxy-1-hydroxymethyl-ethyl, 2-$C_{1-5}$-alkoxyethyl, 3-hydroxypropyl, 3-$C_{1-5}$-alkoxypropyl, 2-aminoethyl, 2-($C_{1-5}$-alkylamino)ethyl, 2-(di-($C_{1-5}$-alkyl)amino)ethyl, carboxymethyl, $C_{1-5}$-alkylcarboxymethyl, 2-carboxyethyl, or 2-($C_{1-5}$-alkylcarboxy)ethyl;

and wherein k, m, n, $R^{32}$, $R^{33}$ and $R^{34}$ are as defined in embodiment i).

iii) A particular embodiment of the invention relates to thiophene derivatives according to embodiment i) or ii), wherein A represents —CO—CH$_2$—CH$_2$—.

iv) Another particular embodiment of the invention relates to thiophene derivatives according to embodiment i) or ii), wherein A represents —CO—CH$_2$—NH—.

v) Another particular embodiment of the invention relates to thiophene derivatives according to embodiment i) or ii), wherein A represents

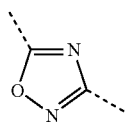

vi) Another particular embodiment of the invention relates to thiophene derivatives according to embodiment i), wherein A represents

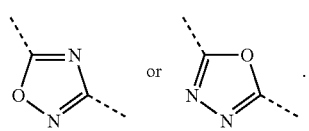

vii) A preferred embodiment of the invention relates to thiophene derivatives according to any one of embodiments i) to vi), wherein $R^1$ and $R^4$ represent hydrogen and $R^2$ represents a methyl group.

viii) Another preferred embodiment of the invention relates to thiophene derivatives according to any one of embodiments i) to vi), wherein $R^1$ represents hydrogen, $R^2$ and $R^4$ represent a methyl group, and $R^4$ is in the ortho-position with respect to $R^3$.

ix) Another preferred embodiment of the invention relates to thiophene derivatives according to any one of embodiments i) to vi), wherein $R^1$ represents hydrogen, $R^2$ represents a methyl group, and $R^4$ represents an ethyl group in the ortho-position with respect to $R^3$.

x) Another preferred embodiment of the invention relates to thiophene derivatives according to any one of embodiments i) to vi), wherein $R^1$ represents hydrogen, $R^2$ represents a methyl group, and $R^4$ represents chloro in the ortho-position with respect to $R^3$.

xi) Another preferred embodiment of the invention relates to thiophene derivatives according to any one of embodiments i) to vi), wherein $R^1$ and $R^4$ represent hydrogen and $R^2$ represents chloro.

xii) Another preferred embodiment of the invention relates to thiophene derivatives according to any one of embodiments i) to vi), wherein $R^1$ represents hydrogen, $R^2$ represents a methoxy group, and $R^4$ represents chloro or fluoro both in the ortho-position with respect to $R^3$.

xiii) Another preferred embodiment of the invention relates to thiophene derivatives according to any one of embodiments i) to vi), wherein $R^1$ represents a methoxy group and $R^2$ and $R^4$ represent hydrogen.

xiv) A further preferred embodiment of the invention relates to thiophene derivatives according to any one of embodiments i) to xiii), wherein $R^3$ represents hydroxy-$C_{1-5}$-alkyl, 2,3-dihydroxypropyl, di-(hydroxy-$C_{1-5}$-alkyl)-$C_{1-5}$-alkyl, —CH$_2$—(CH$_2$)$_k$—NR$^{31}$R$^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —CH$_2$—(CH$_2$)$_n$—CONR$^{31}$R$^{32}$, —CO—NHR$^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, or —(CH$_2$)$_n$CH(OH)—CH$_2$—NR$^{31}$R$^{32}$, and wherein k, n, $R^{31}$ and $R^{32}$ are as defined in embodiment i) above.

xv) Another further preferred embodiment of the invention relates to thiophene derivatives according to any one of embodiments i) to xiii), wherein $R^3$ represents hydroxy-$C_{1-5}$-alkyl, 2,3-dihydroxypropyl, di-(hydroxy-$C_{1-5}$-alkyl)-$C_{1-5}$-alkyl, —CH$_2$—(CH$_2$)$_k$—NR$^{31}$R$^{32}$, (azetidine-3-carboxylic acid)-1-yl-methyl, 2-[(azetidine-3-carboxylic acid)-1-yl]-ethyl, 3-[(azetidine-3-carboxylic acid)-1-yl]-propyl, (pyrrolidine-3-carboxylic acid)-1-yl-methyl, (pyrrolidine-2-carboxylic acid)-1-yl-methyl, 2-[(pyrrolidine-3-carboxylic acid)-1-yl]-ethyl, 2-[(pyrrolidine-2-carboxylic acid)-1-yl]-ethyl, 3-[(pyrrolidine-3-carboxylic acid)-1-yl]-propyl, 3-[(pyrrolidine-2-carboxylic acid)-1-yl]-propyl, —CO—NHR$^{31}$, or —(CH$_2$)$_n$CH(OH)—CH$_2$—NR$^{31}$R$^{32}$, wherein R$^{31}$ represents hydrogen, methyl, 2-hydroxyethyl, 2-hydroxy-1-hydroxymethyl-ethyl, or 2-aminoethyl, R$^{32}$ represents hydrogen, and k and n are as defined in embodiment i) above.

xvi) Another further preferred embodiment of the invention relates to thiophene derivatives according to any one of embodiments i) to xiii), wherein R$^3$ represents hydroxy, hydroxy-C$_{2-5}$-alkoxy, di-(hydroxy-C$_{1-5}$-alkyl)-C$_{1-5}$-alkoxy, 1-glyceryl, 2-glyceryl, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(C$_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-(C$_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid C$_{1-5}$-alkylester)-1-yl]-ethoxy, 2-[(pyrrolidine-3-carboxylic acid)-1-yl]-ethoxy, 2-[(pyrrolidine-3-carboxylic acid C$_{1-5}$-alkylester)-1-yl]-ethoxy, 2-[(pyrrolidine-2-carboxylic acid)-1-yl]-ethoxy, 2-[(pyrrolidine-2-carboxylic acid C$_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid C$_{1-5}$-alkylester)-1-yl]-propoxy, 3-[(pyrrolidine-3-carboxylic acid)-1-yl]-propoxy, 3-[(pyrrolidine-3-carboxylic acid C$_{1-5}$-alkylester)-1-yl]-propoxy, 3-[(pyrrolidine-2-carboxylic acid)-1-yl]-propoxy, 3-[(pyrrolidine-2-carboxylic acid C$_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-(C$_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid C$_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid C$_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid C$_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(C$_{1-5}$-alkyl)-piperazin-1-yl]-propoxy, 2-hydroxy-3-[4-(2-hydroxy-ethyl)-piperazin-1-yl]-propoxy, or 2-hydroxy-3-morpholin-4-yl-propoxy, and wherein m, R$^{31}$ and R$^{32}$ are as defined in embodiment i) above.

xvii) A still further preferred embodiment of the invention relates to thiophene derivatives according to any one of embodiments i) to xiii), wherein R$^3$ represents hydroxy, hydroxy-C$_{2-5}$-alkoxy, di-(hydroxy-C$_{1-5}$-alkyl)-C$_{1-5}$-alkoxy, 1-glyceryl, 2-glyceryl, 2-hydroxy-3-methoxy-propoxy, —OCH$_2$—(CH$_2$)$_m$—NR$^{31}$R$^{32}$, 2-[(azetidine-3-carboxylic acid)-1-yl]-ethoxy, 3-[(azetidine-3-carboxylic acid)-1-yl]-propoxy, —O—CH$_2$—CONR$^{31}$R$^{32}$, 1-(1-(3-carboxy-azetidinyl))-1-oxo-2-ethoxy, 3-carbamoyl-propoxy, 3-(C$_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 2-hydroxy-3-[(pyrrolidine-3-carboxylic acid)-1-yl]-propoxy, or 2-hydroxy-3-[(pyrrolidine-2-carboxylic acid)-1-yl]-propoxy, wherein R$^{31}$ represents hydrogen, methyl, 2-hydroxyethyl, 2-hydroxy-1-hydroxymethyl-ethyl, 2-aminoethyl, or 2-carboxyethyl, R$^{32}$ represents hydrogen, and wherein m is as defined in embodiment i) above.

xviii) Another further preferred embodiment of the invention relates to thiophene derivatives according to any one of embodiments i) to xiii), wherein R$^3$ represents —CH$_2$—(CH$_2$)$_k$—NHSO$_2$R$^{33}$, —(CH$_2$)$_n$CH(OH)—CH$_2$—NHSO$_2$R$^{33}$—OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$ and wherein k, m, n, R$^{33}$ and R$^{34}$ are as in embodiment i) above.

xix) A particularly preferred embodiment of the invention relates to thiophene derivatives according to any one of embodiments i) to xviii), wherein R$^5$ and R$^6$ represent methyl, or together form a carbocyclic 3-, or 4-membered ring.

xx) Another particularly preferred embodiment of the invention relates to thiophene derivatives according to any one of embodiments i) to xix), wherein R$^7$ represents methyl, ethyl, propyl or isopropyl.

xxi) Specific thiophene derivatives according to Formula (I) are:

3-(4-hydroxy-3,5-dimethyl-phenyl)-1-(3,5,5-trimethyl-4,5,6,7-tetrahydro-benzo[c]thiophen-1-yl)-propan-1-one, 3-[4-(2-hydroxy-ethoxy)-3,5-dimethyl-phenyl]-1-(3,5,5-trimethyl-4,5,6,7-tetrahydro-benzo[c]thiophen-1-yl)-propan-1-one, 3-[3-chloro-4-((S)-2,3-dihydroxy-propoxy)-5-methoxy-phenyl]-1-(3,5,5-trimethyl-4,5,6,7-tetrahydro-benzo[c]thiophen-1-yl)-propan-1-one, 3-[4-(3-hydroxy-propoxy)-3,5-dimethyl-phenyl]-1-(3,5,5-trimethyl-4,5,6,7-tetrahydro-benzo[c]thiophen-1-yl)-propan-1-one, 3-[4-((S)-2,3-dihydroxy-propoxy)-3,5-dimethyl-phenyl]-1-(3,5,5-trimethyl-4,5,6,7-tetrahydro-benzo[c]thiophen-1-yl)-propan-1-one, 3-[4-((R)-2,3-dihydroxy-propoxy)-3,5-dimethyl-phenyl]-1-(3,5,5-trimethyl-4,5,6,7-tetrahydro-benzo[c]thiophen-1-yl)-propan-1-one, 3-[4-(2-hydroxy-3-methoxy-propoxy)-3,5-dimethyl-phenyl]-1-(3,5,5-trimethyl-4,5,6,7-tetrahydro-benzo[c]thiophen-1-yl)-propan-1-one, 3-[4-(3-amino-2-hydroxy-propoxy)-3,5-dimethyl-phenyl]-1-(3,5,5-trimethyl-4,5,6,7-tetrahydro-benzo[c]thiophen-1-yl)-propan-1-one, 3-[4-(2-hydroxy-3-methylamino-propoxy)-3,5-dimethyl-phenyl]-1-(3,5,5-trimethyl-4,5,6,7-tetrahydro-benzo[c]thiophen-1-yl)-propan-1-one, 3-[4-[2-hydroxy-3-(2-hydroxy-ethylamino)-propoxy]-3,5-dimethyl-phenyl]-1-(3,5,5-trimethyl-4,5,6,7-tetrahydro-benzo[c]thiophen-1-yl)-propan-1-one, 3-{4-[2-hydroxy-3-(2-hydroxy-1-hydroxymethyl-ethylamino)-propoxy]-3,5-dimethyl-phenyl}-1-(3,5,5-trimethyl-4,5,6,7-tetrahydro-benzo[c]thiophen-1-yl)-propan-1-one, 3-{4-[3-(3-ethoxy-propylamino)-2-hydroxy-propoxy]-3,5-dimethyl-phenyl}-1-(3,5,5-trimethyl-4,5,6,7-tetrahydro-benzo[c]thiophen-1-yl)-propan-1-one, 3-{4-[3-(2-amino-ethylamino)-2-hydroxy-propoxy]-3,5-dimethyl-phenyl}-1-(3,5,5-trimethyl-4,5,6,7-tetrahydro-benzo[c]thiophen-1-yl)-propan-1-one,
3-(3-{2,6-dimethyl-4-[3-oxo-3-(3,5,5-trimethyl-4,5,6,7-tetrahydro-benzo[c]thiophen-1-yl)-propyl]-phenoxy}-2-hydroxy-propylamino)-propionic acid,
1-(3-{2,6-dimethyl-4-[3-oxo-3-(3,5,5-trimethyl-4,5,6,7-tetrahydro-benzo[c]thiophen-1-yl)-propyl]-phenoxy}-2-hydroxy-propyl)-azetidine-3-carboxylic acid,
3-[3-chloro-4-((R)-2,3-dihydroxy-propoxy)-5-methoxy-phenyl]-1-(3,5,5-trimethyl-4,5,6,7-tetrahydro-benzo[c]thiophen-1-yl)-propan-1-one,
3-[4-(2-hydroxy-propoxy)-3,5-dimethyl-phenyl]-1-(3,5,5-trimethyl-4,5,6,7-tetrahydro-benzo[c]thiophen-1-yl)-propan-1-one,
3-[4-(3-amino-2-hydroxy-propoxy)-3-chloro-5-methoxy-phenyl]-1-(3,5,5-trimethyl-4,5,6,7-tetrahydro-benzo[c]thiophen-1-yl)-propan-1-one,
3-{3-chloro-4-[2-hydroxy-3-(2-hydroxy-1-hydroxymethyl-ethylamino)-propoxy]-5-methoxy-phenyl}-1-(3,5,5-trimethyl-4,5,6,7-tetrahydro-benzo[c]thiophen-1-yl)-propan-1-one,
3-{4-[3-(2-amino-ethylamino)-2-hydroxy-propoxy]-3-chloro-5-methoxy-phenyl}-1-(3,5,5-trimethyl-4,5,6,7-tetrahydro-benzo[c]thiophen-1-yl)-propan-1-one,
3-(3-[2-chloro-6-methoxy-4-[3-oxo-3-(3,5,5-trimethyl-4,5,6,7-tetrahydro-benzo[c]thiophen-1-yl)-propyl]-phenoxy}-2-hydroxy-propylamino)-propionic acid,
1-(3-{2-chloro-6-methoxy-4-[3-oxo-3-(3,5,5-trimethyl-4,5,6,7-tetrahydro-benzo[c]thiophen-1-yl)-propyl]-phenoxy}-2-hydroxy-propyl)-azetidine-3-carboxylic acid,
(E)-1-(3-ethyl-5,5-dimethyl-4,5,6,7-tetrahydro-benzo[c]thiophen-1-yl)-3-(4-hydroxy-3,5-dimethyl-phenyl)-propenone,
1-(3-ethyl-5,5-dimethyl-4,5,6,7-tetrahydro-benzo[c]thiophen-1-yl)-3-(4-hydroxy-3,5-dimethyl-phenyl)-propan-1-one,
1-(3-ethyl-5,5-dimethyl-4,5,6,7-tetrahydro-benzo[c]thiophen-1-yl)-3-[4-(2-hydroxy-ethoxy)-3,5-dimethyl-phenyl]-propan-1-one,
1-(3-ethyl-5,5-dimethyl-4,5,6,7-tetrahydro-benzo[c]thiophen-1-yl)-3-[4-(2-hydroxy-propoxy)-3,5-dimethyl-phenyl]-propan-1-one,
1-(3-ethyl-5,5-dimethyl-4,5,6,7-tetrahydro-benzo[c]thiophen-1-yl)-3-[4-(3-hydroxy-propoxy)-3,5-dimethyl-phenyl]-propan-1-one,
3-[4-((S)-2,3-dihydroxy-propoxy)-3,5-dimethyl-phenyl]-1-(3-ethyl-5,5-dimethyl-4,5,6,7-tetrahydro-benzo[c]thiophen-1-yl)-propan-1-one,
3-[4-((R)-2,3-dihydroxy-propoxy)-3,5-dimethyl-phenyl]-1-(3-ethyl-5,5-dimethyl-4,5,6,7-tetrahydro-benzo[c]thiophen-1-yl)-propan-1-one,
1-(3-ethyl-5,5-dimethyl-4,5,6,7-tetrahydro-benzo[c]thiophen-1-yl)-3-[4-(2-hydroxy-3-methoxy-propoxy)-3,5-dimethyl-phenyl]-propan-1-one,
3-[4-(2-dimethylamino-ethoxy)-3,5-dimethyl-phenyl]-1-(3-ethyl-5,5-dimethyl-4,5,6,7-tetrahydro-benzo[c]thiophen-1-yl)-propan-1-one,
3-[3,5-dimethyl-4-(2-pyrrolidin-1-yl-ethoxy)-phenyl]-1-(3-ethyl-5,5-dimethyl-4,5,6,7-tetrahydro-benzo[c]thiophen-1-yl)-propan-1-one,
1-(3-ethyl-5,5-dimethyl-4,5,6,7-tetrahydro-benzo[c]thiophen-1-yl)-3-[4-(2-hydroxy-3-isopropylamino-propoxy)-3,5-dimethyl-phenyl]-propan-1-one,
1-(3-ethyl-5,5-dimethyl-4,5,6,7-tetrahydro-benzo[c]thiophen-1-yl)-3-{4-[2-hydroxy-3-(2-hydroxy-ethylamino)-propoxy]-3,5-dimethyl-phenyl}-propan-1-one,
1-(3-ethyl-5,5-dimethyl-4,5,6,7-tetrahydro-benzo[c]thiophen-1-yl)-3-{4-[2-hydroxy-3-(2-hydroxy-1-hydroxymethyl-ethylamino)-propoxy]-3,5-dimethyl-phenyl}-propan-1-one,
3-{4-[3-(3-ethoxy-propylamino)-2-hydroxy-propoxy]-3,5-dimethyl-phenyl}-1-(3-ethyl-5,5-dimethyl-4,5,6,7-tetrahydro-benzo[c]thiophen-1-yl)-propan-1-one,
3-[4-[3-(2-amino-ethylamino)-2-hydroxy-propoxy]-3,5-dimethyl-phenyl}-1-(3-ethyl-5,5-dimethyl-4,5,6,7-tetrahydro-benzo[c]thiophen-1-yl)-propan-1-one,
3-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propylamino)-propionic acid,
3-[4-(2-amino-ethoxy)-3,5-dimethyl-phenyl]-1-(3,5,5-trimethyl-4,5,6,7-tetrahydro-benzo[c]thiophen-1-yl)-propan-1-one,
3-[4-(2-amino-ethoxy)-3-chloro-5-methoxy-phenyl]-1-(3,5,5-trimethyl-4,5,6,7-tetrahydro-benzo[c]thiophen-1-yl)-propan-1-one,
3-[4-(3-amino-propoxy)-3-chloro-5-methoxy-phenyl]-1-(3,5,5-trimethyl-4,5,6,7-tetrahydro-benzo[c]thiophen-1-yl)-propan-1-one,
3-[4-(2-amino-ethoxy)-3,5-dimethyl-phenyl]-1-(3-ethyl-5,5-dimethyl-4,5,6,7-tetrahydro-benzo[c]thiophen-1-yl)-propan-1-one,
3-[4-(2-ethylamino-ethoxy)-3,5-dimethyl-phenyl]-1-(3-ethyl-5,5-dimethyl-4,5,6,7-tetrahydro-benzo[c]thiophen-1-yl)-propan-1-one,
1-(3-ethyl-5,5-dimethyl-4,5,6,7-tetrahydro-benzo[c]thiophen-1-yl)-3-[4-(2-isopropylamino-ethoxy)-3,5-dimethyl-phenyl]-propan-1-one,
1-(3-ethyl-5,5-dimethyl-4,5,6,7-tetrahydro-benzo[c]thiophen-1-yl)-3-{4-[2-(2-hydroxy-ethylamino)-ethoxy]-3,5-dimethyl-phenyl}-propan-1-one,
1-(3-ethyl-5,5-dimethyl-4,5,6,7-tetrahydro-benzo[c]thiophen-1-yl)-3-{4-[2-(2-hydroxy-1-hydroxymethyl-ethylamino)-ethoxy]-3,5-dimethyl-phenyl}-propan-1-one,
3-{4-[2-(2-amino-ethylamino)-ethoxy]-3,5-dimethyl-phenyl}-1-(3-ethyl-5,5-dimethyl-4,5,6,7-tetrahydro-benzo[c]thiophen-1-yl)-propan-1-one,
3-[4-(3-amino-propoxy)-3,5-dimethyl-phenyl]-1-(3-ethyl-5,5-dimethyl-4,5,6,7-tetrahydro-benzo[c]thiophen-1-yl)-propan-1-one,
3-[4-(3-ethylamino-propoxy)-3,5-dimethyl-phenyl]-1-(3-ethyl-5,5-dimethyl-4,5,6,7-tetrahydro-benzo[c]thiophen-1-yl)-propan-1-one,
1-(3-ethyl-5,5-dimethyl-4,5,6,7-tetrahydro-benzo[c]thiophen-1-yl)-3-[4-(3-isopropylamino-propoxy)-3,5-dimethyl-phenyl]-propan-1-one,
1-(3-ethyl-5,5-dimethyl-4,5,6,7-tetrahydro-benzo[c]thiophen-1-yl)-3-{4-[3-(2-hydroxy-ethylamino)-propoxy]-3,5-dimethyl-phenyl}-propan-1-one,
1-(3-ethyl-5,5-dimethyl-4,5,6,7-tetrahydro-benzo[c]thiophen-1-yl)-3-{4-[3-(2-hydroxy-1-hydroxymethyl-ethylamino)-propoxy]-3,5-dimethyl-phenyl}-propan-1-one, and
3-{4-[3-(2-amino-ethylamino)-propoxy]-3,5-dimethyl-phenyl}-1-(3-ethyl-5,5-dimethyl-4,5,6,7-tetrahydro-benzo[c]thiophen-1-yl)-propan-1-one.

xxii) Specific preferred thiophene derivatives according to Formula (I) are further:

N-(3-{4-[5-(5,5-dimethyl-4,5,6,7-tetrahydro-benzo[c]thiophen-1-yl)-[1,2,4]oxadiazol-3-yl]-2,6-dimethyl-phenoxy-2-hydroxy-propyl)-2-hydroxy-acetamide;

N-(3-{4-[5-(5,5-dimethyl-4,5,6,7-tetrahydro-benzo[c]thiophen-1-yl)-[1,2,4]oxadiazol-3-yl]-2-ethyl-6-methyl-phenoxy}-2-hydroxy-propyl)-2-hydroxy-acetamide;

N-(3-{4-[5-(5,5-dimethyl-4,5,6,7-tetrahydro-benzo[c]thiophen-1-yl)-[1,2,4]oxadiazol 3-yl]-2-ethyl-6-methyl-phenoxy}-2-hydroxy-propyl)-3-hydroxy-propionamide;

N-(3-{2,6-dimethyl-4-[3-oxo-3-(3,5,5-trimethyl-4,5,6,7-tetrahydro-benzo[c]thiophen-1-yl)-propyl]-phenoxy}-2-hydroxy-propyl)-2-hydroxy-acetamide;

N-(3-{2-ethyl-6-methyl-4-[3-oxo-3-(3,5,5-trimethyl-4,5,6,7-tetrahydro-benzo[c]thiophen-1-yl)-propyl]-phenoxy}-2-hydroxy-propyl)-2-hydroxy-acetamide;

N-(3-{2-chloro-6-methoxy-4-[3-oxo-3-(3,5,5-trimethyl-4,5,6,7-tetrahydro-benzo[c]thiophen-1-yl)-propyl]-phenoxy}-2-hydroxy-propyl)-2-hydroxy-acetamide;

N-(3-{2-ethyl-6-methyl-4-[5-(3,5,5-trimethyl-4,5,6,7-tetrahydro-benzo[c]thiophen-1-yl)-[1,2,4]oxadiazol-3-yl]-phenoxy}-2-hydroxy-propyl)-2-hydroxy-acetamide;

1-(3-ethyl-5,5-dimethyl-4,5,6,7-tetrahydro-benzo[c]thiophen-1-yl)-3-[4-(2-hydroxy-ethoxy)-2-methoxy-phenyl]-propan-1-one;

3-[4-(2,3-dihydroxy-propoxy)-3-ethyl-5-methyl-phenyl]-1-(3-ethyl-5,5-dimethyl-4,5,6,7-tetrahydro-benzo[c]thiophen-1-yl)-propan-1-one;

3-[4-(2,3-dihydroxy-propoxy)-3,5-diethyl-phenyl]-1-(3-ethyl-5,5-dimethyl-4,5,6,7-tetrahydro-benzo[c]thiophen-1-yl)-propan-1-one;

3-[4-(2,3-dihydroxy-propoxy)-2-methoxy-phenyl]-1-(3-ethyl-5,5-dimethyl-4,5,6,7-tetrahydro-benzo[c]thiophen-1-yl)-propan-1-one;

3-[3,5-dimethyl-4-(2-methylamino-ethoxy)-phenyl]-1-(3-ethyl-5,5-dimethyl-4,5,6,7-tetrahydro-benzo[c]thiophen-1-yl)-propan-1-one;

N-(2-{4-[3-(3-ethyl-5,5-dimethyl-4,5,6,7-tetrahydro-benzo[c]thiophen-1-yl)-3-oxo-propyl]-2,6-dimethyl-phenoxy}-ethyl)-methanesulfonamide;

N-(2-{2-ethyl-4-[3-(3-ethyl-5,5-dimethyl-4,5,6,7-tetrahydro-benzo[c]thio-phen-1-yl)-3-oxo-propyl]-6-methyl-phenoxy}-ethyl)-methanesulfonamide;

ethanesulfonic acid (2-{2-ethyl-4-[3-(3-ethyl-5,5-dimethyl-4,5,6,7-tetrahydro-benzo[c]thiophen-1-yl)-3-oxo-propyl]-6-methyl-phenoxy}-ethyl)-amide;

N-(2-{2,6-diethyl-4-[3-(3-ethyl-5,5-dimethyl-4,5,6,7-tetrahydro-benzo[c]thiophen-1-yl)-3-oxo-propyl]-phenoxy}-ethyl)-methanesulfonamide;

N-(2-{2-chloro-4-[3-(3-ethyl-5,5-dimethyl-4,5,6,7-tetrahydro-benzo[c]thiophen-1-yl)-3-oxo-propyl]-6-methyl-phenoxy}-ethyl)-methanesulfonamide;

N-(2-{2-chloro-4-[3-(3-ethyl-5,5-dimethyl-4,5,6,7-tetrahydro-benzo[c]thiophen-1-yl)-3-oxo-propyl]-6-methoxy-phenoxy}-ethyl)-methanesulfonamide;

N-(2-{4-[3-(3-ethyl-5,5-dimethyl-4,5,6,7-tetrahydro-benzo[c]thiophen-1-yl)-3-oxo-propyl]-3-methoxy-phenoxy}-ethyl)-methanesulfonamide;

N-(2-{4-[3-(3-ethyl-5,5-dimethyl-4,5,6,7-tetrahydro-benzo[c]thiophen-1-yl)-3-oxo-propyl]-2,6-dimethyl-phenoxy}-ethyl)-2-hydroxy-acetamide;

N-(2-{4-[3-(3-ethyl-5,5-dimethyl-4,5,6,7-tetrahydro-benzo[c]thiophen-1-yl)-3-oxo-propyl]-2,6-dimethyl-phenoxy}-ethyl)-3-hydroxy-propionamide;

N-(2-{2-ethyl-4-[3-(3-ethyl-5,5-dimethyl-4,5,6,7-tetrahydro-benzo[c]thiophen-1-yl)-3-oxo-propyl]-6-methyl-phenoxy}-ethyl)-2-hydroxy-acetamide;

N-(2-{2,6-diethyl-4-[3-(3-ethyl-5,5-dimethyl-4,5,6,7-tetrahydro-benzo[c]thiophen-1-yl)-3-oxo-propyl]-phenoxy}-ethyl)-2-hydroxy-acetamide;

N-(2-{2-chloro-4-[3-(3-ethyl-5,5-dimethyl-4,5,6,7-tetrahydro-benzo[c]thiophen-1-yl)-3-oxo-propyl]-6-methyl-phenoxy}-ethyl)-2-hydroxy-acetamide;

N-(2-{2-chloro-4-[3-(3-ethyl-5,5-dimethyl-4,5,6,7-tetrahydro-benzo[c]thiophen-1-yl)-3-oxo-propyl]-6-methoxy-phenoxy}-ethyl)-2-hydroxy-acetamide;

N-(2-{4-[3-(3-ethyl-5,5-dimethyl-4,5,6,7-tetrahydro-benzo[c]thiophen-1-yl)-3-oxo-propyl]-3-methoxy-phenoxy}-ethyl)-2-hydroxy-acetamide;

N-(2-{4-[3-(3-ethyl-5,5-dimethyl-4,5,6,7-tetrahydro-benzo[c]thiophen-1-yl)-3-oxo-propyl]-2,6-dimethyl-phenoxy}-ethyl)-2-methylamino-acetamide;

N-(2-{2-ethyl-4-[3-(3-ethyl-5,5-dimethyl-4,5,6,7-tetrahydro-benzo[c]thiophen-1-yl)-3-oxo-propyl]-6-methyl-phenoxy}-ethyl)-2-methylamino-acetamide;

N-(2-{2-ethyl-4-[3-(3-ethyl-5,5-dimethyl-4,5,6,7-tetrahydro-benzo[c]thiophen-1-yl)-3-oxo-propyl]-6-methyl-phenoxy}-ethyl)-3-methylamino-propionamide;

N-(2-{2-chloro-4-[3-(3-ethyl-5,5-dimethyl-4,5,6,7-tetrahydro-benzo[c]thiophen-1-yl)-3-oxo-propyl]-6-methoxy-phenoxy}-ethyl)-2-methylamino-acetamide;

N-(2-{4-[3-(3-ethyl-5,5-dimethyl-4,5,6,7-tetrahydro-benzo[c]thiophen-1-yl)-3-oxo-propyl]-3-methoxy-phenoxy}-ethyl)-2-methylamino-acetamide;

3-[3,5-dimethyl-4-(3-methylamino-propoxy)-phenyl]-1-(3-ethyl-5,5-dimethyl-4,5,6,7-tetrahydro-benzo[c]thiophen-1-yl)-propan-1-one;

N-(3-{4-[3-(3-ethyl-5,5-dimethyl-4,5,6,7-tetrahydro-benzo[c]thiophen-1-yl)-3-oxo-propyl]-2,6-dimethyl-phenoxy}-propyl)-methanesulfonamide;

N-(3-{4-[3-(3-ethyl-5,5-dimethyl-4,5,6,7-tetrahydro-benzo[c]thiophen-1-yl)-3-oxo-propyl]-2,6-dimethyl-phenoxy}-propyl)-2-hydroxy-acetamide;

N-(3-{4-[3-(3-ethyl-5,5-dimethyl-4,5,6,7-tetrahydro-benzo[c]thiophen-1-yl)-3-oxo-propyl]-2,6-dimethyl-phenoxy}-propyl)-2-methylamino-acetamide;

N-(3-{2-ethyl-4-[3-(3-ethyl-5,5-dimethyl-4,5,6,7-tetrahydro-benzo[c]thiophen-1-yl)-3-oxo-propyl]-6-methyl-phenoxy}-propyl)-2-hydroxy-acetamide;

N-(3-{2-ethyl-4-[3-(3-ethyl-5,5-dimethyl-4,5,6,7-tetrahydro-benzo[c]thiophen-1-yl)-3-oxo-propyl]-6-methyl-phenoxy}-propyl)-2-methylamino-acetamide;

N-(3-{2,6-diethyl-4-[3-(3-ethyl-5,5-dimethyl-4,5,6,7-tetrahydro-benzo[c]thiophen-1-yl)-3-oxo-propyl]-phenoxy}-propyl)-2-hydroxy-acetamide;

N-(3-{2-chloro-4-[3-(3-ethyl-5,5-dimethyl-4,5,6,7-tetrahydro-benzo[c]thiophen-1-yl)-3-oxo-propyl]-6-methoxy-phenoxy}-propyl)-2-hydroxy-acetamide;

3-[4-(3-Amino-propoxy)-2-methoxy-phenyl]-1-(3-ethyl-5,5-dimethyl-4,5,6,7-tetrahydro-benzo[c]thiophen-1-yl)-propan-1-one;

N-(3-{4-[3-(3-ethyl-5,5-dimethyl-4,5,6,7-tetrahydro-benzo[c]thiophen-1-yl)-3-oxo-propyl]-3-methoxy-phenoxy}-propyl)-methanesulfonamide;

N-(3-{4-[3-(3-ethyl-5,5-dimethyl-4,5,6,7-tetrahydro-benzo[c]thiophen-1-yl)-3-oxo-propyl]-3-methoxy-phenoxy}-propyl)-2-hydroxy-acetamide;

1-(3-ethyl-5,5-dimethyl-4,5,6,7-tetrahydro-benzo[c]thiophen-1-yl)-3-[4-(2-hydroxy-3-methylamino-propoxy)-3,5-dimethyl-phenyl]-propan-1-one;

3-[4-(3-Amino-2-hydroxy-propoxy)-3-ethyl-5-methyl-phenyl]-1-(3-ethyl-5,5-dimethyl-4,5,6,7-tetrahydro-benzo[c]thiophen-1-yl)-propan-1-one;

N-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-methanesulfonamide;
ethanesulfonic acid (3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-amide;
methanesulfamic acid (3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-amide;
N-(3-{2-ethyl-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-methanesulfonamide;
ethanesulfonic acid (3-{2-ethyl-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-amide;
methanesulfamic acid (3-{4-[3-(3-ethyl-5,5-dimethyl-4,5,6,7-tetrahydro-benzo[c]thiophen-1-yl)-3-oxo-propyl]-2-ethyl-6-methyl-phenoxy}-2-hydroxy-propyl)-amide;
N-(3-{2-chloro-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-methanesulfonamide;
N-(3-{2-chloro-4-[3-(3-ethyl-5,5-dimethyl-4,5,6,7-tetrahydro-benzo[c]thiophen-1-yl)-3-oxo-propyl]-6-methoxy-phenoxy}-2-hydroxy-propyl)-methanesulfonamide;
N-(3-{4-[3-(3-ethyl-5,5-dimethyl-4,5,6,7-tetrahydro-benzo[c]thiophen-1-yl)-3-oxo-propyl]-3-methoxy-phenoxy}-2-hydroxy-propyl)-methanesulfonamide;
(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propylamino)-acetic acid methyl ester;
3-(3-{4-[3-(3-ethyl-5,5-dimethyl-4,5,6,7-tetrahydro-benzo[c]thiophen-1-yl)-3oxo-propyl]-2,6-dimethyl-phenoxy}-2-hydroxy-propylamino)-propionic acid methyl ester;
1-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-azetidine-3-carboxylic acid methyl ester;
(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propylamino)-acetic acid ethyl ester;
3-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propylamino)-propionic acid ethyl ester;
1-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-azetidine-3-carboxylic acid ethyl ester;
1-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-azetidine-3-carboxylic acid;
1-(3-ethyl-5,5-dimethyl-4,5,6,7-tetrahydro-benzo[c]thiophen-1-yl)-3-{3-ethyl-4-[2-hydroxy-3-(2-hydroxy-ethylamino)-propoxy]-5-methyl-phenyl}-propan-1-one;
N-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-2-hydroxy-acetamide;
N-(3-{2-ethyl-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-2-hydroxy-acetamide;
N-(3-{2,6-diethyl-4-[3-(3-ethyl-5,5-dimethyl-4,5,6,7-tetrahydro-benzo[c]thiophen-1-yl)-3-oxo-propyl]-phenoxy}-2-hydroxy-propyl)-2-hydroxy-acetamide;
N-(3-{2-chloro-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-2-hydroxy-acetamide;
N-(3-{2-chloro-4-[3-(3-ethyl-5,5-dimethyl-4,5,6,7-tetrahydro-benzo[c]thiophen-1-yl)-3-oxo-propyl]-6-methoxy-phenoxy}-2-hydroxy-propyl)-2-hydroxy-acetamide;
N-(3-{4-[3-(3-ethyl-5,5-dimethyl-4,5,6,7-tetrahydro-benzo[c]thiophen-1-yl)-3-oxo-propyl]-3-methoxy-phenoxy}-2-hydroxy-propyl)-2-hydroxy-acetamide;
N-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-2-methylamino-acetamide;
N-(3-{4-[3-(3-ethyl-5,5-dimethyl-4,5,6,7-tetrahydro-benzo[c]thiophen-1-yl)-3-oxo-propyl]-2,6-dimethyl-phenoxy}-2-hydroxy-propyl)-3-methylamino-propionamide;
N-(3-{2-ethyl-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-2-methylamino-acetamide;
N-(3-{2-ethyl-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-3-methylamino-propionamide;
N-(3-{2,6-diethyl-4-[3-(3-ethyl-5,5-dimethyl-4,5,6,7-tetrahydro-benzo[c]thiophen-1-yl)-3-oxo-propyl]-phenoxy}-2-hydroxy-propyl)-2-methylamino-acetamide;
N-(3-{2-chloro-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-2-methylamino-acetamide;
N-(3-{2-chloro-4-[3-(3-ethyl-5,5-dimethyl-4,5,6,7-tetrahydro-benzo[c]thiophen-1-yl)-3-oxo-propyl]-6-methyl-phenoxy}-2-hydroxy-propyl)-3-methylamino-propionamide;
N-(3-{2-chloro-4-[3-(3-ethyl-5,5-dimethyl-4,5,6,7-tetrahydro-benzo[c]thiophen-1-yl)-3-oxo-propyl]-6-methoxy-phenoxy}-2-hydroxy-propyl)-2-methylamino-acetamide;
N-(3-{4-[3-(3-ethyl-5,5-dimethyl-4,5,6,7-tetrahydro-benzo[c]thiophen-1-yl)-3-oxo-propyl]-3-methoxy-phenoxy}-2-hydroxy-propyl)-2-methylamino-acetamide;
N-(3-{4-[3-(3-ethyl-5,5-dimethyl-4,5,6,7-tetrahydro-benzo[c]thiophen-1-yl)-3-oxo-propyl]-3-methoxy-phenoxy}-2-hydroxy-propyl)-3-methylamino-propionamide;
3-[4-(2,3-dihydroxy-propyl)-3,5-dimethyl-phenyl]-1-(3-ethyl-5,5-dimethyl-4,5,6,7-tetrahydro-benzo[c]thiophen-1-yl)-propan-1-one;
3-{4-[3-(3-ethyl-5,5-dimethyl-4,5,6,7-tetrahydro-benzo[c]thiophen-1-yl)-3-oxo-propyl]-2,6-di methyl-phenyl}-propionamide;
3-{4-[3-(3-ethyl-5,5-dimethyl-4,5,6,7-tetrahydro-benzo[c]thiophen-1-yl)-3-oxo-propyl]-2,6-dimethyl-phenyl}-N-(2-hydroxy-ethyl)-propionamide;
3-{4-[3-(3-ethyl-5,5-dimethyl-4,5,6,7-tetrahydro-benzo[c]thiophen-1-yl)-3-oxo-propyl]-2,6-dimethyl-phenyl}-N-(3-hydroxy-propyl)-propionamide;
3-{4-[3-(3-ethyl-5,5-dimethyl-4,5,6,7-tetrahydro-benzo[c]thiophen-1-yl)-3-oxo-propyl]-2,6-dimethyl-phenyl}-N-(2-hydroxy-1-hydroxymethyl-ethyl)-propionamide;
(3-{4-[3-(3-ethyl-5,5-dimethyl-4,5,6,7-tetrahydro-benzo[c]thiophen-1-yl)-3-oxo-propyl]-2,6-dimethyl-phenyl}-propionylamino)-acetic acid methyl ester;
3-(3-{4-[3-(3-ethyl-5,5-dimethyl-4,5,6,7-tetrahydro-benzo[c]thiophen-1-yl)-3oxo-propyl]-2,6-dimethyl-phenyl}-propionylamino)-propionic acid methyl ester;
3-(3-{4-[3-(3-ethyl-5,5-dimethyl-4,5,6,7-tetrahydro-benzo[c]thiophen-1-yl)-3-oxo-propyl]-2,6-dimethyl-phenyl}-propionylamino)-propionic acid;
3-{2-ethyl-4-[3-(3-ethyl-5,5-dimethyl-4,5,6,7-tetrahydro-benzo[c]thiophen-1-yl)-3-oxo-propyl]-6-methyl-phenyl}-N-(2-hydroxy-ethyl)-propionamide;
3-{2-ethyl-4-[3-(3-ethyl-5,5-dimethyl-4,5,6,7-tetrahydro-benzo[c]thiophen-1-yl)-3-oxo-propyl]-6-methyl-phenyl}-N-(2-hydroxy-1-hydroxymethyl-ethyl)-propionamide;

(3-{2-ethyl-4-[3-(3-ethyl-5,5-dimethyl-4,5,6,7-tetrahydro-benzo[c]thiophen-1-yl)-3-oxo-propyl]-6-methyl-phenyl}-propionylamino)-acetic acid;

1-(3-ethyl-5,5-dimethyl-4,5,6,7-tetrahydro-benzo[c]thiophen-1-yl)-3-[4-(3-hydroxy-propyl)-3,5-dimethyl-phenyl]-propan-1-one;

1-(3-ethyl-5,5-dimethyl-4,5,6,7-tetrahydro-benzo[c]thiophen-1-yl)-3-[ethyl-4-(3-hydroxy-propyl)-5-methyl-phenyl]-propan-1-one;

N-(3-{4-[3-(3-ethyl-5,5-dimethyl-4,5,6,7-tetrahydro-benzo[c]thiophen-1-yl)-3-oxo-propyl]-2,6-dimethyl-phenyl}-propyl)-2-hydroxy-acetamide;

N-(3-{4-[3-(3-ethyl-5,5-dimethyl-4,5,6,7-tetrahydro-benzo[c]thiophen-1-yl)-3-oxo-propyl]-2,6-dimethyl-phenyl}-propyl)-3-hydroxy-propionamide;

N-(3-{4-[3-(3-ethyl-5,5-dimethyl-4,5,6,7-tetrahydro-benzo[c]thiophen-1-yl)-3-oxo-propyl]-2,6-dimethyl-phenyl}-propyl)-2-methylamino-acetamide;

N-(3-{4-[3-(3-ethyl-5,5-dimethyl-4,5,6,7-tetrahydro-benzo[c]thiophen-1-yl)-3oxo-propyl]-2,6-dimethyl-phenyl}-propyl)-3-methylamino-propionamide;

N-(3-{2-ethyl-4-[3-(3-ethyl-5,5-dimethyl-4,5,6,7-tetrahydro-benzo[c]thiophen-1-yl)-3-oxo-propyl]-6-methyl-phenyl}-propyl)-2-hydroxy-acetamide;

N-(3-{2-ethyl-4-[3-(3-ethyl-5,5-dimethyl-4,5,6,7-tetrahydro-benzo[c]thiophen-1-yl)-3-oxo-propyl]-6-methyl-phenyl}-propyl)-3-hydroxy-propionamide;

N-(3-{2-ethyl-4-[3-(3-ethyl-5,5-dimethyl-4,5,6,7-tetrahydro-benzo[c]thiophen-1-yl)-3-oxo-propyl]-6-methyl-phenyl}-propyl)-2-methylamino-acetamide;

N-(3-{2-ethyl-4-[3-(3-ethyl-5,5-dimethyl-4,5,6,7-tetrahydro-benzo[c]thiophen-1-yl)-3-oxo-propyl]-6-methyl-phenyl}-propyl)-3-methylamino-propionamide;

N-(2-amino-ethyl)-4-[3-(3-ethyl-5,5-dimethyl-4,5,6,7-tetrahydro-benzo[c]thiophen-1-yl)-3-oxo-propyl]-benzene-sulfonamide;

N-{4-[3-(3-ethyl-5,5-dimethyl-4,5,6,7-tetrahydro-benzo[c]thiophen-1-yl)-3-oxo-propyl]-2,6-dimethyl-phenyl}-2-hydroxy-acetamide;

N-(3-{4-[5-(3-ethyl-5,5-dimethyl-4,5,6,7-tetrahydro-benzo[c]thiophen-1-yl)-[1,2,4]oxadiazol-3-yl]-2,6-dimethyl-phenoxy-2-hydroxy-propyl)-2-hydroxy-acetamide;

3-{2-ethyl-4-[5-(3-ethyl-5,5-dimethyl-4,5,6,7-tetrahydro-benzo[c]thiophen-1-yl)-[1,2,4]oxadiazol-3-yl]-6-methyl-phenyl}-N-(2-hydroxy-ethyl)-propionamide;

1-(3-ethyl-5,5-dimethyl-4,5,6,7-tetrahydro-benzo[c]thiophen-1-yl)-2-(2-methoxy-phenylamino)-ethanone;

1-(3-ethyl-5,5-dimethyl-4,5,6,7-tetrahydro-benzo[c]thiophen-1-yl)-2-[4-(2-hydroxy-ethyl)-phenylamino]-ethanone;

1-(5,5-diethyl-3-methyl-4,5,6,7-tetrahydro-benzo[c]thiophen-1-yl)-3-[4-((S)-2,3-dihydroxy-propoxy)-3,5-dimethyl-phenyl]-propan-1-one;

N-(3-{4-[3-(5,5-diethyl-3-methyl-4,5,6,7-tetrahydro-benzo[c]thiophen-1-yl)-3-oxo-propyl]-2,6-dimethyl-phenoxy}-2-hydroxy-propyl)-2-hydroxy-acetamide;

3-[4-(2,3-dihydroxy-propoxy)-3,5-dimethyl-phenyl]-1-(3-ethyl-5-methyl-4,5,6,7-tetrahydro-benzo[c]thiophen-1-yl)-propan-1-one;

3-[4-(2,3-dihydroxy-propoxy)-3,5-dimethyl-phenyl]-1-(3-ethyl-5,5-ethylene-4,5,6,7-tetrahydro-benzo[c]thiophen-1-yl)-propan-1-one;

N-(3-{4-[5-(5,5-ethylene-4,5,6,7-tetrahydro-benzo[c]thiophen-1-yl)-[1,2,4]oxadiazol-3-yl]-2,6-dimethyl-phenoxy-2-hydroxy-propyl)-2-hydroxy-acetamide;

3-[4-(2,3-dihydroxy-propoxy)-3,5-dimethyl-phenyl]-1-(5,5-dimethyl-3-trifluoromethyl-4,5,6,7-tetrahydro-benzo[c]thiophen-1-yl)-propan-1-one;

1-(5,5-dimethyl-3-trifluoromethyl-4,5,6,7-tetrahydro-benzo[c]thiophen-1-yl)-3-[4-(2-hydroxy-3-methoxy-propoxy)-3,5-dimethyl-phenyl]-propan-1-one;

1-(5,5-dimethyl-3-trifluoromethyl-4,5,6,7-tetrahydro-benzo[c]thiophen-1-yl)-3-[3-ethyl-4-(2-hydroxy-ethoxy)-5-methyl-phenyl]-propan-1-one;

1-(5,5-dimethyl-3-trifluoromethyl-4,5,6,7-tetrahydro-benzo[c]thiophen-1-yl)-3-[3-ethyl-4-(2-hydroxy-propoxy)-5-methyl-phenyl]-propan-1-one;

3-[4-((S)-2,3-dihydroxy-propoxy)-3-ethyl-5-methyl-phenyl]-1-(5,5-dimethyl-3-trifluoromethyl-4,5,6,7-tetrahydro-benzo[c]thiophen-1-yl)-propan-1-one;

3-[4-(2,3-dihydroxy-propoxy)-3-ethyl-5-methyl-phenyl]-1-(5,5-dimethyl-3-trifluoromethyl-4,5,6,7-tetrahydro-benzo[c]thiophen-1-yl)-propan-1-one;

N-(3-{4-[3-(5,5-dimethyl-3-trifluoromethyl-4,5,6,7-tetrahydro-benzo[c]thiophen-1-yl)-3-oxo-propyl]-2-ethyl-6-methyl-phenoxy}-2-hydroxy-propyl)-2-hydroxy-acetamide;

N-(3-{4-[3-(5,5-dimethyl-3-trifluoromethyl-4,5,6,7-tetrahydro-benzo[c]thiophen-1-yl)-3-oxo-propyl]-2-ethyl-6-methyl-phenoxy}-2-hydroxy-propyl)-3-hydroxy-propionamide;

N-(3-{4-[3-(5,5-dimethyl-3-trifluoromethyl-4,5,6,7-tetrahydro-benzo[c]thiophen-1-yl)-3-oxo-propyl]-2-ethyl-6-methyl-phenoxy}-2-hydroxy-propyl)-2-methylamino-acetamide;

N-(3-{4-[3-(5,5-dimethyl-3-trifluoromethyl-4,5,6,7-tetrahydro-benzo[c]thiophen-1-yl)-3-oxo-propyl]-2,6-diethyl-phenoxy}-2-hydroxy-propyl)-2-hydroxy-acetamide;

N-(3-{4-[3-(5,5-dimethyl-3-trifluoromethyl-4,5,6,7-tetrahydro-benzo[c]thiophen-1-yl)-3-oxo-propyl]-2,6-diethyl-phenoxy}-2-hydroxy-propyl)-3-hydroxy-propionamide;

3-[4-(2,3-dihydroxy-propylamino)-3,5-dimethyl-phenyl]-1-(5,5-dimethyl-3-trifluoromethyl-4,5,6,7-tetrahydro-benzo[c]thiophen-1-yl)-propan-1-one;

3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-N-(2-hydroxy-1-hydroxymethyl-ethyl)-propionamide;

N-(2,3-dihydroxy-propyl)-3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionamide;

(3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionylamino)-acetic acid methyl ester;

(3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionylamino)-acetic acid;

1-(5,5-dimethyl-3-trifluoromethyl-4,5,6,7-tetrahydro-benzo[c]thiophen-1-yl)-3-[3-ethyl-4-(3-hydroxy-propyl)-5-methyl-phenyl]-propan-1-one;

N-(3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propyl)-2-hydroxy-acetamide;

N-(3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propyl)-3-hydroxy-propionamide;

1-(5,5-dimethyl-3-trifluoromethyl-4,5,6,7-tetrahydro-benzo[c]thiophen-1-yl)-2-(2-methoxy-phenylamino)-ethanone; and 1-(5,5-dimethyl-3-trifluoromethyl-4,5,6,7-tetrahydro-benzo[c]thiophen-1-yl)-2-[4-(2-hydroxy-ethyl)-phenylamino]-ethanone.

A further aspect of the invention relates to novel compounds of the Formula (II)

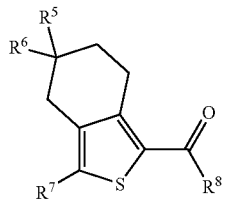

Formula (II)

wherein
$R^5$, $R^6$ and $R^7$ are as defined for Formula (I) above; and
$R^8$ represents hydroxy, $C_{1-5}$-alkoxy, or methyl;
and configurational isomers such as optically pure enantiomers, mixtures of enantiomers such as racemates, diastereomers, mixtures of diastereomers, diastereomeric racemates, and mixtures of diastereomeric racemates, as well as salts and solvent complexes of such compounds, and morphological forms.

A further aspect of the invention relates to novel compounds of the Formula (III),

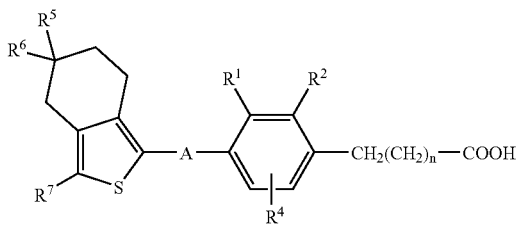

Formula (III)

wherein A, $R^1$, $R^2$, $R^4$, $R^5$, $R^6$, $R^7$ and n are as defined for Formula (I) above;
and configurational isomers such as optically pure enantiomers, mixtures of enantiomers such as racemates, diastereomers, mixtures of diastereomers, diastereomeric racemates, and mixtures of diastereomeric racemates, as well as salts and solvent complexes of such compounds, and morphological forms.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Preferably, the diseases or disorders to be prevented or treated with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a patient a pharmaceutically active amount of a compound of Formula (I).

Furthermore, the compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

Still a further object of the present invention is a process to prepare a pharmaceutical composition comprising a compound of the Formula (I) by mixing one or more active ingredients with inert excipients in a manner known per se.

The present invention also relates to the use of a compound of Formula (I) for the preparation of a pharmaceutical composition, optionally for use in combination with one or several immunomodulating agents, for the prevention and/or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I), as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

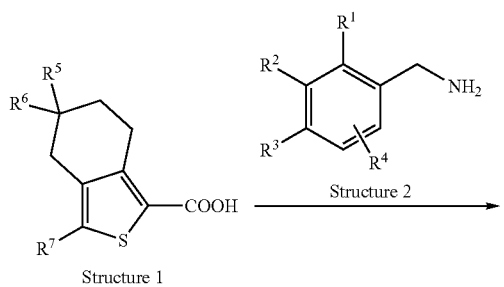

Structure 1

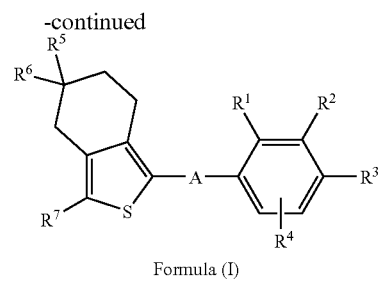

Formula (I)

In case A represents —CO—CH=CH—, the compounds of Formula (I) may be prepared by reacting a compound of Structure 5 with a compound of Structure 6 in the presence of a base or an acid. Compounds of Formula (I) wherein A represents —CO—CH$_2$—CH$_2$— may also be prepared by reacting a compound of Formula (I) wherein A represents —CO—CH=CH— (Structure 7) with hydrogen in the presence of a catalyst such as Pd/C, Pt/C, PtO$_2$, etc. in a solvent such as ethanol, methanol, THF, etc.

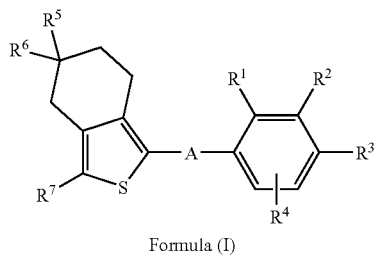

Formula (I)

In case A represents —CONH—CH$_2$—, the compounds of the Formula (I) may be prepared by reacting a compound of Structure 1 with a compound of Structure 2 in the presence of an activating agent such as EDC, DCC, HOBt, BOP, PyBOP, BOP—Cl, etc. in a solvent such as THF, dioxane, DMF, DCM, acetonitrile, etc.

In case A represents —CO—CH$_2$—CH$_2$—, the compounds of Formula (I) may be prepared by reacting a compound of Structure 3 with a compound of Structure 4 under Grignard conditions, preferably at temperatures below rt. The Grignard reagent of Structure 4 is prepared according to standard methodology. The functional groups present in the residues R$^1$ to R$^4$ may require temporary protection or may even be introduced in additional steps that follow the Grignard reaction. The Weinreb amide compound of Structure 3 is prepared by treating a compound of Structure 1 with N,O-dimethylhydroxylamine hydrochloride in the presence of a coupling reagent such as EDC, DCC, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, Current Organic Chemistry 7 (2003), 967-993).

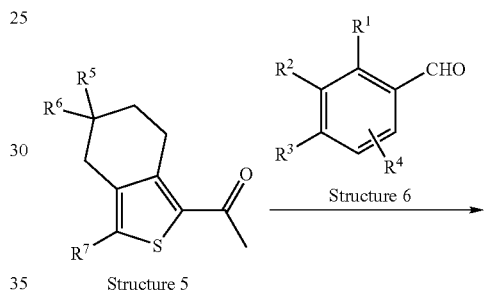

Structure 5

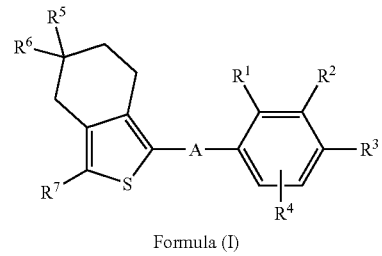

Formula (I)

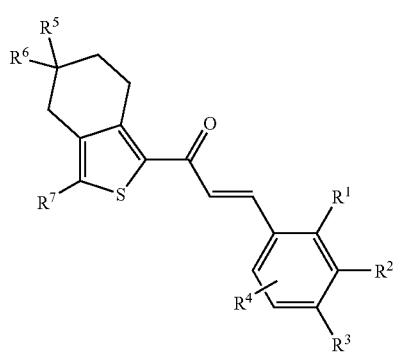

Structure 7

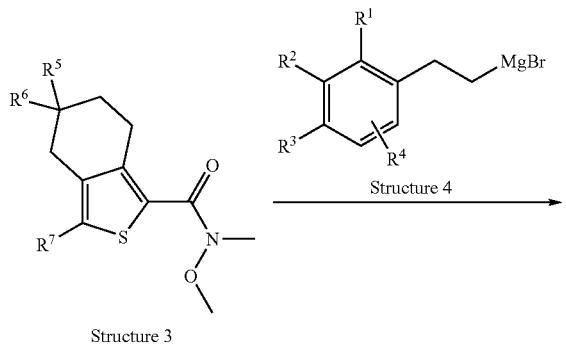

Structure 3

Compounds of the Formula (I) wherein A represents —CO—CH$_2$—O— or —CO—CH$_2$—NH— may be prepared by reacting a compound of Structure 8 with a compound of Structure 9 in the presence or absence of a base such as $K_2CO_3$, $Na_2CO_3$, K-tert.butoxide, NaOH, NaH, triethylamine, DIPEA, etc. in a solvent such as acetone, DMF, THF, dioxane, etc. or mixtures thereof. The compounds of Structure 8 can be prepared by reacting a compound of Structure 5 with a brominating agent such as phenyltrimethylammoniumbromid dibromide, benzyltrimethylammonium-tribromid, triphenylphosphine dibromide, etc. in a solvent such as DCM, chloroform, THF, diethyl ether, methanol, ethanol, etc., or mixtures thereof.

Structure 8

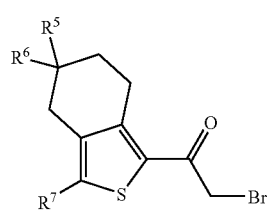

Structure 9

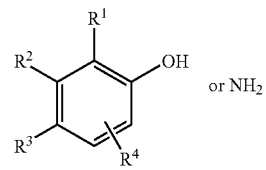

or $NH_2$

Compounds of Structure 5 may be prepared by treating a compound of Structure 1 with MeLi in a solvent such as diethyl ether, THF, dioxane, at temperatures between −20 and 50° C. Alternatively, a compound of Structure 5 may be prepared by reacting a compound of Structure 3 with methylmagnesium bromide.

Compounds of Formula (I), wherein Formula (I) represents a 5-thiophen-2-yl-[1,2,4]oxadiazole derivative, are prepared by reacting a compound of Structure 10 in a solvent such as xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, etc.) (Lit: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

Structure 10

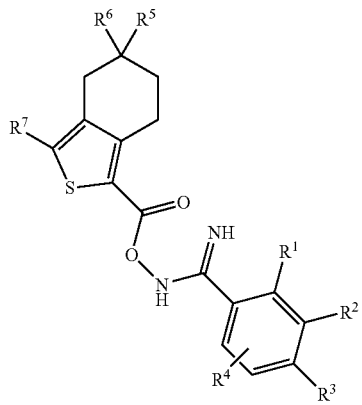

Compounds of Structure 10 may be prepared by reacting a compound of Structure 1 with a compound of Structure 11 in a solvent such as DMF, THF, etc. in the presence or absence of one or more coupling agents such as TBTU, DCC, EDC, HBTU, HOBt, CDI, etc. and in the presence or absence of a base such as triethylamine, Hünig's base, NaH, $K_2CO_3$, etc. (Lit: e.g. A. Hamze, J.-F. Hernandez, P. Fulcrand, J. Martinez, *J. Org. Chem.* 68 (2003) 7316-7321; and the literature cited above).

Structure 1

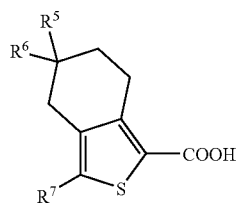

Structure 11

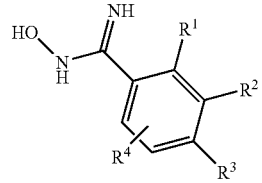

Compounds of Structure 11 may be prepared by reacting a compound of Structure 12 with hydroxylamine or one of its salts in a solvent such as methanol, ethanol, pyridine, etc. in the presence or absence of a base such as $Na_2CO_3$, $K_2CO_3$, triethylamine, etc. (Lit: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292).

Structure 12

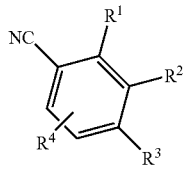

Structure 13

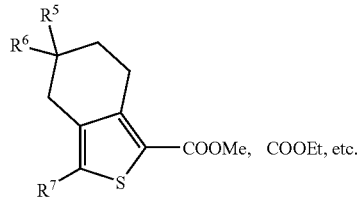

Depending on the nature of the functionalities present in the residues $R^1$ to $R^4$ in Structures 2, 4, 6, 9 and 12, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley N.Y., 1991; P. J. Kocienski, Protecting Groups, Thieme Stuttgart, 1994). Alternatively, the desired residues $R^1$ to $R^4$ may also be introduced in later steps that follow the reaction of a compound of Structure 1, 3, 5 or 8 with a suitable precursor of a compound of Structure 2, 4, 6, 9 and 11, respectively. The compounds of Structure 2, 4, 6, 9 and 12 or their precursors are either commercially available or are prepared according to procedures known to a person skilled in the art.

Compounds of Formula (I), wherein $R^3$ is —CH$_2$—(CH$_2$)$_n$—CONR$^{31}$R$^{32}$ can be prepared by reacting a carboxylic acid of Formula (III),

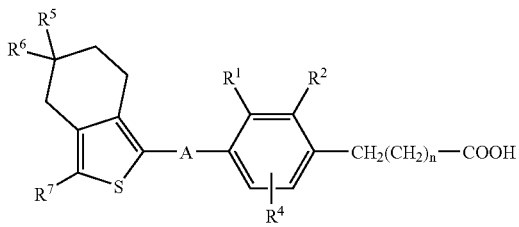

wherein A, $R^1$, $R^2$, $R^4$, $R^5$, $R^6$, $R^7$ and n are as defined for Formula (I) above, with an amine HNR$^{31}$R$^{32}$ in the presence of an activating agent such as EDC, DCC, HOBt, BOP, PyBOP, BOP—Cl, etc. in a solvent such as THF, dioxane, DMF, DCM, acetonitrile, etc. Compounds of Formula (III) can be prepared as described above from compounds of Structure 2, 6, 9 or 12, wherein $R^3$ is —CH$_2$—(CH$_2$)$_n$—COOH. Compounds of Structure 12, wherein $R^3$ is —CH$_2$—(CH$_2$)$_n$—COOH can be prepared from compounds of Structure 6, wherein $R^3$ is —CH$_2$—(CH$_2$)$_n$—COOH by methods well known in the art. Compounds of Structure 6, wherein $R^3$ is —CH$_2$—(CH$_2$)$_n$—COOH can be prepared by well known methods e.g. via a sequence of Heck reaction followed by catalytic hydrogenation from compounds of Structure 6, wherein $R^3$ is —O—SO$_2$—CF$_3$, bromo or iodo. Compounds of Structure 6, wherein $R^3$ is —O—SO$_2$—CF$_3$, bromo or iodo are either known or can be prepared according to known procedures.

Compounds of Structure 1 may be prepared by reacting a compound of Structure 13 with an aqueous base such as aq. NaOH, aq. LiOH, aq. KOH, etc. or an acid such as aq. HCl, TFA, etc. in a solvent such as water, ethanol, methanol, THF, etc. or mixtures thereof.

The compounds of Structure 13 are prepared by treating a compound of Structure 14 with a non aqueous base such as NaOMe, NaOEt, KO-tert.-Bu, DBU, etc. in a solvent such as methanol, ethanol, THF, DMF, etc. or mixtures thereof, preferably at elevated temperatures.

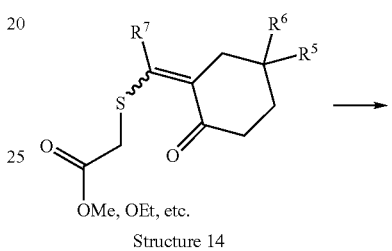

Structure 14

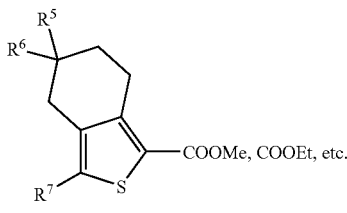

Structure 13

The compounds of Structure 14 are prepared by treating a compound of Structure 15 with a 2-mercaptoacetic acid ester in the presence of a base such a NaH, NaOEt, NaOMe, K tert.-butoxide, etc. in THF, dioxane, DMF, ethanol, methanol, etc. or mixtures thereof. In addition, the compounds of Structure 1 may also be prepared in a one-pot three step procedure starting from a compound of Structure 15 following the above reaction sequence.

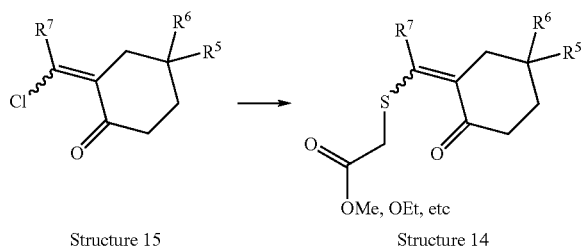

Structure 15            Structure 14

The compounds of Structure 15 are prepared by reacting a compound of Structure 16 with a chlorinating agent such as oxalylchloride in a solvent such as DCM, CHCl$_3$, THF, etc. (Lit. e.g. R. E. Mewshaw, Richard E. *Tetrahedron Lett.* 30 (1989), 3753-3756; F. A. Lakhvich, T. S. Khlebnikova, A. A. Akhrem, *Zhurnal Organicheskoi Khimii* 25 (1989), 2541-2549).

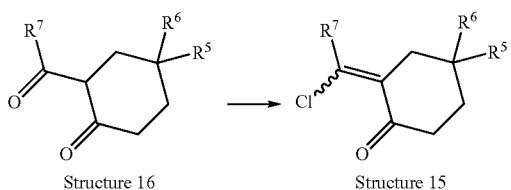

Structure 16    Structure 15

The compounds of Structure 16 may be prepared by acylating a compound of Structure 17 with an appropriate acylating agent such as ethy or methyl formate, methyl or ethyl acetate, methyl or ethyl propionate, chloroformate, acetyl chloride, etc. in the presence of a base such as K-tert. butylate, NaOMe, NaH, LDA, etc. in a solvent such as THF, toluene, EtOH etc. at temperatures between 0 and 60° C. (Lit. e.g. Ch. Kashima, S. Shibata, H. Yokoyama, T. Nishio, *Journal of Heterocyclic Chemistry* 40 (2003), 773-782; I. Yavari, Issa; M. Bayat, *Tetrahedron* 59 (2003), 2001-2005; J. P. Konopelski, J. Lin, P. J. Wenzel, H. Deng, G. I. Elliott, B. S. Gerstenberger, *Organic Letters* 4 (2002) 4121-4124; C. Wiles, P. Watts, S. J. Haswell, E. Pombo-Villar, *Tetrahedron Letters* 43 (2002), 2945-2948; R. Faure, A. Frideling, J.-P. Galy, I. Alkorta, J. Elguero, *Heterocycles* 57 (2002) 307-316; via imine: M. Hammadi, D. Villemin, *Synthetic Communications* 26 (1996) 2901-2904).

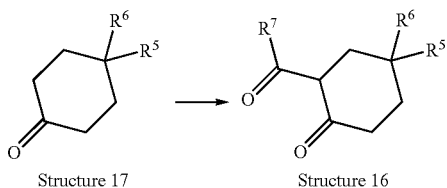

Structure 17    Structure 16

The compounds of Structure 17 are either commercially available or are prepared according to procedures known to a person skilled in the art (Lit. e.g. M. E. Flaugh, T. A. Crowell, D. S. Farlow, *Journal of Organic Chemistry* 45 (1980) 5399-5400; A. M. Badger, M. J. Dimartino, C. K. Mirabelli, E. N. Cheeseman, J. W. Dorman, D. H. Picker, D. A. Schwartz, Eur. Pat. Appl. EP 310321 A2 (1989); N. R. Natale, R. O. Hutchins, *Organic Preparations and Procedures International* 9 (1977), 103-108; L. M. Rice, B. S. Sheth, J. W. Wheeler, *Journal of Heterocyclic Chemistry* 10 (1973) 731-735).

The compounds of Structure 1 wherein $R^7$ represents an alkyl or an hydroxymethyl group may also be prepared from a compound of Structure 1 wherein $R^7$ represents hydrogen by reacting the latter compound with an excess of a strong base such as n-BuLi, tert.-BuLi, LDA in a solvent such as THF, diethyl ether, etc. followed by the appropriate alkylating agent (e.g. methyl, ethyl, propyl iodide, formaldehyde, Lit. e.g. W.-D. Liu, C.-C. Chi, I.-F. Pai, A.-T. Wu, W.-S. Chung, *Journal of Organic Chemistry*, 67 (2002) 9267-9275; D. W. Knight, A. P. Nott, *Tetrahedron Letters* 21 (1980) 5051-5054; R. Raap, *Canadian Journal of Chemistry* 49 (1971) 2155-2157). The compounds of Structure 1 wherein $R^7$ represents hydroxymethyl, methoxymethyl, methoxy, hydroxycarbonyl, amino, or mono- or di-($C_{1-5}$-alkyl)amino may be prepared from a compound of Structure 18 following procedures known to a person skilled in the art (Lit. e.g. F. Wuerthner, S. Yao, T. Debaerdemaeker, R. Wortmann, *J. Am. Chem. Soc.* 124 (2002) 9431-9447). A compound of Structure 18 may be prepared from a compound of Structure 1 wherein $R^7$ represents hydrogen e.g. by treating a compound of Structure 1 with $Br_2$ in acetic acid. (Lit. e.g. G. A. Diaz-Quijada, N. Weinberg, S. Holdcroft, B. M. Pinto, *Journal of Physical Chemistry A* 106 (2002) 1266-1276; G. Karminski-Zamola, J. Dogan, M. Bajic, J. Blazevic, M. Malesevic, Heterocycles 38 (1994), 759-67; R. H. Mitchell, Y. Chen, J. Zhang, *Organic Preparations and Procedures International* 29 (1997) 715-719; F. Wuerthner, S. Yao, T. Debaerdemaeker, R. Wortmann, *J. Am. Chem. Soc.* 124 (2002) 9431-9447; K. Yamagata, Y. Tomioka, M. Yamazaki, T. Matsuda, K. Noda, *Chemical & Pharmaceutical Bulletin* 30 (1982) 4396-401).

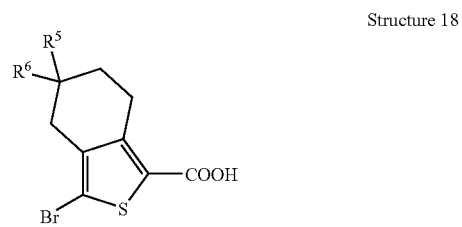

Structure 18

EXAMPLES

The following examples illustrate the invention but do not at all limit the scope thereof.

All temperatures are stated in degrees Celsius. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (column: X-terra RP18, 50×19 mm, 5 µm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

Abbreviations (As Used Herein)
aq. aqueous
atm atmosphere
BOC tert-butyloxycarbonyl
BOP (benzotriazol-1-yloxy)-tris-(dimethylamino)-phosphonium hexafluorophosphate
BOP—Cl bis-(2-oxo-3-oxazolidinyl)-phosphinic acid chloride
BSA bovine serum albumin
Bu butyl
CC column chromatography
CDI carbonyl diimidazole
DBU 1,8-diazabicylo[5.4.0]undec-7-en
DCC dicyclohexyl carbodiimide
DCM dichloromethane
DDQ 2,3-dichloro-5,6-dicyano-p-benzoquinone
DIPEA diisopropyl-ethylamine, Hünig's base, ethyl-diisopropylamine
DMF dimethylformamide
DMSO dimethylsulfoxide
DPPP 1,3-bis-(diphenylphosphino)-propane EA ethyl acetate
EDC N-(3-dimethylaminopropyl)-N'-ethyl-carbodiimide
eq. equivalent(s)
Et ethyl
Ex. example
h hour(s)
HBTU O-(benzotriazol-1-yl)-N,N,N',N'-tetramethyluronium hexafluorophosphate
HOBt 1-hydroxybenzotriazole
HPLC high performance liquid chromatography
HV high vacuum conditions
LC-MS liquid chromatography-mass spectrometry
LDA lithiumdiisopropylamide
Me methyl
min minute(s)
MPLC medium pressure liquid chromatography
NMO N-methyl-morpholine-N-oxide
OAc acetate
prep. preparative
PyBOP benzotriazol-1-yl-oxy-tris-pyrolidino-phosphonium-hexafluoro-phosphat
rt room temperature
sat. saturated
S1P sphingosine 1-phosphate
TBME tert.-Butylmethyl ether
TBTU 2-(1H-benzotriazole-1-yl)-1,2,3,3-tetramethyluronium tetrafluoroborate
TFA trifluoroacetic acid
THF tetrahydrofuran
TLC thin layer chromatography
$t_R$ retention time Methanesulfonic Aid
2,2-dimethyl-[1,3]dioxan-5-ylmethyl ester

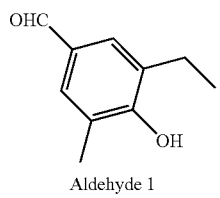

The title compound is prepared following the procedures given in B. Xu, A. Stephens, G. Kirschenheuter, A. F. Greslin, X. Cheng, J. Sennelo, M. Cattaneo, M. L. Zighetti, A. Chen, S.-A. Kim, H. S. Kim, N. Bischofberger, G. Cook, K. A. Jacobson, *J. Med. Chem.* 45 (2002) 5694-5709.

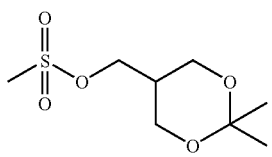

Aldehyde 1

3-Ethyl-4-hydroxy-5-methyl-benzaldehyde is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

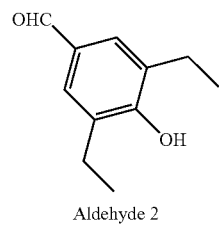

Aldehyde 2

3,5-Diethyl-4-hydroxy-benzaldehyde is prepared from commercially available 2,6-diethylaniline following literature procedures (R. Breslow, K. Groves, M. U. Mayer, *J. Am. Chem. Soc.* 124 (2002) 3622-3635, and literature cited for Aldehyde 1); $^1$H NMR (CDCl$_3$): δ 9.85 (s, 1H), 7.57 (s, 2H), 5.37 (s br, 1H), 2.68 (q, J=7.6 Hz, 4H), 1.29 (t, J=7.6 Hz, 6H).

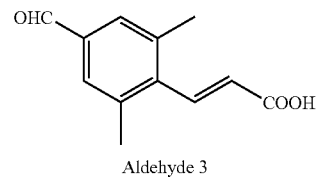

Aldehyde 3 a) To a solution of 4-hydroxy-3,5-dimethyl-benzaldehyde (5.0 g, 33.3 mmol) in DCM (50 mL) and pyridine (8 mL), trifluoromethanesulfonic anhydride (6 mL, 36.6 mmol) is slowly added at 0° C. Upon complete addition, stirring is continued for 2 h at rt. The reaction mixture is diluted with EA and washed three times with water. The separated organic layer is dried over MgSO$_4$, filtered and evaporated. The crude product is purified by CC on silica gel eluting with heptane:EA 4:1 to give trifluoro-methanesulfonic acid 4-formyl-2,6-dimethyl-phenyl ester (5.3 g) as a slightly yellow solid; LC-MS: $t_R$=1.04 min; $^1$H NMR (CDCl$_3$): δ 9.97 (s, 1H), 7.66 (s, 2H), 2.48 (s, 6H).

b) To a stirred solution of trifluoro-methanesulfonic acid 4-formyl-2,6-dimethyl-phenyl ester (4.7 g, 16.7 mmol) in dry DMF (75 mL) under argon is sequentially added at rt triethylamine (3.4 g, 33.3 mmol), methyl acrylate (14.3 g, 167 mmol), 1,3-bis-(diphenylphosphino)-propane (378 mg, 0.92 mmol) and Pd(OAc)$_2$ (187 mg, 0.83 mmol). The mixture is heated to 115° C. and stirred for 5 h. The mixture is diluted with diethyl ether (350 mL) and washed twice with aq. 1 N HCl and once with sat. aq. NaHCO$_3$. The organic extract is dried over MgSO$_4$, filtered and evaporated. The residue is purified by CC on silica gel eluting with heptane:EA 5:1 to give 3-(4-formyl-2,6-dimethyl-phenyl)-acrylic acid methyl ester (2.9 g) as a slightly yellow solid; LC-MS: $t_R$=0.96 min.

c) To a solution of 3-(4-formyl-2,6-dimethyl-phenyl)-acrylic acid methyl ester (2.9 g, 13.3 mmol) in methanol (70 mL), 2 N aq. NaOH (35 mL) is added. The suspension is stirred for 30 min at rt. Methanol is evaporated and the aq. solution is extracted twice with DCM. The aq. layer is acidified with 2 N aq. HCl and extracted twice with EA. The combined EA extracts are dried over MgSO$_4$, filtered and evaporated. The crude product is recrystallized from EA to give 3-(4-formyl-2,6-dimethyl-phenyl)-acrylic acid (2.2 g) as pale yellow crystals; LC-MS: $t_R$=0.83 min; $^1$H NMR (D$_6$-DMSO): δ 12.65 (s br, 1H), 9.92 (s, 1H), 7.66 (d, J=16.4 Hz, 1H), 7.61 (s, 2H), 6.12 (d, J=16.4 Hz, 1H), 2.35 (s, 6H).

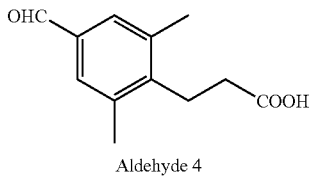

Aldehyde 4 a) To a solution of 3-(4-formyl-2,6-dimethyl-phenyl)-acrylic acid (2.2 g, 10.8 mmol) and DIPEA (2.0 mL, 11.9 mmol) in ethanol (80 mL), Pd/C (200 mg, 10% Pd, moistened with 50% water) is added. The suspension is vigorously stirred under 1 bar of $H_2$ for 1 h. The mixture is filtered over Celite and the filtrate is evaporated. The residue is poured onto 1 N aq. HCl/ice and extracted with EA. The organic extract is washed once with 1 N aq. HCl and once with brine, dried over $MgSO_4$, filtered and evaporated to give 3-(4-hydroxymethyl-2,6-dimethyl-phenyl)-propionic acid (2.2 g) as a pale yellow resin; LC-MS: $t_R$=0.71 min.

b) To a solution of 3-(4-hydroxymethyl-2,6-dimethyl-phenyl)-propionic acid (960 mg, 4.6 mmol) in acetic acid (20 mL), $MnO_2$ (1440 mg, 16.6 mmol) is added. The mixture is stirred at 80° C. for 4.5 h before it is filtered. The filtrate is evaporated and the crude product is purified by CC on silica gel eluting with DCM containing 8% of methanol to give 3-(4-formyl-2,6-dimethyl-phenyl)-propionic acid (800 mg) as a beige solid; LC-MS: $t_R$=0.81 min; $^1$H NMR ($D_6$-DMSO): δ 12.2 (s br, 1H), 9.86 (s, 1H), 7.52 (s, 2H), 2.93-2.85 (m, 2H), 2.38-2.30 (m, 8H).

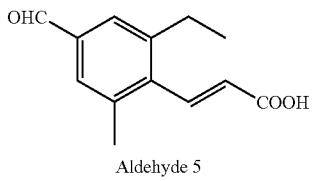

Aldehyde 5

3-(2-Ethyl-4-formyl-6-methyl-phenyl)-acrylic acid is prepared in analogy to Aldehyde 3; LC-MS: $t_R$=0.87 min; $^1$H NMR (CDCl$_3$): δ 9.98 (s, 1H), 7.96 (d, J=16.4 Hz, 1H), 7.62 (s, 1H), 7.59 8 s, 1H), 6.13 (d, J=16.4 Hz, 1H), 2.75 (q, J=7.6 Hz, 2H), 2.42 (s, 3H), 1.25 (t, J=7.6 Hz, 3H).

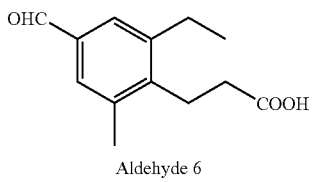

Aldehyde 6

3-(2-Ethyl-4-formyl-6-methyl-phenyl)-propionic acid is prepared in analogy to Aldehyde 4 starting from Aldehyde 5; LC-MS: $t_R$=0.86 min; $^1$H NMR (CDCl$_3$): δ 9.93 (s, 1H), 7.58 (s, 1H), 7.53 (s, 1H), 3.11-3.04 (m, 2H), 2.75 (q, J=7.6 Hz, 2H), 2.56-2.50 (m, 2H), 2.43 (s, 3H), 1.28 (t, J=7.6 Hz, 3H).

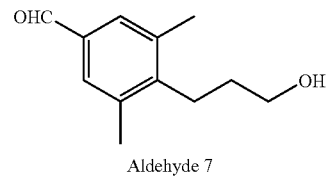

Aldehyde 7 a) To a suspension of LiAlH$_4$ (219 mg, 5.76 mmol) in THF (35 mL), a solution of 3-(4-hydroxymethyl-2,6-dimethyl-phenyl)-propionic acid (1.0 g, 4.80 mmol, intermediate from Aldehyde 4) in THF (10 mL) is added dropwise. Upon complete addition the suspension is refluxed for 2 h. The suspension is diluted with THF (10 mL) and another portion of LiAlH$_4$ (182 mg, 4.80 mmol) is added. The mixture is refluxed for further two hours, then cooled with an ice-bath. The reaction is carefully quenched by adding sat. aq. NH$_4$Cl solution (2 mL) followed by 2 N aq. HCl until a clear solution forms. The mixture is diluted with water and extracted twice with EA. The combined organic extracts are dried over MgSO$_4$, filtered and the solvent of the filtrate is evaporated to leave 3-(4-hydroxymethyl-2,6-dimethyl-phenyl)-propan-1-ol (920 mg) as a colourless crystalline solid; LC-MS: $t_R$=0.70 min, [M+1−H$_2$O]$^+$=177.20.

b) To a solution of 3-(4-hydroxymethyl-2,6-dimethyl-phenyl)-propan-1-ol (850 mg, 4.38 mmol) in ethanol (20 mL), MnO$_2$ (1.14 g, 13.1 mmol) is added and the resulting suspension is stirred at 85° C. for 24 h. The mixture is filtered through celite and the solvent of the filtrate is evaporated. The product is purified by CC on silica gel eluting with DCM containing 3% of methanol to give 4-(3-hydroxy-propyl)-3,5-dimethyl-benzaldehyde as a pale yellow solid; LC-MS: $t_R$=0.81 min; $^1$H NMR (CDCl$_3$): δ 9.89 (s, 1H), 7.51 (s, 2H), 3.76 (t, J=5.8 Hz, 2H), 2.81-2.74 (m, 2H), 2.40 (s, 6H), 1.80-1.68 (m, 2H).

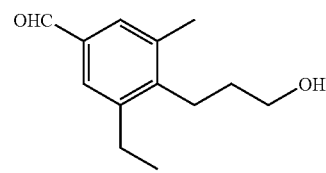

Aldehyde 8

3-Ethyl-4-(3-hydroxy-propyl)-5-methyl-benzaldehyde is prepared in analogy to Aldehyde 7; LC-MS: $t_R$=0.86 min; $^1$H NMR (CDCl$_3$): δ 9.92 (s, 1H), 7.56 (s, 1H), 7.52 (s, 1H), 3.72 (t, J=5.9 Hz, 2H), 2.83-2.77 (m, 2H), 2.74 (q, J=7.6 Hz, 2H), 2.42 (s, 3H), 1.80-1.70 (m, 2H), 1.27 (t, J=7.6 Hz, 3H).

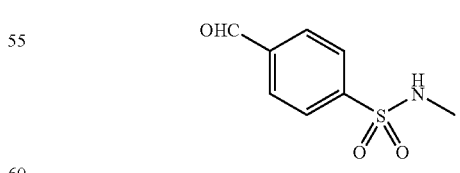

Aldehyde 9 a) To a solution of 4-chlorosulfonylbenzoic acid (5.8 g, 25.2 mmol) in DCM (200 mL), a solution of methylamine (52.15 mL, 2 M in THF) is added. The mixture is stirred overnight at rt before the solvent is evaporated. The residue is dissolved in sat. aq. NH$_4$Cl solution and extracted with EA.

The organic extract is washed with water, dried over MgSO$_4$, filtered and the solvent of the filtrate is evaporated to give 4-methylsulfamoyl-benzoic acid (3.77 g) as a white solid; LC-MS: t$_R$=0.64 min.

b) At 0° C., borane-THF complex (66.8 mL, 1 M in THF) is carefully added to a solution of 4-methylsulfamoyl-benzoic acid (3.56 g, 16.5 mmol) in THF (90 mL). The mixture is refluxed for 1.5 h, cooled to rt and diluted with 1 N aq. HCl (175 mL). The mixture is extracted with EA and the organic extract is washed with sat. aq. NaHCO$_3$, dried over MgSO$_4$ and filtered. The filtrate is concentrated and the crude product is purified by CC on silica gel eluting with DCM containing 5% of methanol to give 4-hydroxymethyl-N-methyl-benzenesulfonamide (1.61 g) as a colourless oil; LC-MS: t$_R$=0.56 min, [M+1+CH$_3$CN]$^+$=243.14.

c) A solution of 4-hydroxymethyl-N-methyl-benzenesulfonamide (1.61 g, 8.0 mmol) in DCM (50 mL) is added to a mixture of MnO$_2$ (16.1 g, 167 mmol) in DCM (65 mL). The mixture is stirred at rt for 15 min, filtered over celite and the solvent of the filtrate is evaporated to give 4-formyl-N-methyl-benzenesulfonamide (651 mg) as a white solid; LC-MS: t$_R$=0.68 min; $^1$H NMR (D$_6$-DMSO): δ 10.08 (s, 1H), 8.12-8.07 (m, 2H), 7.98-7.94 (m, 2H), 7.68 (s br, 1H), 2.42 (s, 3H).

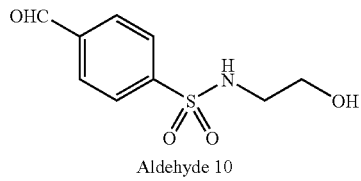

Aldehyde 10

4-Formyl-N-(2-hydroxy-ethyl)-benzenesulfonamide is prepared in analogy to Aldehyde 9; LC-MS: t$_R$=0.60 min; $^1$H NMR (CDCl$_3$): δ 10.01 (s, 1H), 8.07-8.02 (m, 4H), 5.10 8 t br, J=5 Hz, 1H), 3.75-3.70 (m, 2H), 3.20-3.15 (m, 2H).

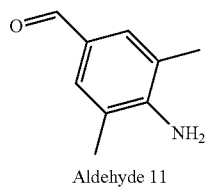

Aldehyde 11

To a solution of 2,4,6-trimethylaniline (29.8 g, 0.22 mol) in dioxane (300 mL) DDQ (49.9 g, 0.22 mol) is added. The brown suspension is stirred at rt for 18 h before it is filtered. The solvent of the filtrate is evaporated and the crude product is purified by CC on silica gel eluting with hexane:EA 1:1 to give 4-amino-3,5-dimethyl-benzaldehyde (5.0 g) as a beige solid; LC-MS: t$_R$=0.78 min, [M+1]$^+$=150.26.

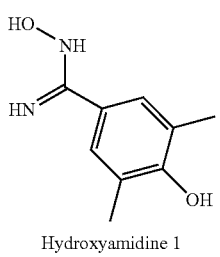

Hydroxyamidine 1

To dry methanol (190 mL) is carefully added K-tert.-butylate (18.68 g, 166 mmol) followed by hydroxylamine hydrochloride (9.92 g, 143 mmol). The suspension is stirred for 30 min before 3,5-dimethyl-4-hydroxybenzonitrile (7.00 g, 147 mmol) is added. The mixture is refluxed for 32 h, then the suspension is diluted by adding 2 N aq. HCl. The solution is extracted twice with DCM (100 mL). The aq. layer is basified (pH 9) by adding solid NaHCO$_3$ and extracted five times with DCM followed by four times with EA. The combined organic layers are dried over Na$_2$SO$_4$ and evaporated to dryness to give 4,N-dihydroxy-3,5-dimethyl-benzamidine (7.9 g) as a colourless solid; LC-MS: t$_R$=0.62 min, [M+1]$^+$=181.14.

Hydroxyamidine 2

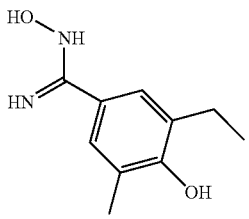

3-Ethyl-4,N-dihydroxy-5-methyl-benzamidine is prepared from commercially available 2-ethyl-6-methyl-phenol following literature procedures (G. Trapani, A. Latrofa, M. Franco, C. Altomare, E. Sanna, M. Usala, G. Biggio, G. Liso, J. Med. Chem. 41 (1998) 1846-1854; A. K. Chakraborti, G. Kaur, Tetrahedron 55 (1999) 13265-13268; E. Meyer, A. C. Joussef, H. Gallardo, Synthesis 2003, 899-905); LC-MS: t$_R$=0.55 min; $^1$H NMR (D$_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

Hydroxyamidine 3

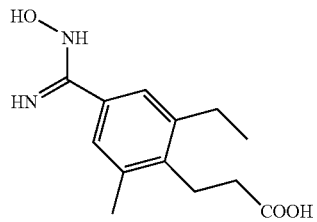

a) To an ice-cooled solution of 5-ethyl-4-hydroxy-3-methylbenzaldehyde (10.0 g, 60.9 mmol, Aldehyde 1) in DCM (50 mL) and pyridine (15 mL), trifluoromethanesulfonic acid anhydride (18.9 g, 67 mmol) is added over a period of 20 min. Upon complete addition, the ice bath is removed and the reaction is stirred for further 2 hours at rt. The mixture is diluted with DCM (150 mL), washed three times with water, dried over MgSO$_4$, filtered and evaporated. The residue is purified by flash chromatography on silica gel eluting with heptane:EA 9:1 to give trifluoro-methanesulfonic acid 2-ethyl-4-formyl-6-methyl-phenyl ester (10.75 g) as a pale yellow oil; LC-MS: $t_R$=1.07 min; $^1$H NMR (CDCl$_3$): δ 9.98 (s, 1H), 7.70 (s, 1H), 7.66 (s, 1H), 2.85 (q, J=10.1 Hz, 2H), 2.48 (s, 3H), 1.30 (t, J=10.2 Hz, 3H).

b) To a stirred solution of the above triflate (10.7 g, 36.1 mmol) in dry DMF (75 mL) is sequentially added triethylamine (7.3 g, 72.2 mmol), methyl acrylate (31.1 g, 361 mmol), DPPP (819 mg, 1.99 mmol) and Pd(OAc)$_2$ (405 mg, 1.81 mmol) under nitrogen. The mixture is stirred at 115° C. for 5 h, cooled to rt, diluted with diethyl ether (350 mL) and washed twice with 1 N aq. HCl and once with sat. aq. NaHCO$_3$ solution. The organic extract is dried over MgSO$_4$, filtered and evaporated. The residue is purified by flash chromatography on silica gel eluting with heptane:EA 19:1 to give 3-(2-ethyl-4-formyl-6-methyl-phenyl)-acrylic acid methyl ester (5.93 g) as a colourless liquid; LC-MS: $t_R$=0.99 min.

c) A suspension of 3-(2-ethyl-4-formyl-6-methyl-phenyl)-acrylic acid methyl ester (5.93 g, 25.53 mmol) in methanol (140 mL) and 2 N aq. NaOH (45 mL) is stirred at rt for 1 h. The methanol is evaporated and the aq. solution is extracted twice with DCM. The aq. layer is acidified with 37% aq. HCl. The precipitate that forms is collected, washed with water and dried. The product is further purified by recrystallisation from EA (100 mL) to give 3-(2-ethyl-4-formyl-6-methyl-phenyl)-acrylic acid (4.2 g) as yellow crystals; LC-MS: $t_R$=0.87 min.

d) To a solution of 3-(2-ethyl-4-formyl-6-methyl-phenyl)-acrylic acid (2.75 g, 12.6 mmol) and DIPEA (1.8 g, 13.8 mmol) in ethanol (80 mL), Pd/C (275 mg, 10% Pd, moistened with 50% water) is added. The mixture is stirred for 16 h at rt under 1 atm of H$_2$. The catalyst is filtered off and the filtrate is concentrated. The residue is dissolved in EA, washed with 2 N aq. HCl, followed by 1 N aq. HCl and brine. The organic extract is dried over Na$_2$SO$_4$, filtered and evaporated to give 3-(2-ethyl-4-hydroxymethyl-6-methyl-phenyl)-propionic acid (2.8 g) as a white solid; LC-MS: $t_R$=0.76 min.

e) A solution of 3-(2-ethyl-4-hydroxymethyl-6-methyl-phenyl)-propionic acid (2.8 g, 12.6 mmol) in acetic acid (50 mL) is treated with MnO$_2$ (3.9 g, 45.4 mmol) and the resulting mixture is stirred at 80° C. for 4 h. The mixture is filtered and the filtrate is concentrated. The crude product is purified by CC on silica gel eluting with DCM to give 3-(2-ethyl-4-formyl-6-methyl-phenyl)-propionic acid (1.76 g) as a beige solid; LC-MS: $t_R$=0.86 min.

f) A solution of 3-(2-ethyl-4-formyl-6-methyl-phenyl)-propionic acid (1.67 g, 7.58 mmol) and hydroxylamine hydrochloride (780 mg, 11.36 mmol) in 1-methyl-2-pyrrolidone is heated to 80° C. for 30 min in the microwave (300 W, active cooling during irradiation). The reaction mixture is diluted with diethyl ether and washed with water and brine. The organic extract is dried over Na$_2$SO$_4$, filtered and evaporated to give 3-(4-cyano-2-ethyl-6-methyl-phenyl)-propionic acid (1.55 g) as a beige solid; LC-MS: $t_R$=0.89 min, $^1$H NMR (D$_6$-DMSO): δ 12.25 (s, 1H), 7.45 (s, 2H), 2.91-2.84 (m, 2H), 2.67-2.59 (m, 2H), 2.35-2.30 (m, 5H), 1.14 (t, J=7.6 Hz, 3H).

g) Potassium tert. butoxide (2.71 g, 24.1 mmol) is carefully dissolved in methanol (25 mL). To this solution hydroxylamine hydrochloride (1.44 g, 20.7 mmol) followed by 3-(4-cyano-2-ethyl-6-methyl-phenyl)-propionic acid (1.50 g, 6.90 mmol) dissolved in methanol (7.5 mL) is added. The mixture is refluxed for 8 h and the solvent is evaporated. The residue is dissolved in 2 N aq. HCl and extracted with EA. The pH of the aq. phase is adjusted to pH 5 by adding sat. aq. NaHCO$_3$ and the mixture is extracted three times with EA. The combined organic extracts are dried over Na$_2$SO$_4$, filtered, evaporated and dried to give 3-[2-ethyl-4-(N-hydroxycarbamimidoyl)-6-methyl-phenyl]-propionic acid (1.4 g) as a white solid; LC-MS: $t_R$=0.60 min, [M+1]$^+$=251.17.

Hydroxyamidine 4

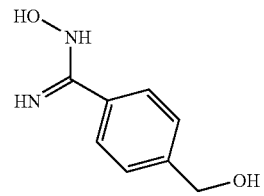

A mixture of 4-hydroxymethylbenzonitrile (5.0 g, 37.6 mmol), hydroxylamine hydrochloride (2.87 g, 41.3 mmol) and NaHCO$_3$ (4.10 g, 48.8 mmol) in methanol (200 mL) is refluxed for 20 h, filtered and the solvent of the filtrate is evaporated to give N-hydroxy-4-hydroxymethyl-benzamidine (7.1 g) as a white solid; LC-MS: $t_R$=0.22 min.

Example A

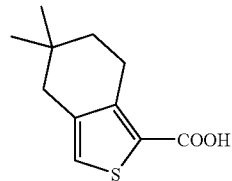

a) To a solution of 4,4-dimethyl-cyclohex-2-enone (50 g, 403 mmol) in EA (230 mL) a suspension of Pd/C (2.5 g, 10% Pd) in EA is added. The suspension is stirred at rt for 2 h under 1 bar H$_2$. The catalyst is filtered off and the solvent of the filtrate is carefully evaporated to give 4,4-dimethyl-cyclohexanone (50 g) as a colourless oil which slowly crystallizes; $^1$H NMR (CDCl$_3$): δ 2.34 (t, J=6.4 Hz, 4H), 1.66 (t, J=6.4 Hz, 4H), 1.09 (s, 6H).

b) To an ice-cold solution of K. tert.-butylate (24.5 g, 109 mmol, 50% solution in tert.-butanol) in THF (700 mL) ethylformate (120 mL, 123 mmol) is slowly added. The mixture is stirred at rt for 30 min before a solution of 4,4-dimethyl-cyclohexanone (50 g, 396 mmol) in ethylformate (50 mL) and THF (70 mL) is added over a period of 20 min. Upon complete addition, stirring is continued at 15-20° C. for 30 min. The orange suspension is poured onto 10% aq. citric acid solution (200 mL) and brine (200 mL) and extracted with EA (2×200 mL). The organic extracts are washed with 0.2 N aq. NaOH and brine, dried over Na$_2$SO$_4$ and evaporated to dryness to give 5,5-dimethyl-2-oxo-cyclohexanecarbaldehyde (52 g) as a yellow oil; LC-MS: $t_R$=0.89 min, [M+1+CH$_3$CN]$^+$= 196.15.

c) To a solution of 5,5-dimethyl-2-oxo-cyclohexanecarbaldehyde (51 g, 331 mmol) in chloroform (250 mL), oxalyl chloride (40 mL, 465 mmol) is rapidly added. After stirring for 3-4 min ice followed by 2 N aq. NaOH (100 mL) is added. The organic phase is separated and the aq. phase is extracted once more with chloroform. The combined organic extracts are washed with water and dried over $Na_2SO_4$. The solvent is removed in vacuo to give 2-chloromethylene-4,4-dimethyl-cyclohexanone (50 g) as a brown oil; LC-MS: $t_R$=0.96 min.

d) To a part (300 mL) of a freshly prepared solution of sodium (21 g, 875 mmol) in ethanol (500 mL), mercaptoacetic acid ethyl ester (50 mL) is added. The resulting solution is added over a period of 10 min to a solution of 2-chloromethylene-4,4-dimethyl-cyclohexanone (50 g, 290 mmol) in THF (170 mL). The mixture becomes warm (50° C.). Upon complete addition, the remaining part of the freshly prepared solution of sodium in ethanol (200 mL) is added to the reaction mixture. The mixture is stirred at rt for 15 min before 1 N aq. LiOH solution (300 mL) is added. The solution is refluxed for 3 h, then stirred at rt for 16 h. The THF and ethanol are removed under reduced pressure and the remaining dark solution is extracted with heptane/EA 3:1 (2×200 mL). The aq. phase is acidified by adding citric acid (30 g) and 2 N aq. HCl (200 mL) and then extracted three times with EA. The combined organic extracts are washed three times with sat. aq. $NaHCO_3$ solution, dried over $Na_2SO_4$ and evaporated. The resulting dark brown oil is dissolved in acetonitrile at 60° C. and crystallised at 5° C. The crystals are collected, washed with acetonitrile and dried to give 5,5-dimethyl-4,5,6,7-tetrahydro-benzo[c]thiophene-1-carboxylic acid (31 g) as a slightly grey powder; LC-MS: $t_R$=0.95 min, $[M+1+CH_3CN]^+$=252.18; $^1H$ NMR ($CDCl_3$): δ 7.15 (s, 1H), 3.05 (t, J=7.0 Hz, 2H), 2.47 (s, 2H), 1.58 (t, J=7.0 Hz, 2H), 0.97 (s, 6H).

Example B

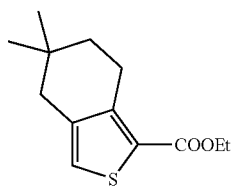

Example B is obtained following the procedures described in Example A omitting the final hydrolysis with aq. LiOH in step d). MPLC purification of the black oil obtained after work-up gives 5,5-dimethyl-4,5,6,7-tetrahydro-benzo[c]thiophene-1-carboxylic acid ethyl ester as a brown oil; LC-MS: $t_R$=1.10 min, $[M+1]^+$=239.12; $^1H$ NMR ($CD_3OD$): δ 7.20 (s, 1H), 4.24 (q, J=7.0 Hz, 2H), 3.00 (t, J=7.0 Hz, 2H), 2.45 (s, 2H), 1.57 (t, J=7.0 Hz, 2H), 1.33 (t, J=7.0 Hz, 3H), 0.96 (s, 6H).

Example C

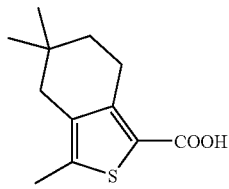

At −78° C. a solution of 5,5-dimethyl-4,5,6,7-tetrahydro-benzo[c]thiophene-1-carboxylic acid (5 g, 23.8 mmol) in THF is treated with tert.-butyllithium (41 mL, 1.5 M in pentane). The mixture is stirred at −78° C. for 15 min before methyliodide (17.1 g, 120 mmol) is added dropwise. Stirring is continued at −78° C. for 30 min. The mixture is warmed to rt, diluted with water (400 mL), acidified with 10% aq. citric acid solution and extracted three times with EA. The combined organic extracts are dried over $MgSO_4$ and evaporated. The remaining solid is suspended in heptane/diethyl ether, filtered and dried under HV to give 3,5,5-trimethyl-4,5,6,7-tetrahydro-benzo[c]thiophene-1-carboxylic acid (4.01 g) as a beige powder; LC-MS: $t_R$=0.97 min, $[M+1]$=225.13; $^1H$ NMR ($D_6$-DMSO): δ 12.49 (s br, 1H), 2.87 (t, J=6.7 Hz, 2H), 2.26 (s, 5H), 1.45 (t, J=6.7 Hz, 2H), 0.91 (s, 6H).

Example D

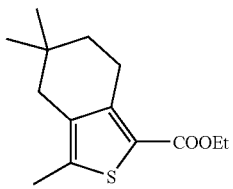

a) To a suspension of NaH (2.88 g, 60% dispersion in mineral oil, 60 mmol) in toluene (25 mL), EA (6.5 mL, 66 mmol) is added. The mixture is stirred at rt for 5 min before a solution of 4,4-dimethyl-cyclohexanone (2.52 g, 20 mmol) in EA (6 mL) is added. The mixture is heated to 55° C. where a vigorous reaction starts. The white to grey suspension turns orange and becomes clear. The clear solution is poured onto ice/water and is extracted with EA. The aq. phase is acidified to pH 4-5 and extracted once more with EA. The combined organic extracts are dried over $Na_2SO_4$ and the solvent is removed in vacuo to give 2-acetyl-4,4-dimethyl-cyclohexanone (2.00 g) as a yellow oil; $^1H$ NMR ($CDCl_3$): δ 2.35 (t, J=7.0 Hz, 2H), 2.12 (s, 2H), 2.10 (s, 1H), 1.48 (t, J=7.0 Hz, 2H), 0.98 (s, 6H).

b) At 0° C., a solution of 2-acetyl-4,4-dimethyl-cyclohexanone (5.00 g, 29.7 mmol) in chloroform (15 mL) is treated with oxalyl chloride (7.54 g, 59.4 mmol). The mixture is heated to 60° C. and stirred for 15 min before it is poured onto water. The organic phase is separated, washed with sat. aq. $NaHCO_3$ solution and brine, dried over $MgSO_4$ and evaporated to dryness to give crude 2-(1-chloro-ethylidene)-4,4-dimethyl-cyclohexanone (3.2 g, containing regio-isomer) as a brown oil, LC-MS: $t_R$=1.00 min.

c) To a mixture of NaOEt (10 mL of a 2.5 M solution in ethanol, 25 mmol) in THF (10 mL) mercaptoacetic acid ethyl ester (3.09 g, 25.7 mmol) followed by a solution of the above 2-(1-chloro-ethylidene)-4,4-dimethyl-cyclohexanone (3.2 g, 17.14 mmol) is added. The resulting solution is stirred at 60° C. for 45 min. The mixture is diluted with water and extracted with EA. The organic extract is dried over $Na_2SO_4$, evaporated and purified by CC on silica gel eluting with heptane/toluene and then heptane/EA to give 3,5,5-trimethyl-4,5,6,7-tetrahydro-benzo[b]thiophene-2-carboxylic acid ethyl ester (3.1 g) as a brown oil containing the regio isomer 3,5,5-trimethyl-4,5,6,7-tetrahydro-benzo[b]thiophene-2-carboxylic acid ethyl ester. An analytical sample is purified by prep. HPLC to give pure 3,5,5-trimethyl-4,5,6,7-tetrahydro-benzo[b]thiophene-2-carboxylic acid ethyl ester as a colourless oil; LC-MS: $t_R$=1.13 min, [M+1]=252.99; $^1$H NMR (CDCl$_3$): δ 4.29 (q, J=7.0 Hz, 2H), 3.00 (t, J=6.4 Hz, 2H), 2.30 (s, 3H), 2.26 (s, 2H), 1.52 (t, J=6.4 Hz, 2H), 1.34 (t, J=7.0 Hz, 3H), 0.96 (s, 6H).

Example E

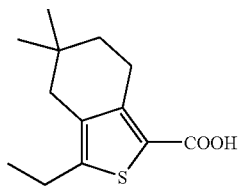

To a cooled solution (−78° C.) of 5,5-dimethyl-4,5,6,7-tetrahydro-benzo[c]thiophene-1-carboxylic acid (960 mg, 4.57 mmol) in THF (19 mL), tert.-butyllithium (8 mL, 1.5 M solution in pentane) is added. The mixture is stirred at −78° C. for 10 min before ethyliodide (3.80 g, 24.37 mmol) is added. The reaction mixture is stirred at −78° C. for 3 h. Water/methanol 1:1 (8 mL) followed by 10% aq. citric acid solution is added and the mixture is extracted with EA. The combined organic extracts are washed with brine, dried over $Na_2SO_4$ and evaporated. The remaining solid is suspended in acetonitrile (6 mL), heated to 60° C., cooled to rt, filtered and dried to give 3-ethyl-5,5-dimethyl-4,5,6,7-tetrahydro-benzo[c]thiophene-1-carboxylic acid (640 mg) as a slightly beige solid; LC-MS: $t_R$=1.01 min, [M+1+CH$_3$CN]=280.10.

Example F

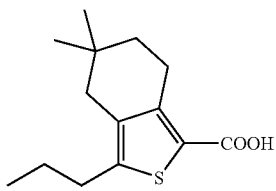

To a cooled (−75° C.) solution of 5,5-dimethyl-4,5,6,7-tetrahydro-benzo[c]thiophene-1-carboxylic acid (2.0 g, 9.51 mmol) in THF (40 mL) tert.-butyllithium (15 mL, 1.5 N in pentane) is slowly added. The mixture is stirred at −78° C. for 15 min before n-propyliodide (5.22 g, 30.7 mmol) is added. Stirring is continued at −78° C. for 45 min before the reaction is quenched by adding water/methanol 1:1 (10 mL). The mixture is allowed to warm to rt, diluted with tert.-butyl methylether and 10% aq. citric acid solution. The mixture is extracted twice with EA, the combined organic extracts are washed with brine, dried over $Na_2SO_4$ and concentrated. The crude product is purified by prep. HPLC to give 5,5-dimethyl-3-propyl-4,5,6,7-tetrahydro-benzo[c]thiophene-1-carboxylic acid (200 mg) as a colourless resin; LC-MS: $t_R$=1.04 min, [M+1]=253.31; $^1$H NMR (CDCl$_3$): δ 2.98 (t, J=7.0 Hz, 2H), 2.63 (t, J=7.6 Hz, 2H), 2.36 (s br, 1H), 2.26 (s, 2H), 1.63 (hex, J=7.6 Hz, 2H), 1.51 (t, J=7.0 Hz, 2H), 0.95 (t, J=7.6 Hz, 3H), 0.94 (s, 6H).

Example G

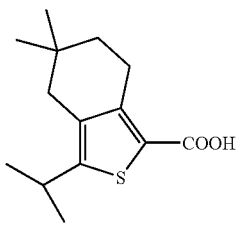

To a cooled solution (−78° C.) of 5,5-dimethyl-4,5,6,7-tetrahydro-benzo[c]thiophene-1-carboxylic acid (2.00 g, 9.51 mmol) in THF (35 mL), tert.-butyllithium (16 mL, 1.5 M solution in pentane) is added. The mixture is stirred at −78° C. for 10 min before isopropyliodide (7.60 g, 48.7 mmol) is added. The reaction mixture is stirred at −78° C. for 3 h, then at rt for 3 d. The reaction mixture is diluted with water and extracted twice with EA. The combined organic extracts are dried over $Na_2SO_4$ and evaporated. The crude product is purified by CC on silica gel eluting with DCM/TBME 20:1 followed by prep. HPLC to give 3-isopropyl-5,5-dimethyl-4,5,6,7-tetrahydro-benzo[c]thiophene-1-carboxylic acid (500 mg) as a white solid; LC-MS: $t_R$=1.04 min, [M+1+CH$_3$CN]=294.16.

Example H

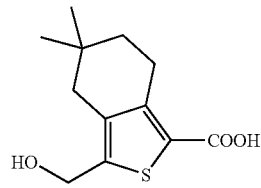

a) To a cooled (−78° C.) solution of 5,5-dimethyl-4,5,6,7-tetrahydro-benzo[c]thiophene-1-carboxylic acid (2.00 g, 9.51 mmol) in THF (40 mL), tert.-butyllithium (15.8 mL, 1.5 M in pentane) is added. The mixture is stirred at −30° C. for 30 min and cooled again to −78° C. before DMF (2 mL, 27.4 mmol) is added. Stirring is continued for 5 min. The reaction mixture is poured onto 10% aq. citric acid solution and extracted twice with EA. The combined organic extracts are washed with brine, dried over $Na_2SO_4$ and evaporated go give crude 3-formyl-5,5-dimethyl-4,5,6,7-tetrahydro-benzo[c]thiophene-1-carboxylic acid (2.30 g) as a brownish foam, LC-MS: $t_R$=0.92 min, [M+1+CH$_3$CN]=280.22; $^1$H NMR (CDCl$_3$): δ 10.06 (s, 1H), 4.02 (s br, 1H), 3.06 (t, J=6.7 Hz, 2H), 2.84 (s, 2H), 1.63 (t, J=6.7 Hz, 2H), 1.03 (s, 6H).

b) To a solution of crude 3-formyl-5,5-dimethyl-4,5,6,7-tetrahydro-benzo[c]thiophene-1-carboxylic acid (2.38 g, 10 mmol) in methanol (20 mL) NaBH$_4$ (756 mg, 20 mmol) is added in portions. The mixture is stirred at rt for 15 min, diluted with 10% aq. citric acid and brine and extracted with TBME. The organic extract is dried over Na$_2$SO$_4$ and the solvent is removed under reduced pressure to give 3-hydroxymethyl-5,5-dimethyl-4,5,6,7-tetrahydro-benzo[c]thiophene-1-carboxylic acid (2.30 g) as a beige foam; LC-MS: t$_R$=0.83 min, [M+1]=241.22; $^1$H NMR (CDCl$_3$): δ 4.69 (s, 2H), 3.00 (t, J=7.0 Hz, 2H), 2.32 (s, 2H), 1.50 8 t, J=7.0 Hz, 2H), 0.94 (s, 6H).

Example I

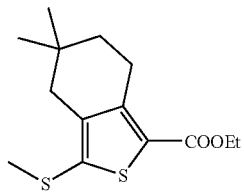

a) To a suspension of K tert.-butylate (2.38 g, 25.2 mmol) in THF (20 mL), 3-methylsulfanyl-4-oxo-4,5,6,7-tetrahydro-benzo[c]thiophene-1-carboxylic acid ethyl ester (2.64 g, 9.77 mmol) is added in portions. To the dark violet mixture a solution of methyliodide (3.56 g, 25.1 mmol) in THF (5 mL) is slowly added. The mixture is stirred at 40° C. for 16 h before another portion of methyliodide (1.03 g, 7.23 mmol) is added at 0° C. The mixture is stirred at rt for further 24 h, is then diluted with diethyl ether and washed with brine. The organic layer is separated, dried over Na$_2$SO$_4$ and the solvent is evaporated. The crude product is purified by CC on silica gel eluting with heptane:EA 5:1 to give 5,5-dimethyl-3-methylsulfanyl-4-oxo-4,5,6,7-tetrahydro-benzo[c]thiophene-1-carboxylic acid ethyl ester (539 mg) as a beige resin; LC-MS: t$_R$=1.07 min, [M+1]=299.10; $^1$H NMR (CDCl$_3$): δ 4.33 (q, J=7.0 Hz, 2H), 3.20 (t, J=6.4 Hz, 2H), 2.59 (s, 3H), 1.90 (t, J=6.4 Hz, 2H), 1.37 (t, J=7.0 Hz, 3H), 1.20 (s, 6H).

b) To a suspension of anhydrous ZnI$_2$ (647 mg, 2.03 mmol) and Na(BH$_3$CN) (117 mg, 1.86 mmol) in DCM (5 mL), a solution of 5,5-dimethyl-3-methylsulfanyl-4-oxo-4,5,6,7-tetrahydro-benzo[c]thiophene-1-carboxylic acid ethyl ester (539 mg, 1.81 mmol) in DCM (5 mL) is added. The yellow suspension is refluxed over night before another portion of ZnI$_2$ (100 mg, 0.314 mmol) and Na(BH$_3$CN) (26 mg, 0.419 mmol) is added. The reaction mixture is refluxed for further 24 h. The mixture is diluted with diethyl ether and washed with sat. aq. NaHCO$_3$ solution and brine. The organic layer is separated, dried over Na$_2$SO$_4$ and the solvent is removed under reduced pressure to give 5,5-dimethyl-3-methylsulfanyl-4,5,6,7-tetrahydro-benzo[c]thiophene-1-carboxylic acid ethyl ester as a beige resin; LC-MS: t$_R$=1.15 min, [M+1]=285.2; $^1$H NMR (CDCl$_3$): δ 4.30 (q, J=7.0 Hz, 2H), 3.00 (t, J=7.0 Hz, 2H), 2.50 (s, 3H), 2.33 (s, 3H), 1.54 (t, J=7.0 Hz, 2H), 1.35 (t, J=7.0 Hz, 3H), 0.97 (s, 6H).

Example K

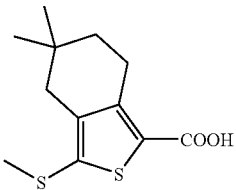

A solution of 5,5-dimethyl-3-methylsulfanyl-4,5,6,7-tetrahydro-benzo[c]thiophene-1-carboxylic acid ethyl ester (458 mg, 1.61 mmol) and LiOH.H$_2$O (696 mg, 16.6 mmol) in ethanol (5 mL), THF (3 mL) and water (0.6 mL) is stirred at rt overnight. The mixture is diluted with aq. KHSO$_4$ and extracted with DCM. The organic extract is dried over Na$_2$SO$_4$, filtered and the solvent is removed in vacuo to give 5,5-dimethyl-3-methylsulfanyl-4,5,6,7-tetrahydro-benzo[c]thiophene-1-carboxylic acid (546 mg) as a beige solid; LC-MS: t$_R$=1.00 min, [M+1]=257.6; $^1$H NMR (CDCl$_3$): δ 2.98 (t, J=7.0 Hz, 2H), 2.49 (s, 3H), 2.34 (s, 2H), 1.55 (t, J=7.0 Hz, 2H), 0.98 (s, 6H).

Example L

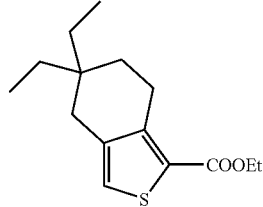

a) A mixture of 2-ethylbutyraldehyde (12.3 mL, 100 mmol), methylvinylketone (5.6 mL, 67.3 mmol) and H$_2$SO$_4$ (0.07 mL) is stirred at 40° C. overnight. Another portion of methylvinylketone (5.6 mL, 67.3 mmol) and H$_2$SO$_4$ is added and stirring is continued at 40° C. for 2 d. The yellow solution is diluted with chloroform and the solvent is removed again under reduced pressure. The crude product is purified by vacuum distillation to give 4,4-diethyl-cyclohex-2-enone (10.7 g) as a colourless oil; Kp$_{11\ mbar}$=88° C.; $^1$H NMR (CDCl$_3$): δ 6.71 (d, J=10.0 Hz, 1H), 5.92 (d, J=10.5 Hz, 1H), 2.42 (t, J=7.0 Hz, 2H), 1.84 (t, J=7.0 Hz, 2H), 1.57-1.40 (m, 4H), 0.87 (t, J=7.6 Hz, 6H).

b) A solution of 4,4-diethyl-cyclohex-2-enone (10.7 g, 70.5 mmol) in EA (400 mL) is treated with Pd/C (1.0 g, 10% Pd). The suspension is stirred at rt for 24 h under 1 bar of H$_2$. The mixture is filtered, and the filtrate is evaporated to give 4,4-diethyl-cyclohexanone (11.7 g) as a colourless solid; $^1$H NMR (CD$_3$OD): δ 2.32 (t, J=7.0 Hz, 4H), 1.66 (t, J=7.0 Hz, 4H), 1.48 (q, J=7.6 Hz, 4H), 0.88 (t, J=7.6 Hz, 6H).

c) To a suspension of K tert.-butylate (9.19 g, 81.9 mmol) in THF (250 mL), ethylformate (24.8 mL, 260 mmol) is slowly added. To the slightly turbid mixture a solution of 4,4-diethyl-cyclohexanone (11.5 g, 74.4 mmol) in ethyl formate (14 mL, 150 mmol) is added. The mixture becomes warm and is cooled with an ice-bath. The dark red to brown suspension is stirred at rt for 18 h before 10% aq. citric acid is added. The mixture is extracted with DCM and the organic extract is dried over $Na_2SO_4$ and evaporated. The brown oil is dissolved in chloroform (150 mL) and treated with oxaxylchloride (11.3 g, 89.1 mmol). After gas evolution has stopped, the mixture is stirred for 1 h at rt. The dark solution is washed with 2 N aq. NaOH, dried over $Na_2SO_4$ and evaporated to leave a black oil (11.2 g). A solution of this oil in THF (60 mL) is added to a cold solution (3° C.) of NaOEt (11.4 g, 167 mmol) and mercaptoacetic acid ethyl ester (10.0 g, 83.6 mmol) in ethanol (300 mL). The reaction mixture is stirred at rt for 2 h before another portion of NaOEt (5.69 g, 83.6 mmol) is added. Stirring is continued at rt for 16 h and at 60° C. for 2 h. The mixture is diluted with 2 N aq. HCl and is extracted twice with DCM. The combined organic extracts are dried over $Na_2SO_4$, filtered and the solvent is removed in vacuo to give crude 5,5-diethyl-4,5,6,7-tetrahydro-benzo[c]thiophene-1-carboxylic acid ethyl ester (14.2 g) as a brown oil; LC-MS: $t_R$=1.16 min.

Example M

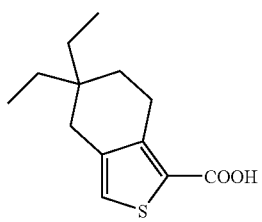

A solution of 5,5-diethyl-4,5,6,7-tetrahydro-benzo[c]thiophene-1-carboxylic acid ethyl ester (14.2 g, 53.38 mmol) in ethanol (250 mL) and 2 N aq. LiOH (250 mL) is stirred at 65° C. for 18 h. The mixture is diluted with 1 N aq. NaOH and extracted with diethyl ether. The aq. phase is acidified to pH 2 with 2 N aq. HCl and extracted with DCM. The combined DCM extracts are dried over $Na_2SO_4$, filtered, and the solvent is removed in vacuo. The crude product (11.3 g) is purified by MPLC on Rp-$C_{18}$ silica gel to give 5,5-diethyl-4,5,6,7-tetrahydro-benzo[c]thiophene-1-carboxylic acid (2.93 g) as a brown oil; LC-MS: $t_R$=1.01 min, [M+1+$CH_3CN$]=280.19; $^1$H NMR ($CDCl_3$): δ 7.12 (s, 1H), 2.99 (t, J=7.0 Hz, 2H), 2.46 (s, 2H), 1.59 (t, J=7.0 Hz, 2H), 1.40-1.20 (m, 4H), 0.84-0.74 (m, 6H).

Example N

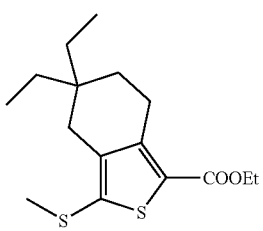

5,5-Diethyl-3-methylsulfanyl-4,5,6,7-tetrahydro-benzo[c]thiophene-1-carboxylic acid ethyl ester is prepared starting from 3-methylsulfanyl-4-oxo-4,5,6,7-tetrahydro-benzo[c]thiophene-1-carboxylic acid ethyl ester in analogy to the procedure given in Example I; LC-MS: $t_R$=1.20 min, [M+1]= 313.1; $^1$H NMR ($CDCl_3$): δ 4.30 (q, J=7.0 Hz, 2H), 2.94 (t, J=7.0 Hz, 2H), 2.50 (s, 3H), 2.32 (s, 2H), 1.54 (t, J=7.0 Hz, 2H), 1.40-1.25 (m, 7H), 0.82 (t, J=7.6 Hz, 6H).

Example O

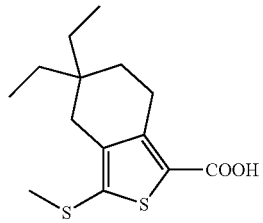

5,5-Diethyl-3-methylsulfanyl-4,5,6,7-tetrahydro-benzo[c]thiophene-1-carboxylic acid ethyl ester is treated with LiOH as described in Example K to give 5,5-diethyl-3-methylsulfanyl-4,5,6,7-tetrahydro-benzo[c]thiophene-1-carboxylic acid; LC-MS: $t_R$=1.06 min, [M+1]=285.0; $^1$H NMR ($CDCl_3$): δ 2.96 (t, J=6.4 Hz, 2H), 2.54 (s, 3H), 2.31 (s, 2H), 1.55 (t, J=6.4 Hz, 2H), 1.37-1.20 (m, 4H), 0.83 (t, J=7.3 HZ, 6H).

Example P

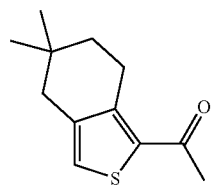

To a solution of 5,5-dimethyl-4,5,6,7-tetrahydro-benzo[c]thiophene-1-carboxylic acid (1051 mg, 5.0 mmol) in diethyl ether (15 mL) and THF (8 mL), methyllithium (7 mL of a 1.6 M solution in diethyl ether) is added. The mixture is stirred at rt for 15 min before the reaction is quenched with ethanol. The mixture is diluted with 10% aq. citric acid and extracted with TBME. The organic extract is washed three times with sat. aq. $NaHCO_3$, dried over $Na_2SO_4$ and evaporated to give crude 1-(5,5-dimethyl-4,5,6,7-tetrahydro-benzo[c]thiophen-1-yl)-ethanone (1.0 g) as a brownish oil; LC-MS: $t_R$=1.03 min, [M+1]=209.07.

Example Q

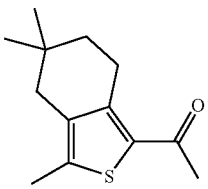

To a suspension of 3,5,5-trimethyl-4,5,6,7-tetrahydro-benzo[c]thiophene-1-carboxylic acid (4.10 g, 18.28 mmol) in diethyl ether (300 mL), methyllithium (23 mL, 1.6 M solution in diethyl ether) is slowly added at rt. The reaction mixture becomes clear, yellow and slightly warm (26° C.), and is stirred for 15 min before it is quenched with water. The organic layer is separated, washed once more with water, dried over MgSO₄ and evaporated. The crude product is purified by CC on silica gel eluting with heptane:EA 4:1 to give 1-(3,5,5-trimethyl-4,5,6,7-tetrahydro-benzo[c]thiophen-1-yl)-ethanone (2.80 g) as a pale yellow crystalline solid; LC-MS: $t_R$=1.06 min, [M+1]=223.17; ¹H NMR (CDCl₃): δ 3.00 (t, J=7.0 Hz, 2H), 2.43 (s, 3H), 2.31 (s, 3H), 2.26 (s, 2H), 1.51 (t, J=7.0 Hz, 2H), 0.95 (s, 6H).

Example R

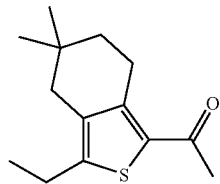

To a solution of 3-ethyl-5,5-dimethyl-4,5,6,7-tetrahydro-benzo[c]thiophene-1-carboxylic acid (2.10 g, 8.81 mmol) in diethyl ether (100 mL), a solution of methyllithium (11 mL, 1.6 M solution in diethyl ether) is added at rt. The pale yellow solution is stirred at rt for 15 min before another portion of methyllithium (2 mL) is added. Stirring is continued for 15 min, a further portion of methyllithium (1 mL) is added, and the mixture is again stirred for 15 min at rt. The reaction is quenched with water. The organic layer is separated, washed once more with water, dried over MgSO₄ and evaporate. The crude product is purified by CC on silica gel eluting with heptane:EA 7:3 to give 1-(3-ethyl-5,5-dimethyl-4,5,6,7-tetrahydro-benzo[c]thiophen-1-yl)-ethanone (1.65 g) as a pale yellow solid; LC-MS: $t_R$=1.00 min, [M+1]=237.15; ¹H NMR (CDCl₃): δ 3.03 (t, J=7.0 Hz, 2H), 2.73 (q, J=7.6 Hz, 2H), 2.47 (s, 3H), 2.31 (s, 2H), 1.55 (t, J=7.0 Hz, 2H), 1.28 (t, J=7.6 Hz, 3H), 0.97 (s, 6H).

Example S

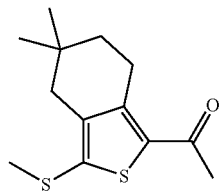

To a solution of 5,5-dimethyl-3-methylsulfanyl-4,5,6,7-tetrahydro-benzo[c]thiophene-1-carboxylic acid (508 mg, 1.98 mmol) in diethyl ether (20 mL), a solution of methyllithium (1.1 mL, 1.6 M in diethyl ether) is added at rt. The mixture is stirred at rt for 1 h before another portion of methyllithium (0.25 mL) is added. Stirring is continued for 2 h. The reaction is quenched by the addition of 1 N aq. K₂HPO₄ solution. The mixture is diluted with diethyl ether, washed with 1 N aq. NaOH, dried over Na₂SO₄ and evaporated to give 1-(5,5-dimethyl-3-methylsulfanyl-4,5,6,7-tetrahydro-benzo[c]thiophen-1-yl)-ethanone (214 mg) as a yellow oil; LC-MS: $t_R$=1.09 min, [M+1]=255.1.

Example T

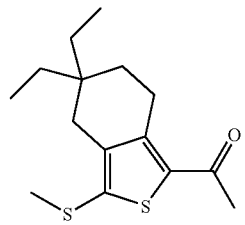

To a solution of 5,5-diethyl-3-methylsulfanyl-4,5,6,7-tetrahydro-benzo[c]thiophene-1-carboxylic acid (669 mg, 2.35 mmol) in diethyl ether (20 mL), a solution of methyllithium (2.6 mL, 1.6 M in diethyl ether) is added at rt. The reaction mixture is stirred at rt for 4 h, diluted with diethyl ether, washed with 1 N aq. K₂HPO₄ solution followed by 1 N aq. NaOH, dried over Na₂SO₄ and evaporated to give 1-(5,5-diethyl-3-methylsulfanyl-4,5,6,7-tetrahydro-benzo[c]thiophen-1-yl)-ethanone (458 mg) as a yellow oil, LC-MS: $t_R$=1.15 min, [M+1]=283.1; ¹H NMR(CDCl₃): δ 2.96 (t, J=7.0 Hz, 2H), 2.53 (s, 3H), 2.45 (s, 3H), 2.32 (s, 2H), 1.56 (t, J=7.0 Hz, 2H), 1.35-1.20 (m, 4H), 0.83 (t, J=7.6 Hz, 6H).

Example U

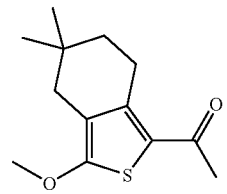

a) To a solution of 5,5-dimethyl-4,5,6,7-tetrahydro-benzo[c]thiophene-1-carboxylic acid ethyl ester (715 mg, 3.0 mmol) in acetic acid (5 mL), bromine (480 mg, 3.0 mmol) is slowly added at rt. Upon completion of the addition, the mixture is heated to 50° C. and stirred for 4 h. The reaction is quenched by adding 1 N aq. NaOH and the mixture is extracted with DCM (3×50 mL). The organic extracts are dried (Na₂SO₄), filtered and evaporated to provide crude 3-bromo-5,5-dimethyl-4,5,6,7-tetrahydro-benzo[c]thiophene-1-carboxylic acid ethyl ester (774 mg) as a brown oil; ¹H NMR (CDCl₃): δ 4.27 (q, J=7.6 Hz, 2H), 2.97 (t, J=7.0 Hz, 2H), 2.26 8 s, 2H), 1.51 (t, J=7.0 Hz, 2H), 1.33 8t, J=7.6 Hz, 3H), 0.95 (s, 6H).

b) A mixture of crude 3-bromo-5,5-dimethyl-4,5,6,7-tetrahydro-benzo[c]thiophene-1-carboxylic acid ethyl ester (774 mg, 2.44 mmol), CuO (99 mg, 1.25 mmol) and NaOMe (540 mg, 10 mmol) in methanol (3 mL) is refluxed for 76 h. The mixture is diluted with ether (75 mL) and extracted with 1 N aq. NaOH (2×30 mL). The aq. extracts are acidified with 2 N aq. HCl (75 mL) and extracted with DCM (3×50 mL). The organic extracts are dried (Na₂SO₄), filtered and evaporated to provide crude 3-methoxy-5,5-dimethyl-4,5,6,7-tetrahydro-benzo[c]thiophene-1-carboxylic acid (262 mg). This material is dissolved in dry diethyl ether (10 mL) and methyllithium (0.7 mL, 1.6 N in diethyl ether) is added slowly at room temperature. After 15 min, the mixture is diluted with diethyl ether (50 mL), extracted with 1 N aq. NaOH (2×5 mL), dried (Na$_2$SO$_4$), filtered and evaporated. The crude product is purified by CC on silica gel eluting with heptane/EA to provide 1-(3-methoxy-5,5-dimethyl-4,5,6,7-tetrahydro-benzo[c]thiophen-1-yl)-ethanone (44 mg) as a yellow oil; LC-MS: $t_R$=1.03 min, [M+1]=239.30; $^1$H NMR (CDCl$_3$): δ 3.96 (s, 3H), 2.98 (t, J=6.4 Hz, 2H), 2.41 (s, 3H), 2.26 (s, 2H), 1.53 (t, J=6.4 Hz, 2H), 0.95 (s, 6H).

Example V

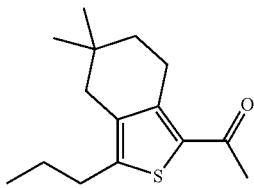

1-(5,5-Dimethyl-3-propyl-4,5,6,7-tetrahydro-benzo[c]thiophen-1-yl)-ethanone is prepared in analogy to Example R from Example F; LC-MS: $t_R$=1.13 min, [M+1]=251.25; $^1$H NMR (CDCl$_3$): δ 3.03 (t, J=7.0 Hz, 2H), 2.68 (t, J=7.6 Hz, 2H), 2.46 (s, 3H), 2.30 (s, 2H), 1.65 (hept, J=7.0 Hz, 2H), 1.54 (t, J=6.4 Hz, 2H), 0.99 (t, J=7.0 Hz, 3H), 0.96 (s, 6H).

Example W

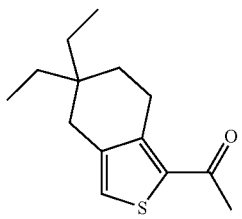

1-(5,5-Diethyl-4,5,6,7-tetrahydro-benzo[c]thiophen-1-yl)-ethanone is prepared in analogy to Example R from Example M; LC-MS: $t_R$=1.09 min, [M+1+CH$_3$CN]=278.22.

Example X

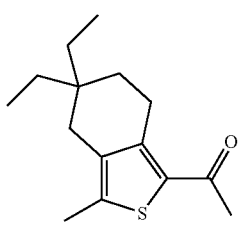

1-(5,5-Diethyl-3-methyl-4,5,6,7-tetrahydro-benzo[c]thiophen-1-yl)-ethanone is prepared from Example M in analogy to the procedures given for Example C and Q; LC-MS: $t_R$=1.03 min, [M+1+CH$_3$CN]=294.27.

Example Y

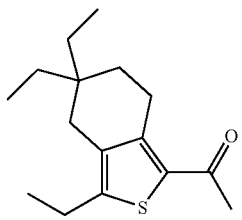

1-(3,5,5-Triethyl-4,5,6,7-tetrahydro-benzo[c]thiophen-1-yl)-ethanone is prepared from Example M in analogy to the procedures given for Example E and R; LC-MS: $t_R$=1.16 min, [M+1]=265.24; $^1$H NMR (CD$_3$OD): δ 2.94 (t, J=7.0 Hz, 2H), 2.75 (q, J=7.6 Hz, 2H), 2.44 (s, 3H), 2.33 8 s, 2H), 1.58 (t, J=6.4 Hz, 2H), 1.40-1.20 (m, 4H), 0.84 (t, J=7.6 Hz, 6H).

Example Z

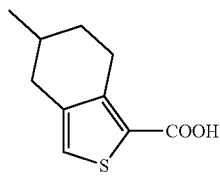

5-Methyl-4,5,6,7-tetrahydro-benzo[c]thiophene-1-carboxylic acid is prepared starting from 4-methylcyclohexanone following the procedures given in Example A; LC-MS: $t_R$=0.92 min; $^1$H NMR (CD$_3$OD): δ 7.18 (s, 1H), 3.25 (dd, J=2.9, 5.8 Hz, 1H), 2.86-2.70 (m, 2H), 2.22 (dd, J=10.6, 15.8 Hz, 1H), 1.95-1.85 (m, 1H), 1.83-1.70 (m, 1H), 1.34 (ddt, J$_d$=5.9, 13.5 Hz, J$_t$=11.1 Hz, 1H), 1.05 (d, J=6.4 Hz, 3H).

Example AA

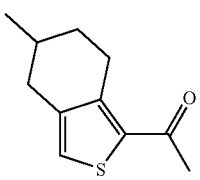

Treatment of Example Z with MeLi in analogy to the procedure described for Example P affords 1-(5-methyl-4,5,6,7-tetrahydro-benzo[c]thiophen-1-yl)-ethanone; LC-MS: $t_R$=1.00 min, [M+1]$^+$=195.23; $^1$H NMR (CDCl$_3$): δ 7.07 (s, 1H), 3.30 (ddd, J=2.9, 5.8, 18.8 Hz, 1H), 2.90-2.75 (m, 2H), 2.49 (s, 3H), 2.25 (dd, J=10.6, 15.8 Hz, 1H), 1.95-1.70 (m, 2H), 1.42-1.27 (m, 1H), 1.05 (d, J=6.4 Hz, 3H).

Example AB

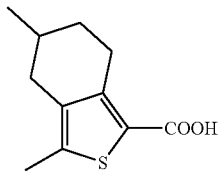

Alkylation of Example Z with methyliodide following the procedure described for Example C affords 3,5-dimethyl-4,5,6,7-tetrahydro-benzo[c]thiophene-1-carboxylic acid; LC-MS: $t_R$=0.95 min, [M+1+CH$_3$CN]$^+$=252.20.

Example AC

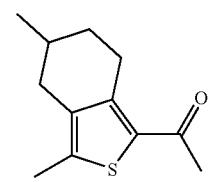

Treatment of Example AB with MeLi in analogy to the procedure described for Example P affords 1-(3,5-dimethyl-4,5,6,7-tetrahydro-benzo[c]thiophen-1-yl)-ethanone; LC-MS: $t_R$=1.03 min, [M+1]$^+$=209.11; $^1$H NMR (CDCl$_3$): δ 3.30 (ddd, J=2.9, 5.3, 18.8 Hz, 1H), 2.90-2.63 (m, 2H), 2.45 (s, 3H), 2.24 (s, 3H), 2.03 (d, J=10.6, 15.8 Hz, 1H), 1.92-1.68 (m, 2H), 1.36-1.20 (m, 1H), 1.07 (d, J=6.4 Hz, 3H).

Example AD

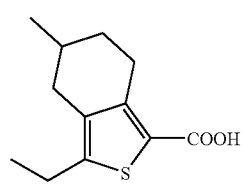

Alkylation of Example Z with ethyliodide following the procedure described for Example E affords 3-ethyl-5-methyl-4,5,6,7-tetrahydro-benzo[c]thiophene-1-carboxylic acid; LC-MS: $t_R$=0.99 min, [M+1+CH$_3$CN]$^+$=266.34.

Example AE

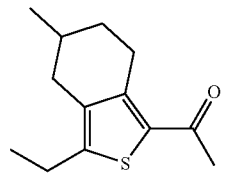

Treatment of Example AD with MeLi in analogy to the procedure described for Example P affords 1-(3-ethyl-5-methyl-4,5,6,7-tetrahydro-benzo[c]thiophen-1-yl)-ethanone; LC-MS: $t_R$=1.06 min, [M+1]$^+$=223.16.

Example AF

5-Ethyl-4,5,6,7-tetrahydro-benzo[c]thiophene-1-carboxylic acid is prepared starting from 4-ethylcyclohexanone following the procedures given in Example A; $^1$H NMR (CDCl$_3$): δ 7.16 (s, 1H), 3.34 (ddd, J=3.5, 5.3, 18.8 Hz, 1H), 2.91-2.72 (m, 2H), 2.26 (dd, J=10.6, 15.8 Hz, 1H), 2.00-1.90 (m, 1H), 1.64-1.50 (m, 1H), 1.48-1.22 (m, 3H), 0.97 (t, J=7.0 Hz, 3H).

Example AG

Treatment of Example AF with MeLi in analogy to the procedure described for Example P affords 1-(5-ethyl-4,5,6,7-tetrahydro-benzo[c]thiophen-1-yl)-ethanone; LC-MS: $t_R$=1.04 min, [M+1]$^+$=209.18.

Example AH

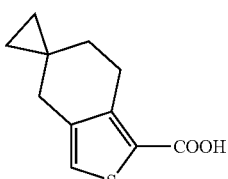

a) To a solution of 8-methylene-1,4-dioxa-spiro[4.5]decane (6.0 g, 39 mmol, prepared according to a literature procedure (K. C. Nicolaou, R. L. Magolda, D. A. Claremon, *J. Am. Chem. Soc.* 102 (1980) 1404-1409)) in toluene (10 mL), a solution of diethyl zinc (100 mL, 1 M in hexane) is added at −40 to −20° C. The mixture is stirred for 10 min before diiodoethane (53.6 g, 200 mmol) is added dropwise over a period of 20 min. The reaction is warmed to rt and stirring is continued for 18 h. The reaction mixture is poured onto ice-cooled sat. aq. NH$_4$Cl solution and extracted twice with diethyl ether. The combined organic extracts are washed with sat. aq. Na$_2$S$_2$O$_3$ and water, dried over Na$_2$SO$_4$, filtered and the solvent of the filtrate is evaporated to give 7,10-dioxa-dispiro[2.2.4.2]dodecane (12.35 g) as a colourless liquid containing approx. 20% of toluene (product volatile).

b) A solution of 7,10-dioxa-dispiro[2.2.4.2]dodecane (6.25 g, approx. 29 mmol) in THF (25 mL), water (20 mL) and TFA (10 mL) is stirred at rt for 2 h. The mixture is neutralized by adding 2 N aq. NaOH and sat. NaHCO$_3$ solution and extracted with diethyl ether. The organic extracts are washed with water, dried over Na$_2$SO$_4$, filtered and the solvent of the filtrate is removed to give spiro[2.5]octan-6-one (5.0 g) as a colourless oil containing remainders of toluene (product volatile). $^1$H NMR (CDCl$_3$): δ 2.14 (t, J=6.4 Hz, 4H), 1.40 (t, J=6.4 Hz, 4H), 0.21 (s, 4H).

c) 5,5-Ethylene-4,5,6,7-tetrahydro-benzo[c]thiophene-1-carboxylic acid is prepared by formulating, chlorinating and cyclising the above spiro[2.5]octan-6-one following the steps b), c) and d) described in Example A; LC-MS: t$_R$=0.91 min; $^1$H NMR (CDCl$_3$): δ 6.70 (s, 1H), 2.75 (t, J=6.4 Hz, 2H), 2.50 (s br, 1H), 2.21 (s, 2H), 1.23 (t, J=6.4 Hz, 2H), 0.10-0.00 (m, 4H).

Example AI

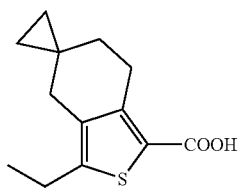

Alkylation of Example AH with ethyliodide following the procedure described for Example E affords 3-ethyl-5,5-ethylene-4,5,6,7-tetrahydro-benzo[c]thiophene-1-carboxylic acid; LC-MS: t$_R$=0.99 min, [M+1]$^+$=237.16.

Example AJ

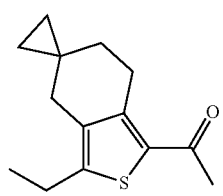

1-(3-Ethyl-5,5-ethylene-4,5,6,7-tetrahydro-benzo[c]thiophen-1-yl)-ethanone is prepared by treating Example AI with MeLi following the procedure given in Example P; LC-MS: t$_R$=1.07 min, [M+1]$^+$=235.22.

Example AK

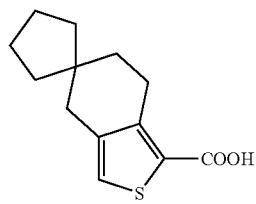

a) To a solution of spiro[4.5]dec-6-en-8-one (1.58 g, 10.5 mmol, prepared according to a literature procedure (N. R. Natale, R. O. Hutchins, *Org. Prep. Proc. Int.* 9 (1977) 103-108)) in EA (12 mL), Pd/C (75 mg, 10% Pd) is added. The mixture is stirred at rt under 1 bar of H$_2$ for 90 min before it is filtered over celite. The solvent of the filtrate is evaporated to give spiro[4.5]decan-8-one (1.56 g) as an almost colourless liquid; $^1$H NMR (CDCl$_3$): δ 2.36 (t, J=7.0 Hz, 4H), 1.75 (t, J=7.0 Hz, 4H), 1.70-1.65 (m, 4H), 1.62-1.50 (m, 4H).

b) The above spiro[4.5]decan-8-one is acylated, chlorinated and cyclized to 5,5-(1,4-butylene)-4,5,6,7-tetrahydro-benzo[c]thiophene-1-carboxylic acid following the steps b), c) and d) described in Example A; LC-MS: t$_R$=1.00 min; [M+1+CH$_3$CN]$^+$=278.23.

Example AL

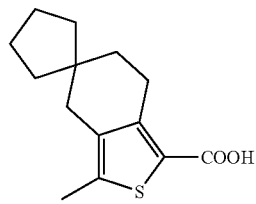

Alkylation of Example AJ with methyliodide following the procedure described for Example E affords 5,5-(1,4-butylene)-3-methyl-4,5,6,7-tetrahydro-benzo[c]thiophene-1-carboxylic acid; LC-MS: t$_R$=1.02 min, [M+1]$^+$=251.26.

Example AM

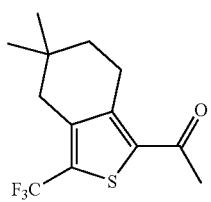

a) To a solution of 5,5-dimethyl-4,5,6,7-tetrahydro-benzo[c]thiophene-1-carboxylic acid (20 g, 95 mmol) in DMSO (150 mL) is added N,O-dimethylhydroxylamine hydrochloride (12.06 g, 124 mmol) and DIPEA (65 mL, 380 mmol), followed by TBTU (33.59 g, 105 mmol, dissolved in DMF (70 mL)). The reaction mixture is stirred at rt for 2 h before it is poured into water/ice and extracted twice with diethyl ether (2×100 mL). The organic extracts are washed with sat. aq. NaHCO$_3$ solution, 10% aq. citric acid solution and brine, dried over Na$_2$SO$_4$, filtered, evaporated and dried to give 5,5-dimethyl-4,5,6,7-tetrahydro-benzo[c]thiophene-1-carboxylic acid methoxy-methyl-amide (23 g) as a brown oil; LC-MS: $t_R$=1.01 min, [M+1]=254.14.

b) To a solution of diisopropylamine (11.02 g, 109 mmol) in THF (400 mL) is added n-butyl lithium (72.7 mL, 109 mmol, 1.5 M in pentane) at 0-5° C. The solution is cooled to −78° C. and a solution of 5,5-dimethyl-4,5,6,7-tetrahydro-benzo[c]thiophene-1-carboxylic acid methoxy-methyl-amide (23 g, 91 mmol) in THF (100 mL) is added. Upon complete addition, the mixture is stirred for 20 min at −78° C. before a solution of iodine (30 g, 119 mmol) in THF (100 mL) is added. Stirring is continued at −78° C. for 30 min. The reaction is quenched by slowly adding a 1:1 mixture of water/methanol (20 mL). The solution is diluted with water (400 mL) and extracted with diethyl ether (3×100 mL). The combined organic extracts are washed with 10% aq. citric acid solution and brine, dried over Na$_2$SO$_4$, filtered and evaporated. The crude product is purified by CC on silica gel eluting with DCM to afford 3-iodo-5,5-dimethyl-4,5,6,7-tetrahydro-benzo[c]thiophene-1-carboxylic acid methoxy-methyl-amide (18 g) as a brownish oil; LC-MS: $t_R$=1.09 min, [M+1]= 380.21.

c) 3-Iodo-5,5-dimethyl-4,5,6,7-tetrahydro-benzo[c]thiophene-1-carboxylic acid methoxy-methyl-amide (18 g, 47 mmol), CuI (14.5 g, 76 mmol) and KF (4.4 g, 76 mmol) are dissolved in DMF (80 mL). The solution is heated to 134° C. and methyl chlorodifluoroacetate (16.26 g, 113 mmol) is added via syringe pump over a period of 4 h. Gas evolution is observed. Upon complete addition, the mixture is cooled and poured into water/ice. The precipitate that forms is collected, suspended in DCM (600 mL), and filtered through a celite pad. The filtrate is washed with 0.5 N aq. HCl (250 mL), followed by sat. aq. NaHCO$_3$ solution, dried over Na$_2$SO$_4$, filtered and evaporated to give 5,5-dimethyl-3-trifluoromethyl-4,5,6,7-tetrahydro-benzo[c]thiophene-1-carboxylic acid methoxy-methyl-amide (14 g) as a brown oil; LC-MS: $t_R$=1.10 min, [M+1]=322.20.

d) A solution of 5,5-dimethyl-3-trifluoromethyl-4,5,6,7-tetrahydro-benzo[c]thiophene-1-carboxylic acid methoxy-methyl-amide (14 g, 44 mmol) in diethyl ether (400 mL) is treated at rt with methyl lithium (80 mL, 1.6 M in diethyl ether). Upon complete addition, the mixture is stirred at rt for 15 min before it is poured onto water/ice and neutralized with aq. HCl. The ether phase is separated and the aq. phase is extracted two more times with diethyl ether (2×100 mL). The organic extracts are washed with brine, dried over MgSO$_4$, filtered and evaporated. The crude product is purified by CC on silica gel eluting with heptane containing 20-30% of DCM to give 1-(5,5-dimethyl-3-trifluoromethyl-4,5,6,7-tetrahydro-benzo[c]thiophen-1-yl)-ethanone (9.1 g) as a yellow oil; LC-MS: $t_R$=1.11 min, [M+1+CH$_3$CN]=318.34; $^1$H NMR (CDCl$_3$): δ 3.04 (t, J=7.0 Hz, 2H), 2.57 (d, J=1.2 Hz, 2H), 2.53 (s, 3H), 1.58 (t, J=7.0 Hz, 2H), 0.99 (s, 6H).

Bromoketone 1

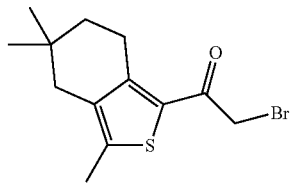

To a solution of 1-(3,5,5-trimethyl-4,5,6,7-tetrahydro-benzo[c]thiophen-1-yl)-ethanone (1.18 g, 5.31 mmol, Example C) in THF (60 mL) and methanol (6 mL), phenyltrimethylammonium bromide dibromide (2.0 g, 5.31 mmol) is added in portions. Upon complete addition, the mixture is stirred at rt for 30 min before the solvent is evaporated. The crude product is purified by prep. HPLC (Grom-Sil 120 ODS-4-HE, 30×75 mm, 10 µm, 20-95% acetonitrile in water containing 0.5% formic acid) to give 2-bromo-1-(3,5,5-trimethyl-4,5,6,7-tetrahydro-benzo[c]thiophen-1-yl)-ethanone (1.28 g) as a colourless oil; $^1$H NMR (CDCl$_3$): δ 4.24 (s, 2H), 3.03 (t, J=7.0 Hz, 2H), 2.36 (s, 3H), 2.30 (s, 2H), 1.54 (t, J=7.0 Hz, 2H), 0.98 (s, 6H).

Bromoketone 2

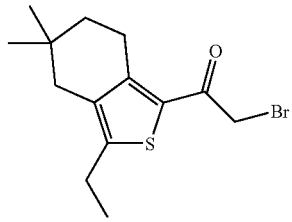

2-Bromo-1-(3-ethyl-5,5-dimethyl-4,5,6,7-tetrahydro-benzo[c]thiophen-1-yl)-ethanone is prepared from Example R in analogy to Bromoketone 1; LC-MS: $t_R$=1.12 min, [M+1]= 315.14; $^1$H NMR (CDCl$_3$): δ 4.27 (s, 2H), 3.04 (t, J=6.4 Hz, 2H), 2.75 (q, J=7.6 Hz, 2H), 2.30 (s, 2H), 1.56 (t, J=6.4 Hz, 2H), 1.29 (t, J=7.6 Hz, 3H), 0.97 (s, 6H).

Bromoketone 3

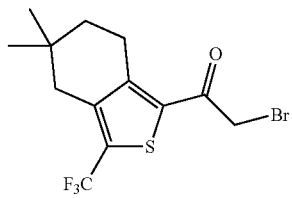

2-Bromo-1-(5,5-dimethyl-3-trifluoromethyl-4,5,6,7-tetrahydro-benzo[c]thiophen-1-yl)-ethanone is prepared from Example AM in analogy to Bromoketone 1; LC-MS: $t_R$=1.14 min, $^1$H NMR (CDCl$_3$): δ 4.28 (s, 2H), 3.06 (t, J=7.0 Hz, 2H), 2.59 (s, 2H), 1.60 (t, J=7.0 Hz, 2H), 0.99 (s, 6H).

Intermediate 1

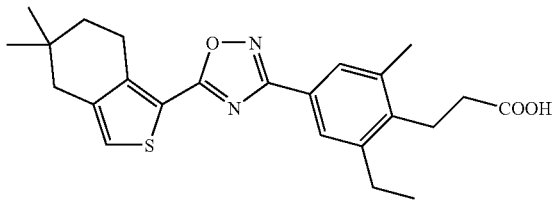

a) To a solution of 3,5-dimethyl-4,5,6,7-tetrahydro-benzo[c]thiophene-1-carboxylic acid (250 mg, 1.19 mmol) in DMF (3 mL), TBTU (381 mg, 1.19 mmol) and DIPEA (507 mg, 3.92 mmol) is added. The mixture is stirred at rt for 5 min before 3-[2-ethyl-4-(N-hydroxycarbamimidoyl)-6-methyl-phenyl]-propionic acid (298 mg, 1.19 mmol, Hydroxyamidine 3) dissolved in DMF (2 mL) is added. Stirring is continued at rt for 1 h. The mixture is diluted with formic acid (0.5 mL) and acetonitrile (5 mL) and separated by prep. HPLC (Grom-Sil 120 ODS-4-HE, 30×75 mm, 10 μm, 10-95% acetonitrile in water containing 0.5% formic acid) to afford 5,5-dimethyl-4,5,6,7-tetrahydro-benzo[c]thiophene-1-carboxylic acid N-(3-ethyl-5-methyl-4-(2-carboxy-ethyl)-N-hydroxybenzamidine)ester (170 mg) as a white solid; LC-MS: $t_R$=1.04 min, [M+1]=443.34.

b) A suspension of 5,5-dimethyl-4,5,6,7-tetrahydro-benzo[c]thiophene-1-carboxylic acid N-(3-ethyl-5-methyl-4-(2-carboxy-ethyl)-N-hydroxybenzamidine) ester (165 mg, 0.373 mmol) in toluene (250 mL) is stirred at 85° C. for 24 h and at 105° C. for 72 h before the solvent is removed in vacuo. The crude product is purified by prep. HPLC (Grom-Sil 120 ODS-4-HE, 30×75 mm, 10 μm, 70 to 100% acetonitrile in water containing 0.5% formic acid) to afford 3-{4-[5-(5,5-dimethyl-4,5,6,7-tetrahydro-benzo[c]thiophen-1-yl)-[1,2,4]oxadiazol-3-yl]-2-ethyl-6-methyl-phenyl}-propionic acid (100 mg) as a white solid; LC-MS: $t_R$=1.18 min, [M+1]=425.31.

Intermediate 2

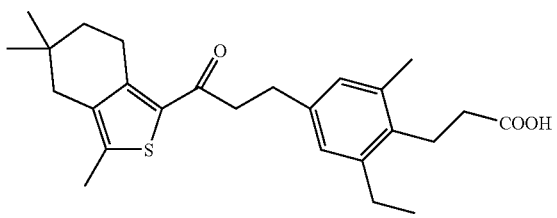

a) A solution of 1-(3,5,5-trimethyl-4,5,6,7-tetrahydro-benzo[c]thiophen-1-yl)-ethanone (355 mg, 1.55 mmol) and 3-(2-ethyl-4-formyl-6-methyl-phenyl)-acrylic acid (373 mg, 1.70 mmol, Aldehyde 5) in methanolic NaOH (8 mL, 10 g NaOH in 100 mL methanol) is stirred at rt for 3 h before it is carefully acidified to pH 1 by adding 2 N aq. HCl. The mixture is extracted twice with DCM, the organic extracts are washed with water and brine, dried over MgSO$_4$, filtered and evaporated. The crude product is crystallised from acetonitrile (120 mL) to give 3-{2-ethyl-6-methyl-4-[3-oxo-3-(3,5,5-trimethyl-4,5,6,7-tetrahydro-benzo[c]thiophen-1-yl)-propenyl]-phenyl}-acrylic acid (400 mg) as yellow crystals; LC-MS: $t_R$=1.17 min, [M+1]=423.34; $^1$H NMR (CDCl$_3$): δ 7.97 (d, J=16.4 Hz, 1H), 7.68 (d, J=15.2 Hz, 1H), 7.33 (s, 2H), 7.28 (d, J=15.8 Hz, 1H), 6.13 (d, J=15.8 Hz, 1H), 3.16 (t, J=7.0 Hz, 2H), 2.77 (q, J=7.6 Hz, 2H), 2.41 (s, 3H), 2.39 (s, 3H), 2.32 (s, 2H), 1.57 (t, J=6.4 Hz, 2H), 1.24 (t, J=7.6 Hz, 3H), 1.00 (s, 6H).

b) To a solution of 3-{2-ethyl-6-methyl-4-[3-oxo-3-(3,5,5-trimethyl-4,5,6,7-tetrahydro-benzo[c]thiophen-1-yl)-propenyl]-phenyl}-acrylic acid (340 mg, 0.805 mmol) and DIPEA (182 mg, 1.41 mmol) in ethanol, Pd/C (340 mg, 10% Pd, moistened with 50% water) is added and the resulting slurry is stirred at 50° C. for 72 h under 10 bar of H$_2$. Another portion of Pd/C is added and stirring is continued for 16 h at 50° C. under 10 bar of H$_2$. The reaction mixture is filtered and the filtrate is evaporated. The crude product is purified by prep. HPLC (Grom-Sil 120 ODS-4-HE, 30×75 mm, 10 μm, acetonitrile/water (0.5% HCOOH), 20% to 95% acetonitrile) to give 3-{2-ethyl-6-methyl-4-[3-oxo-3-(3,5,5-trimethyl-4,5,6,7-tetrahydro-benzo[c]thiophen-1-yl)-propyl]-phenyl}-propionic acid (154 mg) as a colourless foam; LC-MS: $t_R$=1.15 min, [M+1]=427.30.

Intermediate 3

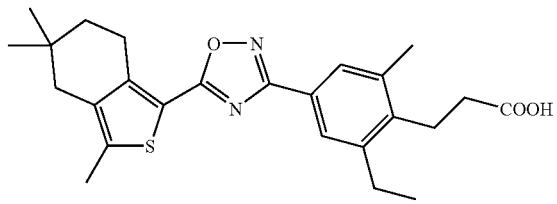

3-{2-Ethyl-6-methyl-4-[5-(3,5,5-trimethyl-4,5,6,7-tetrahydro-benzo[c]thiophen-1-yl)-[1,2,4]oxadiazol-3-yl]-phenyl}-propionic acid is prepared in analogy to Intermediate 1 using Example C and Hydroxyamidine 3; LC-MS: $t_R$=1.21 min, [M+1]=439.25; $^1$H NMR (D$_6$-DMSO): δ 12.25 (s, 1H), 7.66 (s br, 2H), 3.04 (t, J=6.4 Hz, 2H), 2.94-2.84 (m, 2H), 2.70 (q, J=7.6 Hz, 2H), 2.39-2.35 (m, 5H), 2.33 (s, 2H), 1.57 (t, J=7.0 Hz, 2H), 1.20 (t, J=7.6 Hz, 3H), 0.96 (s, 6H).

Intermediate 4

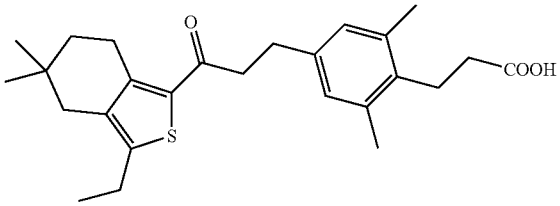

3-{4-[3-(3-Ethyl-5,5-dimethyl-4,5,6,7-tetrahydro-benzo[c]thiophen-1-yl)-3-oxo-propyl]-2,6-dimethyl-phenyl}-propionic acid (460 mg) is obtained as a colourless lyophilisate from 1-(3-ethyl-5,5-dimethyl-4,5,6,7-tetrahydro-benzo[c]thiophen-1-yl)-ethanone (400 mg, 1.69 mmol, Example R)

and 3-(4-formyl-2,6-dimethyl-phenyl)-propionic acid (419 mg, 2.03 mmol, Aldehyde 4) in analogy to Intermediate 2; LC-MS: $t_R$=1.15 min, [M+1]=427.40; $^1$H NMR (CDCl$_3$): δ 6.91 (s, 2H), 3.10-2.90 (m, 8H), 2.73 (q, J=7.6 Hz, 2H), 2.53-2.46 (m, 2H), 2.32 (s, 6H), 2.30 (s, 2H), 1.54 (t, J=7.0 Hz, 2H), 1.28 (t, J=7.6 Hz, 3H), 0.97 (s, 6H).

Intermediate 5

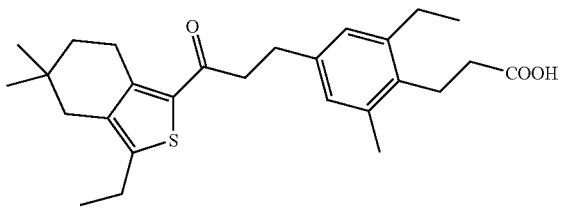

3-{2-Ethyl-4-[3-(3-ethyl-5,5-dimethyl-4,5,6,7-tetrahydro-benzo[c]thiophen-1-yl)-3-oxo-propyl]-6-methyl-phenyl}-propionic acid is prepared from 1-(3-ethyl-5,5-dimethyl-4,5,6,7-tetrahydro-benzo[c]thiophen-1-yl)-ethanone (Example R) and 3-(4-formyl-2-ethyl-6-methyl-phenyl)-propionic acid (Aldehyde 6) in analogy to Intermediate 2; LC-MS: $t_R$=1.16 min, [M+1]=441.36; $^1$H NMR (CDCl$_3$): δ 6.95 (s, 1H), 6.93 (s, 1H), 3.12-2.94 (m, 8H), 2.74 (q, J=7.6 Hz, 2H), 2.66 (q, J=7.6 Hz, 2H), 2.56-2.48 (m, 2H), 2.36 (s, 3H), 2.32 (s, 2H), 1.56 (t, J=7.0 Hz, 2H), 1.29 (t, J=7.6 Hz, 3H), 1.24 (t, J=7.6 Hz, 3H).

Intermediate 6

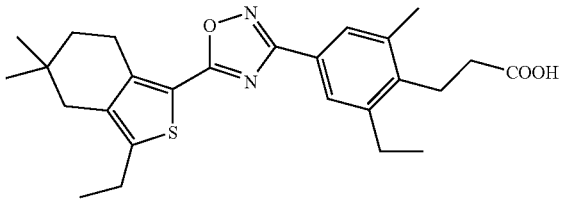

3-{2-Ethyl-6-methyl-4-[5-(3-ethyl-5,5-dimethyl-4,5,6,7-tetrahydro-benzo[c]thiophen-1-yl)-[1,2,4]oxadiazol-3-yl]-phenyl}-propionic acid is prepared in analogy to Intermediate 1 using Example E and Hydroxyamidine 3; LC-MS: $t_R$=1.24 min, [M+1]=453.29.

Intermediate 7

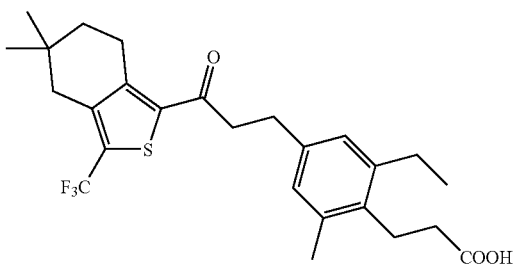

a) A solution of 1-(5,5-dimethyl-3-trifluoromethyl-4,5,6,7-tetrahydro-benzo[c]thiophen-1-yl)-ethanone (500 mg, 1.81 mmol) and 3-(2-ethyl-4-formyl-6-methyl-phenyl)-acrylic acid (395 mg, 1.81 mmol) in ethanol (25 mL) is treated with 5 N HCl in isopropanol (15 mL). The orange brown reaction mixture is stirred at 65° C. for 64 h. The mixture is diluted with sat. aq. NaHCO$_3$ solution and extracted twice with EA. The organic extracts are washed with sat. NaHCO$_3$ solution, dried over MgSO$_4$, filtered and the solvent of the filtrate is evaporated. The crude product is purified by CC on silica gel eluting with heptane:EA 9:1 to give 3-{4-[3-(5,5-dimethyl-3-trifluoromethyl-4,5,6,7-tetrahydro-benzo[c]thiophen-1-yl)-3-oxo-propenyl]-2-ethyl-6-methyl-phenyl}-acrylic acid ethyl ester (634 mg, contains traces of the corresponding isopropyl ester) as a colourless oil; LC-MS: $t_R$=1.32 min, [M+1]=505.04.

b) To a solution of 3-{4-[3-(5,5-dimethyl-3-trifluoromethyl-4,5,6,7-tetrahydro-benzo[c]thiophen-1-yl)-3-oxo-propenyl]-2-ethyl-6-methyl-phenyl}-acrylic acid ethyl ester (630 mg, 1.25 mmol) in ethanol (25 mL), a suspension of Pd/C (400 mg, 10% Pd) in ethanol (15 mL) is added and the resulting slurry is stirred at 65° C. for 16 h under 8 bar of H$_2$. The catalyst is filtered off and the solvent of the filtrate is evaporated. The residue is separated by CC on silica gel eluting with heptane:EA 4:1 to give 3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionic acid ethyl ester (340 mg, contains traces of the corresponding isopropyl ester) as a colourless oil; LC-MS: $t_R$=1.28 min, [M+1]=509.49.

c) A solution of 3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionic acid ethyl ester (340 mg, 0.668 mmol) in THF (5 mL), methanol (4 mL) and 2 N aq. LiOH (2 mL) is stirred at rt for 2 h before it is diluted with 10% aq. citric acid solution and extracted with DCM (3×75 mL). The combined organic extracts are dried over MgSO$_4$, filtered and the solvent of the filtrate is evaporated. The crude product is purified on prep. TLC plates with heptane:EA 3:4 to give 3-{4-[3-(5,5-dimethyl-3-trifluoromethyl-4,5,6,7-tetrahydro-benzo[c]thiophen-1-yl)-3-oxo-propyl]-2-ethyl-6-methyl-phenyl}-propionic acid (206 mg) as a colourless glass; LC-MS: $t_R$=1.17 min, [M+1]=481.36.

Method A

To a solution of the thiophene-2-carboxylic acid in DMF (approx. 15 mL/mmol), TBTU (1.3 eq.) and DIPEA (3 eq.) is added. The mixture is allowed to stand at rt for 2 h before the appropriate amine (2 eq.) is added. The mixture is allowed to stand at rt overnight and is then separated by prep. HPLC (Waters X-terra, 5 μm, 19×30 mm, gradient of acetonitrile in water containing 0.5% sat. aq. NH$_4$OH). The product containing fractions are lyophilised to give the desired amides as colourless lyophilisates or resins.

Examples 1 to 4

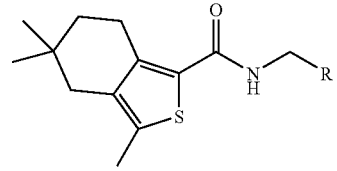

The following examples are prepared according to Method A and starting from 3,5,5-trimethyl-4,5,6,7-tetrahydro-benzo[c]thiophene-1-carboxylic acid:

| Example | R | Scale (μmol) | LC-MS t_R (min) | [M + H]+ |
|---|---|---|---|---|
| 1 | | 20 | 1.09 | 344.25 |
| 2 | | 20 | 1.09 | 374.24 |
| 3 | | 20 | 1.04 | 358.29 |
| 4 | | 20 | 1.00 | 360.27 |

Examples 5 to 8

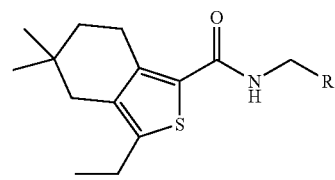

The following examples are prepared according to Method A and starting from 3-ethyl-5,5-dimethyl-4,5,6,7-tetrahydro-benzo[c]thiophene-1-carboxylic acid:

| Example | R | Scale (μmol) | LC-MS t_R (min) | [M + H]+ |
|---|---|---|---|---|
| 5 | | 20 | 1.11 | 358.28 |
| 6 | | 20 | 1.10 | 388.29 |
| 7 | | 20 | 1.06 | 372.30 |
| 8 | | 20 | 1.01 | 374.25 |

Examples 9 to 12

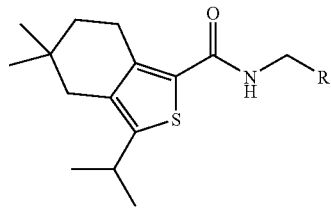

The following examples are prepared according to Method A and starting from 3-isopropyl-5,5-dimethyl-4,5,6,7-tetrahydro-benzo[c]thiophene-1-carboxylic acid:

| Example | R | Scale (μmol) | LC-MS t_R (min) | [M + H]+ |
|---|---|---|---|---|
| 9 | | 20 | 1.14 | 372.28 |
| 10 | | 20 | 1.12 | 402.22 |
| 11 | | 20 | 1.08 | 386.42 |
| 12 | | 20 | 1.03 | 388.31 |

Example 13

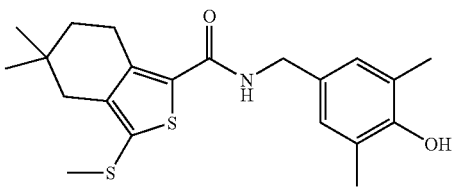

5,5-Dimethyl-3-methylsulfanyl-4,5,6,7-tetrahydro-benzo[c]thiophene-1-carboxylic acid 4-hydroxy-3,5-dimethyl-benzylamide is prepared starting from 5,5-dimethyl-3-methylsulfanyl-4,5,6,7-tetrahydro-benzo[c]thiophene-1-carboxylic acid according to Method A; LC-MS: $t_R$=1.07 min, [M+1]=390.2; $^1$H NMR (CDCl$_3$): δ 6.96 (s, 2H), 5.88 (t br, J=5 Hz, 1H), 4.69 (s, 1H), 4.45 (d, J=5.9 Hz, 2H), 2.95 (t, J=6.4 Hz, 2H), 2.44 (s, 3H), 2.37 (s, 2H), 2.24 (s, 6H), 1.54 (t, J=6.4 Hz, 2H), 0.97 (s, 6H).

Example 14

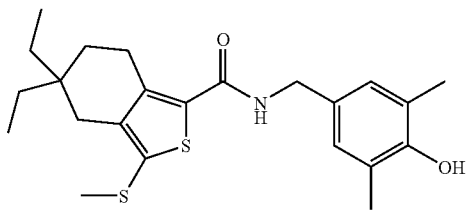

5,5-Diethyl-3-methylsulfanyl-4,5,6,7-tetrahydro-benzo[c]thiophene-1-carboxylic acid 4-hydroxy-3,5-dimethyl-benzylamide is prepared starting from 5,5-diethyl-3-methylsulfanyl-4,5,6,7-tetrahydro-benzo[c]thiophene-1-carboxylic acid according to Method A; LC-MS: $t_R$=1.12 min, [M+1]=418.2; $^1$H NMR (CDCl$_3$): δ 6.95 (s, 2H), 5.89 (t br, J=5 Hz, 1H), 4.75 (s, 1H), 4.44 (d, J=5.3 Hz, 2H), 2.90 (t, J=6.4 Hz, 2H), 2.43 (s, 3H), 2.36 (s, 2H), 2.23 (s, 6H), 1.55 (t, J=6.4 Hz, 2H), 1.40-1.19 (m, 4H), 0.82 (t, J=7.6 Hz, 6H).

Example 15

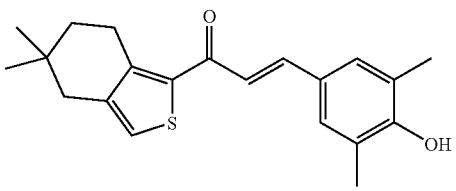

A solution of 1-(5,5-dimethyl-4,5,6,7-tetrahydro-benzo[c]thiophen-1-yl)-ethanone (1.00 g, 4.80 mmol) and 4-hydroxy-3,5-dimethyl-benzaldehyde (2.16 g, 14.4 mmol) in ethanol (10 mL) and 5 N HCl in isopropanol (5 mL) is stirred at 70° C. for 40 min. The dark solution is poured onto ice/sat. aq. NaHCO$_3$ and extracted with diethyl ether. The organic extract is washed with 1 N aq. NaOH and brine, and the solvent is removed in vacuo. The resulting oil is filtered over silica gel eluting with DCM, then DCM:TBME 10:1 to give 1-(5,5-dimethyl-4,5,6,7-tetrahydro-benzo[c]thiophen-1-yl)-3-(4-hydroxy-3,5-dimethyl-phenyl)-propenone (700 mg) as a yellow solid; LC-MS: $t_R$=1.14 min, [M+1]=341.23.

Example 16

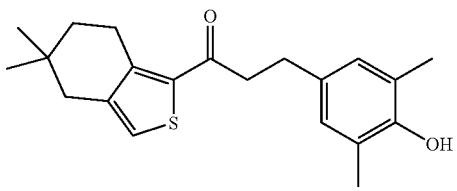

A solution of 1-(5,5-dimethyl-4,5,6,7-tetrahydro-benzo[c]thiophen-1-yl)-3-(4-hydroxy-3,5-dimethyl-phenyl)-propenone (1.60, 4.79 mmol) in ethanol (10 mL) is treated with Pd/C (500 mg, 10% Pd) and the resulting slurry is stirred at rt for 4 h under 1 bar of H$_2$. The catalyst is filtered off and the solvent of the filtrate is evaporated to give 1-(5,5-dimethyl-4,5,6,7-tetrahydro-benzo[c]thiophen-1-yl)-3-(4-hydroxy-3,5-dimethyl-phenyl)-propan-1-one (900 mg) as a beige resin.

Example 17 to 21

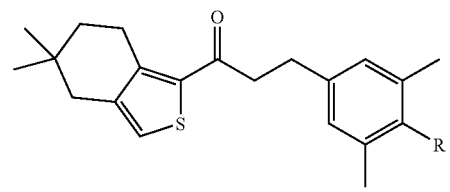

To a solution of 1-(5,5-dimethyl-4,5,6,7-tetrahydro-benzo[c]thiophen-1-yl)-3-(4-hydroxy-3,5-dimethyl-phenyl)-propan-1-one (10 mg, 30 μmol) in isopropanol (0.6 mL) and 2 N aq. NaOH (0.25 mL), the appropriate alkylating agent (as chloride, bromide or tosylate) is added (150 μmol) and the mixture is shaken at 70° C. for 5 h, then at rt for 16 h. The reaction mixture is separated by prep. HPLC (Waters X-terra, 5 μm, 19×30 mm, gradient of acetonitrile in water containing 0.5% formic acid).

Product fractions are lyophilised to give the desired products as a colourless resin or lyophilisate.

| | | | LC-MS | |
| --- | --- | --- | --- | --- |
| Example | R | Scale (μmol) | $t_R$ (min) | [M + H]$^+$ |
| 17 | -CH2OH) | 30 | 1.13 | 401.09 |
| 18 | | 30 | 1.12 | 401.14 |
| 19 | -CH2-O-CH3) | 30 | 1.12 | 431.31 |

-continued

| Example | R | Scale (μmol) | LC-MS $t_R$ (min) | [M + H]⁺ |
|---|---|---|---|---|
| 20 | 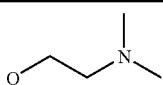 | 30 | 0.93 | 414.35 |
| 21 | 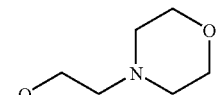 | 30 | 0.94 | 456.42 |

Example 22

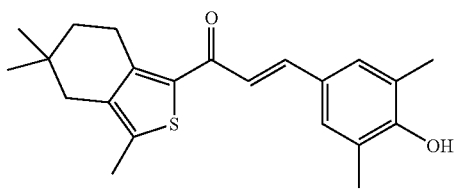

A solution of 1-(3,5,5-trimethyl-4,5,6,7-tetrahydro-benzo[c]thiophen-1-yl)-ethanone (1.35 g, 6.07 mmol) and 4-hydroxy-3,5-dimethyl-benzaldehyde (1.09 g, 7.29 mmol) in ethanol (20 mL) and 5 N HCl in isopropanol (10 mL) is stirred at rt for 100 min. The dark solution is diluted with diethyl ether (300 mL), washed with water followed by a 1:1 mixture of 1 N aq. NaOH and sat. aq. NaHCO₃, dried over MgSO₄ and evaporated. The crude product is purified by CC on silica gel eluting with heptane:EA 7:3 to give 3-(4-hydroxy-3,5-dimethyl-phenyl)-1-(3,5,5-trimethyl-4,5,6,7-tetrahydro-benzo[c]thiophen-1-yl)-propenone (1.86 g) as a yellow-orange solid; LC-MS: $t_R$=1.15 min, [M+1]=355.26; ¹H NMR (CDCl₃): δ 7.65 (d, J=15.2 Hz, 1H), 7.26 (s, 2H), 7.13 (d, J=15.2 Hz, 1H), 5.04 (s, 1H), 3.15 (t, J=6.4 Hz, 2H), 2.37 (s, 3H), 2.31 (s, 2H), 2.28 (s, 6H), 1.56 (t, J=6.4 Hz, 2H), 0.99 (s, 6H).

Example 23

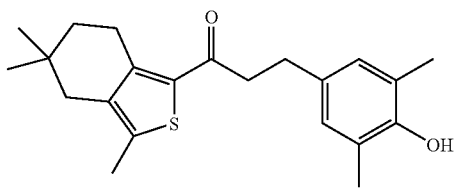

A solution of 3-(4-hydroxy-3,5-dimethyl-phenyl)-1-(3,5,5-trimethyl-4,5,6,7-tetrahydro-benzo[c]thiophen-1-yl)-propenone (1.86 g, 5.25 mmol) in THF (50 mL) and ethanol (50 mL) is treated with Pd/C (400 mg, 10% Pd) and the resulting slurry is stirred at rt for 5 h under 1.5 bar of H₂. The catalyst is filtered off and the solvent of the filtrate is evaporated. The crude product is purified by CC on silica gel eluting with heptane:EA 1:1 to give 3-(4-hydroxy-3,5-dimethyl-phenyl)-1-(3,5,5-trimethyl-4,5,6,7-tetrahydro-benzo[c]thiophen-1-yl)-propan-1-one (1.80 g) as a pale red foam; LC-MS: $t_R$=1.15 min, [M+1]=357.27; ¹H NMR (CDCl₃): δ 6.85 (s, 2H), 4.53 (s, 1H), 3.07-2.98 (m, 4H), 2.94-2.86 (m, 2H), 2.33 (s, 3H), 2.28 (s, 2H), 2.22 (s, 6H), 1.53 (t, J=7.0 Hz, 2H), 0.97 (s, 6H).

Examples 24 to 32

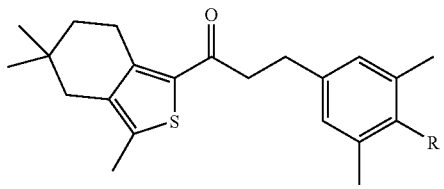

To a solution of 3-(4-hydroxy-3,5-dimethyl-phenyl)-1-(3,5,5-trimethyl-4,5,6,7-tetrahydro-benzo[c]thiophen-1-yl)-propan-1-one (11 mg, 30 μmol) in isopropanol (0.6 mL) and 2 N aq. NaOH (0.25 mL), the appropriate alkylating agent (as chloride, bromide or tosylate) is added (150 μmol) and the mixture is shaken at 70° C. for 5 h, then at rt for 16 h. The reaction mixture is separated by prep. HPLC (Waters X-terra, 5 μm, 19×30 mm, gradient of acetonitrile in water containing 0.5% formic acid). Product fractions are lyophilised to give the desired products as a colourless to pale yellow resin or lyophilisate.

| Example | R | Scale (μmol) | LC-MS $t_R$ (min) | [M + H]⁺ |
|---|---|---|---|---|
| 24 | 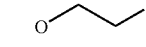 | 561 | 1.12 | 401.15 |
| 25 | 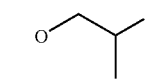 | 30 | 1.15 | 415.34 |
| 26 | 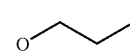 | 561 | 1.14 | 415.34 |
| 27 | 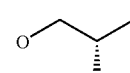 | 561 | 1.06 | 431.36 |
| 28 | 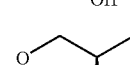 | 561 | 1.06 | 431.31 |
| 29 |  | 30 | 1.14 | 445.38 |
| 30 |  | 30 | 0.95 | 428.42 |
| 31 | 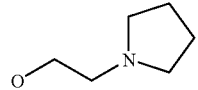 | 30 | 0.98 | 454.37 |

| Example | R | Scale (μmol) | LC-MS $t_R$ (min) | [M + H]⁺ |
|---|---|---|---|---|
| 32 | (morpholinoethoxy group) | 30 | 0.96 | 470.39 |

Example 27

¹H NMR (CDCl₃): δ 6.88 (s, 2H), 4.12-4.04 (m, 1H), 3.89-3.77 (m, 4H), 3.07-3.00 (m, 4H), 2.95-2.88 (m, 2H), 2.75 (s br, 1H), 2.33 (s, 3H), 2.28 (s, 2H), 2.26 (s, 6H), 1.53 (t, J=7.0 Hz, 2H), 0.97 (s, 6H).

Examples 33 to 42

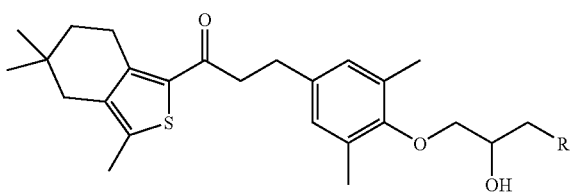

a) A solution of 3-(4-hydroxy-3,5-dimethyl-phenyl)-1-(3,5,5-trimethyl-4,5,6,7-tetrahydro-benzo[c]thiophen-1-yl)-propan-1-one (200 mg, 0.561 mmol) in isopropanol (5 mL) and 3 N aq. NaOH (2 mL) is treated with epichlorohydrine (210 mg, 1.68 mmol) and the mixture is stirred at rt for 6 h before it is diluted with diethyl ether, washed with sat. aq. NaHCO₃ solution followed by water, dried over MgSO₄ and evaporated. The crude product is purified on prep. TLC plates with heptane:EA 1:1 to give 3-(3,5-dimethyl-4-oxiranyl-methoxy-phenyl)-1-(3,5,5-trimethyl-4,5,6,7-tetrahydro-benzo[c]thiophen-1-yl)-propan-1-one (135 mg) as a yellow oil; LC-MS: $t_R$=1.19 min, [M+1]=413.26.

b) A solution of 3-(3,5-dimethyl-4-oxiranylmethoxy-phenyl)-1-(3,5,5-trimethyl-4,5,6,7-tetrahydro-benzo[c]thiophen-1-yl)-propan-1-one (7 mg, 18 μmol) in ethanol (1 mL) is treated with the appropriate amine (≧4 eq.). If the amine in addition contains a carboxylic acid functionality, water (500 μL) and DIPEA (20 μL) is added to the reaction mixture. The reaction mixture is stirred at 85° C. for 6 h before it is purified by prep. HPLC (Waters Xterra MS18 19×50 mm 5 μm, 10 to 95% acetonitrile in water containing 0.5% formic acid) to give the desired products as colourless to pale yellow resins.

| Example | R | Scale (μmol) | LC-MS $t_R$ (min) | [M + H]⁺ |
|---|---|---|---|---|
| 33 | NH₂ | 18 | 0.90 | 430.35 |
| 34 | NH—CH₃ | 18 | 0.92 | 444.26 |
| 35 | NH—CH₂CH₃ | 18 | 0.92 | 458.35 |
| 36 | NH—CH(CH₃)₂ | 18 | 0.94 | 472.78 |
| 37 | HN—CH₂CH₂—OH | 18 | 0.90 | 474.37 |
| 38 | HN—CH(CH₂OH)₂ | 18 | 0.90 | 504.43 |
| 39 | HN—CH₂CH₂—O—CH₂CH₃ | 18 | 0.98 | 516.47 |
| 40 | HN—CH₂CH₂—NH₂ | 18 | 0.82 | 473.49 |
| 41 | HN—CH₂CH₂—COOH | 18 | 0.92 | 502.42 |
| 42 | azetidine-3-carboxylic acid | 18 | 0.92 | 514.36 |

Example 43

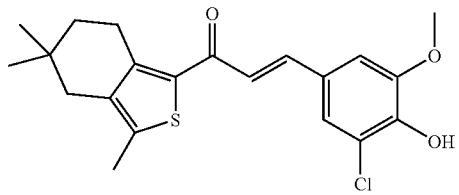

A solution of 1-(3,5,5-trimethyl-4,5,6,7-tetrahydro-benzo[c]thiophen-1-yl)-ethanone (1.35 g, 6.07 mmol) and 3-chloro-4-hydroxy-5-methoxy-benzaldehyde (1.36 g, 7.29 mmol) in ethanol (30 mL) and 5 N HCl in isopropanol (10 mL) is stirred at rt for 120 min. The dark solution is diluted with diethyl ether (200 mL), washed with water (2×200 mL), dried over MgSO₄ and evaporated. The crude product is purified by CC on silica gel eluting with heptane:EA 7:3 to give 3-(3-chloro-4-hydroxy-5-methoxy-phenyl)-1-(3,5,5-trimethyl-4,5,6,7-tetrahydro-benzo[c]thiophen-1-yl)-propenone (1.50 g) as a beige solid; LC-MS: $t_R$=1.15 min, [M+1]= 391.17; ¹H NMR (CDCl₃): δ 7.60 (d, J=15.2 Hz, 1H), 7.26 (s, 1H), 7.12 (d, J=15.2 Hz, 1H), 6.98 (d, J=1.2 Hz, 1H), 6.10 (s, 1H), 3.97 (s, 3H), 3.14 (t, J=7.0 Hz, 2H), 2.38 (s, 3H), 2.31 (s, 2H), 1.56 (t, J=7.0 Hz, 2H), 0.99 (s, 6H).

Example 44

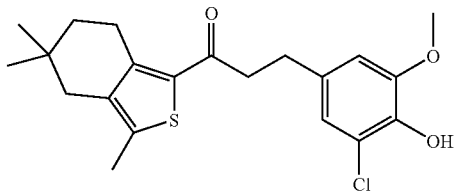

A solution of 3-(3-chloro-4-hydroxy-5-methoxy-phenyl)-1-(3,5,5-trimethyl-4,5,6,7-tetrahydro-benzo[c]thiophen-1-yl)-propenone (1.49 g, 3.80 mmol) in THF (50 mL) and ethanol (50 mL) is treated with Pd/C (300 mg, 10% Pd) and the resulting slurry is stirred at rt for 9 h under 1.5 bar of $H_2$. The catalyst is filtered off and the solvent of the filtrate is evaporated. The crude product is purified by CC on silica gel eluting with heptane:EA 1:1 to give 3-(4-hydroxy-3,5-dimethyl-phenyl)-1-(3,5,5-trimethyl-4,5,6,7-tetrahydro-benzo[c]thiophen-1-yl)-propan-1-one (1.80 g) as a pale red foam; LC-MS: $t_R$=1.12 min, [M+1]=393.18; $^1$H NMR (CDCl$_3$): δ 6.82 (d, J=1.8 Hz, 1H), 6.66 (d, J=1.8 Hz, 1H), 5.67 (s, 1H), 3.87 (s, 3H), 3.06-2.90 (m, 6H), 2.33 (s, 3H), 2.28 (s, 2H), 1.53 (t, J=6.4 Hz, 2H), 0.97 (s, 6H).

Example 45

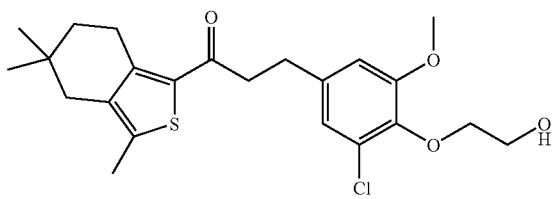

To a red solution of 3-(4-hydroxy-3,5-dimethyl-phenyl)-1-(3,5,5-trimethyl-4,5,6,7-tetrahydro-benzo[c]thiophen-1-yl)-propan-1-one (200 mg, 0.509 mmol) in isopropanol (8 mL) and 3 N aq. NaOH (2.5 mL), 2-bromoethanol (254 mg, 2.04 mmol) is added and the mixture is stirred at 70° C. for 20 h before another portion of 2-bromoethanol (254 mg, 2.04 mmol) is added. Stirring is continued at 70° C. for 7 h. The mixture is diluted with diethyl ether and twice washed with water. The organic layer is dried over MgSO$_4$ and evaporated. The crude product is purified on prep. TLC plates with heptane:EA 1:1 to give 3-[3-chloro-4-(2-hydroxy-ethoxy)-5-methoxy-phenyl]-1-(3,5,5-trimethyl-4,5,6,7-tetrahydro-benzo[c]thiophen-1-yl)-propan-1-one (160 mg) as a yellow oil; LC-MS: $t_R$=1.12 min, [M+1]=437.18; $^1$H NMR (CDCl$_3$): δ 6.86 (d, J=1.8 Hz, 1H), 6.71 (d, J=1.8 Hz, 1H), 4.17-4.10 (m, 2H), 3.85 (s, 3H), 3.84-3.75 (m, 2H), 3.08-2.94 (m, 7H), 2.33 (s, 3H), 2.28 (s, 2H), 1.53 (t, J=7.0 Hz, 2H), 0.97 (s, 6H).

Example 46

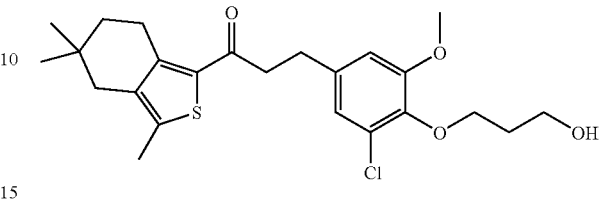

To a red solution of 3-(4-hydroxy-3,5-dimethyl-phenyl)-1-(3,5,5-trimethyl-4,5,6,7-tetrahydro-benzo[c]thiophen-1-yl)-propan-1-one (200 mg, 0.509 mmol) in isopropanol (8 mL) and 3 N aq. NaOH (2.5 mL), 3-bromopropanol (283 mg, 2.04 mmol) is added and the mixture is stirred at 70° C. for 5 h before another portion of 3-bromopropanol (142 mg, 1.02 mmol) is added. Stirring is continued at 70° C. for 18 h. The mixture is diluted with diethyl ether and twice washed with water. The organic layer is dried over MgSO$_4$ and evaporated. The crude product is purified on prep. TLC plates with heptane:EA 1:1 to give 3-[3-chloro-4-(3-hydroxy-propoxy)-5-methoxy-phenyl]-1-(3,5,5-trimethyl-4,5,6,7-tetrahydro-benzo[c]thiophen-1-yl)-propan-1-one (170 mg) as a yellow oil; LC-MS: $t_R$=1.13 min, [M+1]=451.19; $^1$H NMR (CDCl$_3$): δ 6.85 (d, J=1.8 Hz, 1H), 6.70 (d, J=1.8 Hz, 1H), 4.11 (t, J=5.9 Hz, 2H), 3.97-3.90 (m, 2H), 3.84 (s, 3H), 3.08-2.92 (s, 6H), 2.55 (t br, J=5 Hz, 1H), 2.33 (s, 3H), 2.28 (s, 2H), 2.00 (p, J=5.9 Hz, 2H), 1.53 (t, J=7.0 Hz, 2H), 0.97 (s, 6H).

Examples 45 to 53

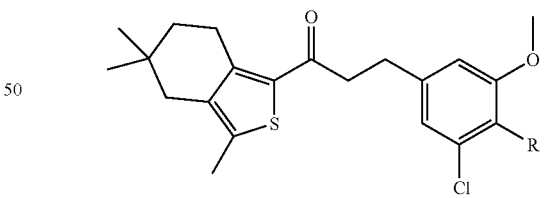

To a solution of 3-(4-hydroxy-3,5-dimethyl-phenyl)-1-(3,5,5-trimethyl-4,5,6,7-tetrahydro-benzo[c]thiophen-1-yl)-propan-1-one (8 mg, 20 μmol) in isopropanol (0.6 mL) and 2 N aq. NaOH (0.25 mL), the appropriate alkylating agent (as chloride, bromide or tosylate) is added (150 μmol) and the mixture is shaken at 70° C. for 5 h. The reaction mixture is separated by prep. HPLC (Waters X-terra, 5 μm, 19×30 mm, gradient of acetonitrile in water containing 0.5% formic acid or 0.74% diethylamine). Product fractions are lyophilised to give the desired products as a colourless to pale yellow resin or lyophilisate.

| Example | R | Scale (μmol) | LC-MS $t_R$ (min) | [M + H]$^+$ |
|---------|---|--------------|-------------------|-------------|
| 45 | (structure: O-CH2-CH2-OH) | 20 | 1.12 | 437.31 |
| 46 | (structure: O-CH2-CH2-CH2-OH) | 20 | 1.13 | 451.28 |
| 47 | (structure: O-CH2-CH(OH)-CH3) | 20 | 1.15 | 451.30 |
| 48 | (structure: O-CH2-CH(OH)-CH2-OH, stereo) | 20 | 1.05 | 467.32 |
| 49 | (structure: O-CH2-CH(OH)-CH2-OH, stereo) | 20 | 1.05 | 467.36 |
| 50 | (structure: O-CH2-CH(OH)-CH2-OMe) | 20 | 1.13 | 481.38 |
| 51 | (structure: O-CH2-CH2-N(CH3)2) | 20 | 0.95 | 464.38 |
| 52 | (structure: O-CH2-CH2-pyrrolidinyl) | 20 | 0.98 | 490.36 |
| 53 | (structure: O-CH2-CH2-morpholinyl) | 20 | 0.95 | 506.32 |

Examples 54 to 63

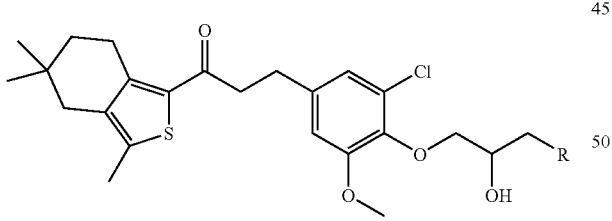

a) A solution of 3-(4-hydroxy-3,5-dimethyl-phenyl)-1-(3,5,5-trimethyl-4,5,6,7-tetrahydro-benzo[c]thiophen-1-yl)-propan-1-one (200 mg, 0.509 mmol) in isopropanol (5 mL) and 3 N aq. NaOH (2 mL) is treated with epichlorohydrine (191 mg, 1.53 mmol) and the mixture is stirred at rt for 4 h then at 50° C. for 6 h before it is diluted with diethyl ether, washed with sat. aq. NaHCO$_3$ solution followed by water, dried over MgSO$_4$ and evaporated. The crude product is purified on prep. TLC plates with heptane:EA 7:3 to give 3-(3-chloro-5-methoxy-4-oxiranylmethoxy-phenyl)-1-(3,5,5-trimethyl-4,5,6,7-tetrahydro-benzo[c]thiophen-1-yl)-propan-1-one (80 mg) as a yellow oil; LC-MS: $t_R$=1.17 min, [M+1]= 449.17.

b) A solution of 3-(3-chloro-5-methoxy-4-oxiranylmethoxy-phenyl)-1-(3,5,5-trimethyl-4,5,6,7-tetrahydro-benzo[c]thiophen-1-yl)-propan-1-one (8 mg, 18 μmol) in ethanol (1 mL) is treated with the appropriate amine (≧4 eq.). If the amine in addition contains a carboxylic acid functionality, water (500 μL) and DIPEA (20 μL) is added to the reaction mixture. The reaction mixture is stirred at 85° C. for 6 h before it is purified by prep. HPLC (Waters Xterra MS18 19×50 mm 5 μm, 10 to 95% acetonitrile in water containing 0.5% formic acid) to give the desired products as colourless to pale yellow resins.

| Example | R | Scale (μmol) | LC-MS $t_R$ (min) | [M + H]$^+$ |
|---------|---|--------------|-------------------|-------------|
| 54 | NH$_2$ | 18 | 0.90 | 466.32 |
| 55 | NH—CH$_3$ | 18 | 0.92 | 480.39 |
| 56 | NH—CH$_2$CH$_3$ | 18 | 0.94 | 494.34 |
| 57 | NH—CH(CH$_3$)$_2$ | 18 | 0.95 | 508.44 |
| 58 | (HN-CH2-CH2-OH) | 18 | 0.90 | 510.40 |
| 59 | (HN-CH(CH2OH)2) | 18 | 0.89 | 540.38 |
| 60 | (HN-CH2-CH2-CH2-O-Et) | 18 | 0.97 | 552.47 |
| 61 | (HN-CH2-CH2-NH2) | 18 | 0.81 | 509.38 |
| 62 | (HN-CH2-CH2-COOH) | 18 | 0.91 | 538.32 |
| 63 | (azetidine-3-carboxylic acid) | 18 | 0.92 | 550.36 |

Example 64

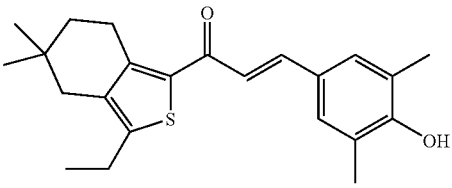

A solution of 1-(3-ethyl-5,5-dimethyl-4,5,6,7-tetrahydro-benzo[c]thiophen-1-yl)-ethanone (1.80 g, 7.62 mmol) and 3,5-dimethyl-4-hydroxybenzaldehyde (2.10 g, 14.0 mmol) in ethanol (20 mL) and 5 N HCl in isopropanol (5 mL) is stirred at 70° C. for 40 min. The dark violet to brown solution is poured onto 1 N aq. NaOH/ice and extracted with EA. The organic extract is washed four times with 1 N aq. NaOH, once with 10% aq. citric acid solution and brine, and the solvent is removed in vacuo. The crude product is purified by filtration over silica gel eluting with DCM to give 1-(3-ethyl-5,5-dimethyl-4,5,6,7-tetrahydro-benzo[c]thiophen-1-yl)-3-(4-hydroxy-3,5-dimethyl-phenyl)-propenone (2.40 g) as a brown solid; LC-MS: $t_R$=1.18 min, [M+1]=369.19; $^1$H NMR (CDCl$_3$): δ 7.66 (d, J=15.2 Hz, 1H), 7.17 (d, J=15.2 Hz, 1H), 3.16 (t, J=7.0 Hz, 2H), 2.77 (q, J=7.6 Hz, 2H), 2.34 8 s, 3H), 2.28 8 s, 8H), 1.57 (t, J=7.0 Hz, 2H), 1.31 (t, 7.6 Hz, 3H), 0.99 (s, 6H).

Example 65

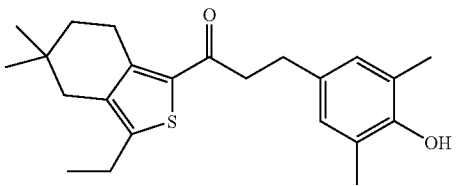

A solution of 1-(3-ethyl-5,5-dimethyl-4,5,6,7-tetrahydro-benzo[c]thiophen-1-yl)-3-(4-hydroxy-3,5-dimethyl-phenyl)-propenone (2.40 g, 6.51 mmol) in ethanol (10 mL) is treated with a suspension of Pd/C (1.70 g, 10% Pd) in ethanol and the mixture is stirred at rt for 18 h under 1 atm H$_2$. The mixture is filtered and the filtrate is evaporated to give 1-(3-ethyl-5,5-dimethyl-4,5,6,7-tetrahydro-benzo[c]thiophen-1-yl)-3-(4-hydroxy-3,5-dimethyl-phenyl)-propan-1-one (2.00 g) as a brown oil; LC-MS: $t_R$=1.16 min, [M+1]=371.25.

Examples 66 to 74

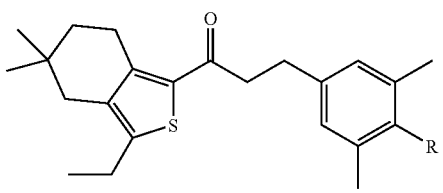

To a solution of 1-(3-ethyl-5,5-dimethyl-4,5,6,7-tetrahydro-benzo[c]thiophen-1-yl)-3-(4-hydroxy-3,5-dimethyl-phenyl)-propan-1-one (11 mg, 30 μmol) in isopropanol (0.6 mL) and 2 N aq. NaOH (0.25 mL), the appropriate alkylating agent (as chloride, bromide or tosylate) is added (150 μmol) and the mixture is shaken at 70° C. for 5 h, then at rt for 16 h. The reaction mixture is separated by prep. HPLC (Waters X-terra, 5 μm, 19×30 mm, gradient of acetonitrile in water containing 0.5% formic acid). Product fractions are lyophilised to give the desired products as a colourless to pale yellow resin or lyophilisate.

| | | | LC-MS | |
|---|---|---|---|---|
| Example | R | Scale (μmol) | $t_R$ (min) | [M + H]$^+$ |
| 66 | –O–CH$_2$CH$_2$–OH | 30 | 1.15 | 415.38 |
| 67 | –O–CH$_2$–CH(OH)–CH$_3$ | 30 | 1.17 | 429.37 |
| 68 | –O–CH$_2$CH$_2$CH$_2$–OH | 30 | 1.17 | 429.31 |
| 69 | –O–CH$_2$–CH(OH)–CH$_2$OH (S) | 560 | 1.08 | 445.28 |
| 70 | –O–CH$_2$–CH(OH)–CH$_2$OH (R) | 560 | 1.08 | 445.28 |
| 71 | –O–CH$_2$–CH(OH)–CH$_2$–OCH$_3$ | 30 | 1.16 | 459.30 |
| 72 | –O–CH$_2$CH$_2$–N(CH$_3$)$_2$ | 30 | 0.97 | 442.30 |
| 73 | –O–CH$_2$CH$_2$–(pyrrolidin-1-yl) | 30 | 1.00 | 468.41 |
| 74 | –O–CH$_2$CH$_2$–(morpholin-4-yl) | 30 | 0.97 | 484.42 |

Example 69

$^1$H NMR (CDCl$_3$): δ 6.88 (s, 2H), 4.13-4.03 (m, 1H), 3.90-3.76 (m, 4H), 3.09-3.00 (m, 4H), 2.96-2.88 (m, 2H), 2.79-2.67 (m, 3H), 2.30 (s, 2H), 2.25 (s, 6H), 2.14 (t, J=5.9 Hz, 1H), 1.54 (t, J=7.0 Hz, 2H), 1.27 (t, J=7.6 Hz, 3H), 0.96 (s, 6H).

Examples 75 to 80

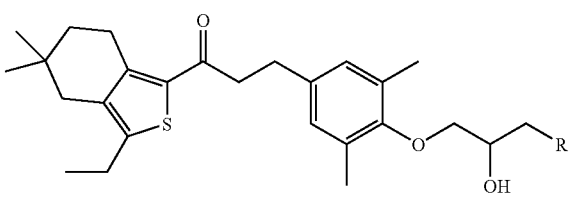

a) A solution of 1-(3-ethyl-5,5-dimethyl-4,5,6,7-tetrahydro-benzo[c]thiophen-1-yl)-3-(4-hydroxy-3,5-dimethyl-phenyl)-propan-1-one (75 mg, 0.20 mmol) in isopropanol (4 mL) and 3 N aq. NaOH (1.7 mL) is treated with epichlorohydrine (75 mg, 0.60 mmol) and the mixture is stirred at rt for 1 h. The mixture is diluted with acetonitrile (1 mL) and separated by prep. HPLC (Phenomenex Aqua, 75×30 mm ID, 10 μm, 10-95% acetonitrile in water containing 0.5% formic acid) to give 3-(3,5-dimethyl-4-oxiranylmethoxy-phenyl)-1-(3-ethyl-5,5-dimethyl-4,5,6,7-tetrahydro-benzo[c]thiophen-1-yl)-propan-1-one (50 mg) as a colourless resin; LC-MS: $t_R$=1.21 min, [M+1]=427.41.

b) A solution of 3-(3,5-dimethyl-4-oxiranylmethoxy-phenyl)-1-(3-ethyl-5,5-dimethyl-4,5,6,7-tetrahydro-benzo[c]thiophen-1-yl)-propan-1-one (6 mg, 15 μmol) in ethanol (1 mL) is treated with the appropriate amine (≧4 eq.). If the amine in addition contains a carboxylic acid functionality, water (500 μL) and DIPEA (20 μL) is added to the reaction mixture. The reaction mixture is stirred at 85° C. for 5 h before it is purified by prep. HPLC (Waters Xterra MS18 19×50 mm 5 μm, 10 to 95% acetonitrile in water containing 0.5% formic acid) to give the desired products as colourless to pale yellow resins.

| Example | R | Scale (μmol) | LC-MS $t_R$ (min) | [M + H]⁺ |
|---|---|---|---|---|
| 75 | NH—CH(CH₃)₂ | 15 | 0.98 | 486.50 |
| 76 | 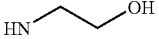 | 15 | 0.93 | 488.51 |
| 77 |  | 15 | 0.93 | 518.45 |
| 78 | 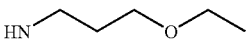 | 15 | 1.01 | 530.41 |
| 79 | 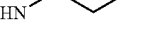 | 15 | 0.85 | 487.47 |
| 80 | 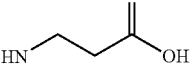 | 15 | 0.95 | 516.40 |

Example 81

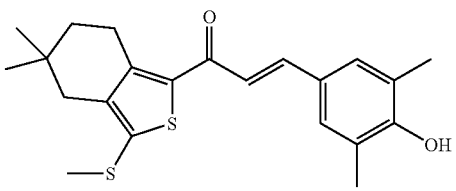

A solution of 1-(5,5-dimethyl-3-methylsulfanyl-4,5,6,7-tetrahydro-benzo[c]thiophen-1-yl)-ethanone (214 mg, 0.842 mmol) and 3,5-dimethyl-4-hydroxybenzaldehyde (150 mg, 0.99 mmol) in ethanol (1.5 mL) and 5 N HCl in isopropanol (0.5 mL) is stirred at rt for 16 h before it is diluted with diethyl ether, washed with brine, dried over Na₂SO₄ and evaporated. The crude product is purified by CC on silica gel eluting with hexane:EA 3:1. The solvent of the product containing fractions is evaporated and the product is crystallised from chloroform/pentane to give 1-(5,5-diethyl-3-methylsulfanyl-4,5,6,7-tetrahydro-benzo[c]thiophen-1-yl)-3-(4-hydroxy-3,5-dimethyl-phenyl)-propenone (12 mg) as a yellow solid; LC-MS: $t_R$=1.17 min, [M+1]=387.2; ¹H NMR (CDCl₃): δ 7.66 (d, J=15.2 Hz, 1H), 7.26 (s, 2H), 7.12 (d, J=15.2 Hz, 1H), 5.07 (s br, 1H), 3.15 (t, J=6.4 Hz, 2H), 2.57 (s, 3H), 2.36 8 s, 2H), 2.28 8 s, 6H), 1.57 (t, J=6.4 Hz, 2H), 1.00 (s, 6H).

Example 82

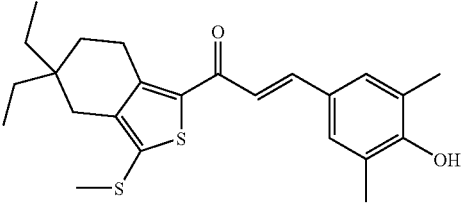

A solution of 1-(5,5-diethyl-3-methylsulfanyl-4,5,6,7-tetrahydro-benzo[c]thiophen-1-yl)-ethanone (458 mg, 1.62 mmol) and 3,5-dimethyl-4-hydroxybenzaldehyde (251 mg, 1.67 mmol) in ethanol (5 mL) and 5 N HCl in isopropanol (3.5 mL) is stirred at rt for 16 h before it is diluted with diethyl ether, washed with brine, dried over Na₂SO₄ and evaporated. The crude product is purified by CC on silica gel eluting with hexane:EA 1:1 to give 1-(5,5-diethyl-3-methylsulfanyl-4,5,6,7-tetrahydro-benzo[c]thiophen-1-yl)-3-(4-hydroxy-3,5-dimethyl-phenyl)-propenone (113 mg) as a yellow resin; LC-MS: $t_R$=1.22 min, [M+1]=415.2; ¹H NMR (CDCl₃): δ 7.65 (d, J=15.2 Hz, 1H), 7.26 (s, 2H), 7.11 (d, J=15.2 Hz, 1H), 5.03 (s, 1H), 3.10 (t, J=6.4 Hz, 2H), 2.57 (s, 3H), 2.35 (s, 2H), 2.29 (s, 6H), 1.59 (t, J=6.4 Hz, 2H), 1.40-1.22 (m, 4H), 0.85 (t, J=7.6 Hz, 6H).

Examples 83 to 89

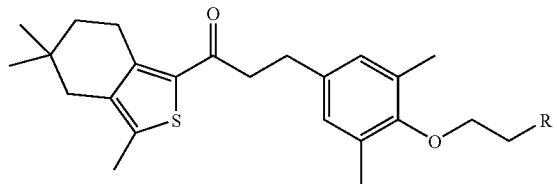

a) To a solution of 3-[4-(2-hydroxy-ethoxy)-3,5-dimethyl-phenyl]-1-(3,5,5-trimethyl-4,5,6,7-tetrahydro-benzo[c]thiophen-1-yl)-propan-1-one (130 mg, 0.325 mmol) in DCM (10 mL) and DIPEA (0.09 mL, 0.52 mmol) is added methane sulfonylchloride (0.03 mL, 0.39 mmol) at 0° C. The reaction mixture is stirred at 0° C. for 30 min. The reaction mixture is diluted with DCM, washed with 0.1 N aq. NaOH followed by 10% aq. citric acid solution, dried over MgSO₄ and evaporated to give methanesulfonic acid 2-{2,6-dimethyl-4-[3-oxo-3-(3,5,5-trimethyl-4,5,6,7-tetrahydro-benzo[c]thiophen-1-yl)-propyl]-phenoxy}-ethyl ester (165 mg) as a yellow oil; LC-MS: $t_R$=1.17 min, [M+1]⁺=479.26.

b) A solution of methanesulfonic acid 2-{2,6-dimethyl-4-[3-oxo-3-(3,5,5-trimethyl-4,5,6,7-tetrahydro-benzo[c]thiophen-1-yl)-propyl]-phenoxy}-ethyl ester in DMF is treated with the appropriate amine (≧4 eq.) and DIPEA (≧4 eq.). The reaction mixture is stirred at 75° C. for 7 h before it is purified by prep. HPLC (Waters Symmetry C18 19×50 mm 5 μm, 10 to 95% acetonitrile in water containing 0.5% formic acid) to give the desired product as a colourless lyophilisate or resin.

| Example | R | Scale (μmol) | $t_R$ (min) LC-MS | $[M + H]^+$ |
|---|---|---|---|---|
| 83 | NH$_2$ | 15 | 0.92 | 399.96 |
| 84 | NHCH$_2$CH$_3$ | 15 | 0.96 | 428.45 |
| 85 | NHCH(CH$_3$)$_2$ | 15 | 0.98 | 442.44 |
| 86 | HN~~OH | 15 | 0.92 | 444.47 |
| 87 | HN~~OH, OH | 15 | 0.91 | 474.39 |
| 88 | HN~~NH$_2$ | 15 | 0.82 | 443.39 |
| 89 | piperazinyl-ethanol | 15 | 0.87 | 513.58 |

Examples 90 to 96

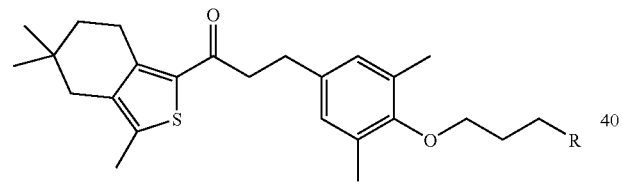

| Example | R | Scale (μmol) | $t_R$ (min) LC-MS | $[M + H]^+$ |
|---|---|---|---|---|
| 90 | NH$_2$ | 15 | 0.93 | 414.38 |
| 91 | NHCH$_2$CH$_3$ | 15 | 0.97 | 442.37 |
| 92 | NHCH(CH$_3$)$_2$ | 15 | 0.99 | 456.51 |
| 93 | HN~~OH | 15 | 0.93 | 458.38 |
| 94 | HN~~OH, OH | 15 | 0.92 | 488.46 |
| 95 | HN~~NH$_2$ | 15 | 0.83 | 457.45 |
| 96 | piperazinyl-ethanol | 15 | 0.86 | 527.49 |

Examples 97 to 104

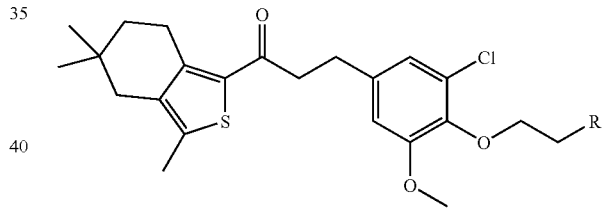

a) To a solution of 3-[4-(3-hydroxy-propoxy)-3,5-dimethyl-phenyl]-1-(3,5,5-trimethyl-4,5,6,7-tetrahydro-benzo[c]thiophen-1-yl)-propan-1-one (170 mg, 0.411 mmol) in DCM (10 mL) and DIPEA (0.15 mL, 0.89 mmol) is added methane sulfonylchloride (0.04 mL, 0.49 mmol) at 0° C. The reaction mixture is stirred at 0° C. for 30 min. The reaction mixture is diluted with DCM, washed with 0.1 N aq. NaOH followed by 10% aq. citric acid solution, dried over MgSO$_4$ and evaporated to give methanesulfonic acid 3-{2,6-dimethyl-4-[3-oxo-3-(3,5,5-trimethyl-4,5,6,7-tetrahydro-benzo[c]thiophen-1-yl)-propyl]-phenoxy}-propyl ester (200 mg) as a yellow oil; LC-MS: $t_R$=1.18 min, $[M+1]^+$=493.26.

b) A solution of methanesulfonic acid 3-{2,6-dimethyl-4-[3-oxo-3-(3,5,5-trimethyl-4,5,6,7-tetrahydro-benzo[c]thiophen-1-yl)-propyl]-phenoxy}-propyl ester in DMF is treated with the appropriate amine (≧4 eq.) and DIPEA (≧4 eq.). The reaction mixture is stirred at 75° C. for 7 h before it is purified by prep. HPLC (Waters Symmetry C18 19×50 mm 5 μm, 10 to 95% acetonitrile in water containing 0.5% formic acid) to give the desired product as a colourless lyophilisate or resin.

a) To a solution of 3-[3-chloro-4-(2-hydroxyethoxy)-5-methoxy-phenyl]-1-(3,5,5-trimethyl-4,5,6,7-tetrahydro-benzo[c]thiophen-1-yl)-propan-1-one (160 mg, 0.40 mmol) in DCM (10 mL) and DIPEA (0.11 mL, 0.64 mmol) is added methane sulfonylchloride (0.04 mL, 0.48 mmol) at 0° C. The reaction mixture is stirred at 0° C. for 30 min. The reaction mixture is diluted with DCM, washed with 0.1 N aq. NaOH followed by 10% aq. citric acid solution, dried over MgSO$_4$ and evaporated to give methanesulfonic acid 2-{2-chloro-6-methoxy-4-[3-oxo-3-(3,5,5-trimethyl-4,5,6,7-tetrahydro-benzo[c]thiophen-1-yl)-propyl]-phenoxy}-ethyl ester (183 mg) as a yellow oil; LC-MS: $t_R$=1.15 min, $[M+1]^+$=515.15.

b) A solution of methanesulfonic acid 2-{2-chloro-6-methoxy-4-[3-oxo-3-(3,5,5-trimethyl-4,5,6,7-tetrahydro-benzo[c]thiophen-1-yl)-propyl]-phenoxy}-ethyl ester in DMF is treated with the appropriate amine (≧4 eq.) and DIPEA (≧4 eq.). The reaction mixture is stirred at 75° C. for 7 h before it is purified by prep. HPLC (Waters Symmetry C18 19×50 mm 5 μm, 10 to 95% acetonitrile in water containing 0.5% formic acid) to give the desired product as a colourless lyophilisate or resin.

| Example | R | Scale (μmol) | LC-MS $t_R$ (min) | [M + H]$^+$ |
|---|---|---|---|---|
| 97 | NH$_2$ | 15 | 0.92 | 436.30 |
| 98 | NHCH$_3$ | 15 | 0.94 | 450.27 |
| 99 | NHCH$_2$CH$_3$ | 15 | 0.95 | 464.38 |
| 100 | NHCH(CH$_3$)$_2$ | 15 | 0.97 | 478.39 |
| 101 | HN-CH$_2$CH$_2$-OH | 15 | 0.92 | 480.35 |
| 102 | HN-CH(CH$_2$OH)$_2$ | 15 | 0.91 | 510.34 |
| 103 | HN-CH$_2$CH$_2$-NH$_2$ | 15 | 0.82 | 479.36 |
| 104 | 4-(2-hydroxyethyl)piperazin-1-yl | 15 | 0.86 | 549.45 |

| Example | R | Scale (μmol) | LC-MS $t_R$ (min) | [M + H]$^+$ |
|---|---|---|---|---|
| 105 | NH$_2$ | 15 | 0.94 | 450.19 |
| 106 | NHCH$_2$CH$_3$ | 15 | 0.97 | 478.42 |
| 107 | NHCH(CH$_3$)$_2$ | 15 | 0.98 | 492.43 |
| 108 | HN-CH$_2$CH$_2$-OH | 15 | 0.93 | 494.41 |
| 109 | HN-CH(CH$_2$OH)$_2$ | 15 | 0.92 | 524.48 |
| 110 | HN-CH$_2$CH$_2$-NH$_2$ | 15 | 0.83 | 493.46 |
| 111 | 4-(2-hydroxyethyl)piperazin-1-yl | 15 | 0.85 | 563.44 |

Examples 105 to 111

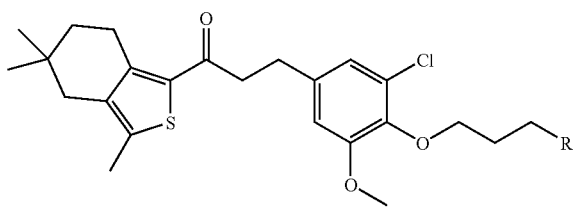

Examples 112 to 118

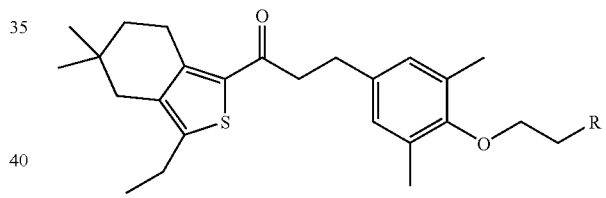

a) To a solution of 3-[3-chloro-4-(3-hydroxy-propoxy)-5-methoxy-phenyl]-1-(3,5,5-trimethyl-4,5,6,7-tetrahydro-benzo[c]thiophen-1-yl)-propan-1-one (170 mg, 0.38 mmol) in DCM (10 mL) and DIPEA (0.10 mL, 0.60 mmol) is added methane sulfonylchloride (0.04 mL, 0.45 mmol) at 0° C. The reaction mixture is stirred at 0° C. for 30 min. Another portion of methane sulfonylchloride (0.04 mL, 0.45 mmol) is added and stirring is continued for 20 min. The reaction mixture is diluted with DCM, washed with 0.1 N aq. NaOH followed by 10% aq. citric acid solution, dried over MgSO$_4$ and evaporated to give methanesulfonic acid 3-{2-chloro-6-methoxy-4-[3-oxo-3-(3,5,5-trimethyl-4,5,6,7-tetrahydro-benzo[c]thiophen-1-yl)-propyl]-phenoxy}-propyl ester (196 mg) as a yellow oil; LC-MS: $t_R$=1.17 min, [M+1]$^+$=529.17.

b) A solution of methanesulfonic acid 3-{2-chloro-6-methoxy-4-[3-oxo-3-(3,5,5-trimethyl-4,5,6,7-tetrahydro-benzo[c]thiophen-1-yl)-propyl]-phenoxy}-propyl ester in DMF is treated with the appropriate amine (≧4 eq.) and DIPEA (≧4 eq.). The reaction mixture is stirred at 75° C. for 7 h before it is purified by prep. HPLC (Waters Symmetry C18 19×50 mm 5 μm, 10 to 95% acetonitrile in water containing 0.5% formic acid) to give the desired product as a colourless lyophilisate or resin.

a) To a solution of 1-(3-ethyl-5,5-dimethyl-4,5,6,7-tetrahydro-benzo[c]thiophen-1-yl)-3-[4-(2-hydroxy-ethoxy)-3,5-dimethyl-phenyl]-propan-1-one (255 mg, 0.615 mmol) in THF (10 mL) and DIPEA (0.29 mL, 1.70 mmol) is added methane sulfonylchloride (0.09 mL, 1.15 mmol) at 0° C. The reaction mixture is stirred at 0° C. for 30 min. The reaction mixture is diluted with diethyl ether, washed with sat. aq. NaHCO$_3$ solution followed by 10% aq. citric acid solution, dried over Na$_2$SO$_4$ and evaporated to give methanesulfonic acid 2-{4-[3-(3-ethyl-5,5-dimethyl-4,5,6,7-tetrahydro-benzo[c]thiophen-1-yl)-3-oxo-propyl]-2,6-dimethyl-phenoxy}-ethyl ester (300 mg) as a brown resin; LC-MS: $t_R$=1.18 min, [M+1]$^+$=493.36.

b) A solution of methanesulfonic acid 2-{4-[3-(3-ethyl-5,5-dimethyl-4,5,6,7-tetrahydro-benzo[c]thiophen-1-yl)-3-oxo-propyl]-2,6-dimethyl-phenoxy}-ethyl ester in DMF is treated with the appropriate amine (≧4 eq.) and DIPEA (≧4 eq.). The reaction mixture is stirred at 75° C. for 7 h before it is purified by prep. HPLC (Waters Symmetry C18 19×50 mm 5 μm, 10 to 95% acetonitrile in water containing 0.5% formic acid) to give the desired product as a colourless lyophilisate or resin.

| Example | R | Scale (µmol) | LC-MS $t_R$ (min) | $[M + H]^+$ |
|---|---|---|---|---|
| 112 | NH₂ | 15 | 0.95 | 414.39 |
| 113 | NHCH₂CH₃ | 15 | 0.98 | 442.45 |
| 114 | NHCH(CH₃)₂ | 15 | 1.00 | 456.39 |
| 115 | HN–CH₂CH₂–OH | 15 | 0.94 | 458.40 |
| 116 | HN–CH(CH₂OH)–CH₂OH | 15 | 0.93 | 488.48 |
| 117 | HN–CH₂CH₂–NH₂ | 15 | 0.84 | 457.50 |
| 118 | piperazinyl-ethanol | 15 | 0.89 | 527.55 |

| Example | R | Scale (µmol) | LC-MS $t_R$ (min) | $[M + H]^+$ |
|---|---|---|---|---|
| 119 | NH₂ | 15 | 0.96 | 428.41 |
| 120 | NHCH₂CH₃ | 15 | 0.99 | 456.43 |
| 121 | NHCH(CH₃)₂ | 15 | 1.01 | 470.51 |
| 122 | HN–CH₂CH₂–OH | 15 | 0.95 | 472.47 |
| 123 | HN–CH(CH₂OH)–CH₂OH | 15 | 0.94 | 502.50 |
| 124 | HN–CH₂CH₂–NH₂ | 15 | 0.85 | 471.50 |
| 125 | piperazinyl-ethanol | 15 | 0.88 | 541.49 |

Examples 119-125

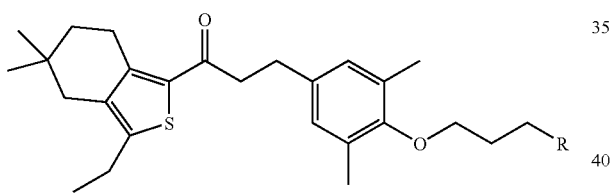

a) To a solution of 1-(3-ethyl-5,5-dimethyl-4,5,6,7-tetrahydro-benzo[c]thiophen-1-yl)-3-[4-(3-hydroxy-propoxy)-3,5-dimethyl-phenyl]-propan-1-one (246 mg, 0.575 mmol) in THF (10 mL) and DIPEA (0.26 mL, 1.5 mmol) is added methane sulfonylchloride (0.08 mL, 1.00 mmol) at 0° C. The reaction mixture is stirred at 0° C. for 30 min. The reaction mixture is diluted with diethyl ether, washed with sat. aq. NaHCO₃ solution followed by 10% aq. citric acid solution, dried over Na₂SO₄ and evaporated to give methanesulfonic acid 3-{4-[3-(3-ethyl-5,5-dimethyl-4,5,6,7-tetrahydro-benzo[c]thiophen-1-yl)-3-oxo-propyl]-2,6-dimethyl-phenoxy}-propyl ester (290 mg) as a brown resin; LC-MS: $t_R$=1.20 min, $[M+1]^+$=507.39.

b) A solution of methanesulfonic acid 3-{4-[3-(3-ethyl-5,5-dimethyl-4,5,6,7-tetrahydro-benzo[c]thiophen-1-yl)-3-oxo-propyl]-2,6-dimethyl-phenoxy}-propyl ester in DMF is treated with the appropriate amine (≧4 eq.) and DIPEA (≧4 eq.). The reaction mixture is stirred at 75° C. for 7 h before it is purified by prep. HPLC (Waters Symmetry C18 19×50 mm 5 µm, 10 to 95% acetonitrile in water containing 0.5% formic acid) to give the desired product as a colourless lyophilisate or resin.

Example 126

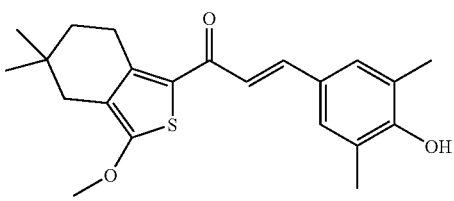

A solution of 1-(3-methoxy-5,5-dimethyl-4,5,6,7-tetrahydro-benzo[c]thiophen-1-yl)-ethanone (44 mg, 1.85 mmol) and 3,5-dimethyl-4-hydroxybenzaldehyde (30 mg, 0.20 mmol) in ethanol (1 mL) and 5 N HCl in isopropanol (0.5 mL) is stirred at rt for 2 h. The mixture is diluted with water (10 mL) and extracted with EA (30 mL). The organic extract is dried (Na₂SO₄), filtered and evaporated. The residue is dissolved in chloroform (5 mL) and a yellow precipitate forms. The suspension is diluted with diethyl ether (5 mL), the precipitate is filtered and washed with diethyl ether (2 mL) and dried to give 3-(4-hydroxy-3,5-dimethyl-phenyl)-1-(3-methoxy-5,5-dimethyl-4,5,6,7-tetrahydro-benzo[c]thiophen-1-yl)-propenone (25 mg) as a yellow powder; LC-MS: $t_R$=1.13 min, $[M+1]^+$=371.33; ¹H NMR (CDCl₃): δ 7.64 (d, J=15.2 Hz, 1H), 7.09 (d, J=15.2 Hz, 1H), 4.90 (s br, 1H), 4.02 (s, 3H), 3.15 (t, J=6.4 Hz, 2H), 2.31 (s, 2H), 2.28 (s, 6H), 1.57 (t, J=6.4 Hz, 2H), 0.99 (s, 6H).

Example 127

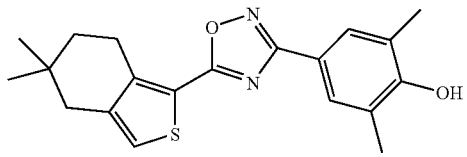

a) A solution of 5,5-dimethyl-4,5,6,7-tetrahydro-benzo[c]thiophene-1-carboxylic acid (0.79 g, 3.75 mmol) and TBTU (1.32 g, 4.13 mmol) and DIPEA (2.1 mL, 12.4 mmol) in DMF (6 mL) is stirred at rt for 10 min before 4,N-dihydroxy-3,5-dimethyl-benzamidine (676 mg, 3.75 mmol) is added. Stirring is continued at rt for 2 h. The reaction mixture is diluted with 1 N aq. HCl (250 mL) and extracted twice with EA. The organic extracts are dried over $Na_2SO_4$, filtered and the solvent is removed in vacuo to give 5,5-dimethyl-4,5,6,7-tetrahydro-benzo[c]thiophene-1-carboxylic acid N-(3,5-dimethyl-4-hydroxy-N-hydroxybenzamidine) ester (1.36 g) as a beige solid; LC-MS: $t_R$=1.03 min, $[M+1]^+$=373.17.

b) A solution of 5,5-dimethyl-4,5,6,7-tetrahydro-benzo[c]thiophene-1-carboxylic acid N-(3,5-dimethyl-4-hydroxy-N-hydroxybenzamidine) ester (1.35 g, 2.68 mmol) in toluene is heated to 95° C. for 2 days. The solvent is evaporated and the residue is purified by prep. HPLC (GROM-SIL ODS-4 HE, 75×30 mm ID, 10 µm, 70-100% acetonitrile in water containing 0.5% formic acid) to afford 4-[5-(5,5-dimethyl-4,5,6,7-tetrahydro-benzo[c]thiophen-1-yl)-[1,2,4]oxadiazol-3-yl]-2,6-di methyl-phenol (470 mg) as a beige solid; LC-MS: $t_R$=1.18 min, $[M+1]^+$=355.37; $^1$H NMR ($D_6$-DMSO): δ 8.95 (s br, 1H), 7.62 (s, 2H), 7.59 (s, 1H), 3.07 (t, J=7.0 Hz, 2H), 2.23 (s, 6H), 1.61 (t, J=7.0 Hz, 2H), 0.95 (s, 6H), one signal(s) under solvent.

Example 128

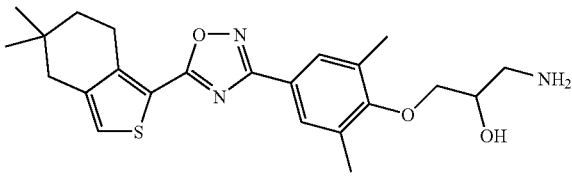

a) A solution of 4-[5-(5,5-dimethyl-4,5,6,7-tetrahydro-benzo[c]thiophen-1-yl)-[1,2,4]oxadiazol-3-yl]-2,6-dimethyl-phenol (35 mg, 1.18 mmol) in isopropanol (17 mL) is treated with 2 N aq. NaOH (8.6 mL) followed by epichlorohydrine (660 mg, 7.14 mmol). The mixture is stirred at 50° C. for 18 h before it is diluted with water and extracted twice with EA. The combined organic extracts are dried over $Na_2SO_4$, filtered, evaporated and dried to give 3-(3,5-dimethyl-4-oxiranylmethoxy-phenyl)-5-(5,5-dimethyl-4,5,6,7-tetrahydro-benzo[c]thiophen-1-yl)-[1,2,4]oxadiazole (480 mg) as a pale yellow oil; LC-MS: $t_R$=1.24 min, $[M+1]^+$=411.31.

b) A solution of 3-(3,5-dimethyl-4-oxiranylmethoxy-phenyl)-5-(5,5-dimethyl-4,5,6,7-tetrahydro-benzo[c]thiophen-1-yl)-[1,2,4]oxadiazole (500 mg, 1.18 mmol) in 2 N methanolic ammonia (7 mL) is heated in a sealed vial to 100° C. for 5 min in a microwave oven (300 W, active cooling during irradiation). The solvent is evaporated and the residue is purified by prep. HPLC (GROM-SIL ODS-4 HE, 75×30 mm ID, 10 µm, 20-95% acetonitrile in water containing 0.5% formic acid) to afford 1-amino-3-{4-[5-(5,5-dimethyl-4,5,6,7-tetrahydro-benzo[c]thiophen-1-yl)-[1,2,4]oxadiazol-3-yl]-2,6-dimethyl-phenoxy}-propan-2-ol (220 mg) as a colourless resin; LC-MS: $t_R$=0.92 min, $[M+1]^+$=428.38.

Examples 129 and 130

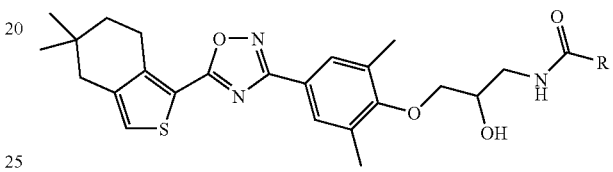

The appropriate carboxylic acid (25 µmol) is dissolved in a solution of TBTU (8 mg, 25 µmol) in DMF (0.5 mL). DIPEA (17 µL, 100 µmol) is added and the mixture is shaken for 10 min before 1-amino-3-{4-[5-(5,5-dimethyl-4,5,6,7-tetrahydro-benzo[c]thiophen-1-yl)-[1,2,4]oxadiazol-3-yl]-2,6-dimethyl-phenoxy}-propan-2-ol (9 mg, 20 µmol) is added. Shaking is continued at rt for 2 h. The mixture is separated by prep. HPLC (Waters XBridge Prep C18, 19×50 mm, 5 µm, 20-95% acetonitrile in water containing 0.35% HCl) to afford the desired amides as colourless lyophilisates.

|  |  |  | LC-MS | |
| --- | --- | --- | --- | --- |
| Example | R | Scale (µmol) | $t_R$ (min) | $[M + H]^+$ |
| 129 | ⤳⟍OH | 20 | 1.05 | 486.46 |
| 130 | ⤳⟍⟋OH | 20 | 1.03 | 500.45 |

Examples 131 to 134

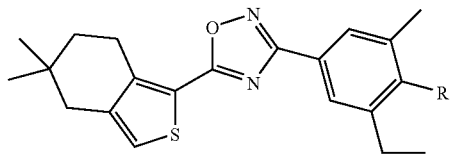

The following Examples are prepared in analogy to previous Examples using Example A and Hydroxyamidine 2:

| Example | R | prepared in analogy to Example | LC-MS $t_R$ (min) | $[M + H]^+$ |
|---|---|---|---|---|
| 131 | OH | 127 | 1.21 | 369.30 |
| 132 | ![structure] O-CH2-CH(OH)-CH2-NH2 | 128 | 0.92 | 442.32 |
| 133 | ![structure] O-CH2-CH(OH)-CH2-NH-C(=O)-CH2-OH | 129 | 1.07 | 500.54 |
| 134 | ![structure] O-CH2-CH(OH)-CH2-NH-C(=O)-CH2CH2-OH | 130 | 1.06 | 514.42 |

Examples 135 and 136

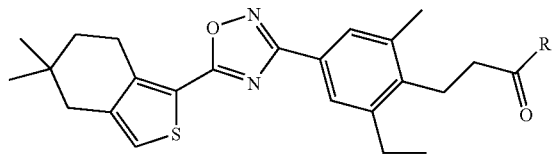

To a solution of 3-{4-[5-(5,5-dimethyl-4,5,6,7-tetrahydro-benzo[c]thiophen-1-yl)-[1,2,4]oxadiazol-3-yl]-2-ethyl-6-methyl-phenyl}-propionic acid (9 mg, 20 µmol) in DMF (0.5 mL), TBTU (7 mg, 22 µmol) and DIPEA (9 mg, 66 µmol) is added. The mixture is stirred at rt for 5 min before the appropriate amine (100 µmol) is added. Stirring is continued at rt for 1 h. The mixture is treated with formic acid (25 µL), diluted with acetonitrile (0.5 mL) and separated by prep. HPLC (Waters Symmetry C18 19×50 mm 5 µm, 20-100% acetonitrile in water containing 0.5% formic acid) to afford the desired amide as a colourless resin.

| Example | R | LC-MS $t_R$ (min) | $[M + H]^+$ |
|---|---|---|---|
| 135 | HN-CH2CH2-OH | 1.11 | 468.38 |
| 136 | HN-CH(CH2OH)-CH2-OH | 1.05 | 498.44 |

Examples 137 to 138

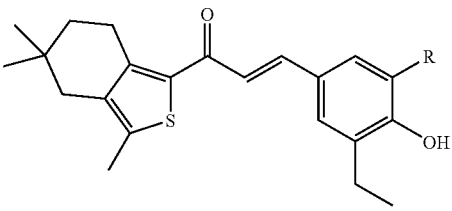

The following Examples are prepared in analogy to Example 22 starting from Example C and Aldehyde 1 or Aldehyde 2, respectively:

| Example | R | LC-MS $t_R$ (min) | $[M + H]^+$ |
|---|---|---|---|
| 137 | methyl | 1.17 | 369.11 |
| 138 | ethyl | 1.19 | 383.14 |

Example 137

$^1$H NMR (CDCl$_3$): δ 7.68 (d, J=15.8 Hz, 1H), 7.27 (s, 2H), 7.14 (d, J=15.2 Hz, 1H), 4.92 (s, 1H), 3.15 (t, J=7.0 Hz, 2H), 2.66 (q, J=7.6 Hz, 2H), 2.38 (s, 3H), 2.32 (s, 2H), 2.29 (s, 3H), 1.56 (t, J=7.0 Hz, 2H), 1.27 (t, J=7.6 Hz, 3H), 1.00 (s, 6H).

Example 139

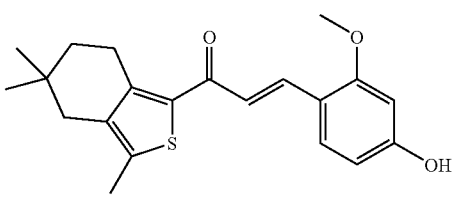

To a solution of 1-(3,5,5-trimethyl-4,5,6,7-tetrahydro-benzo[c]thiophen-1-yl)-ethanone (832 mg, 3.74 mmol, Example C) and 4-hydroxy-2-methoxybenzaldehyde (683 mg, 4.49 mmol) in methanol (25 mL), NaOH (6.0 g, 150 mmol) is added. The mixture is heated to 65° C. and stirred for 16 h. The dark olive-brown suspension is cooled to rt, diluted with EA (250 mL) and washed twice with sat. aq. NaHCO$_3$ solution. The organic extracts are dried over MgSO$_4$, filtered and the solvent is evaporated. The crude product is purified by CC on silica gel eluting with heptane:EA 3:2 to give 3-(4-hydroxy-2-methoxy-phenyl)-1-(3,5,5-trimethyl-4,5,6,7-tetrahydro-benzo[c]thiophen-1-yl)-propenone (794 mg) as a bright yellow solid; LC-MS: $t_R$=1.09 min, [M+1]$^+$=357.19.

Examples 140 to 142

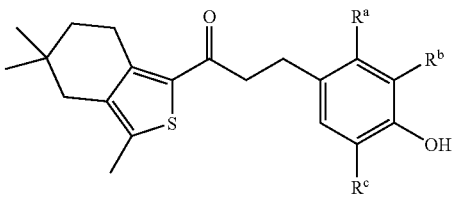

The following Examples are prepared in analogy to Example 23:

| Example | R$^a$ | R$^b$ | R$^c$ | prepared from Example | LC-MS $t_R$ (min) | [M + H]$^+$ |
|---------|-------|-------|-------|----------------------|-------------------|-------------|
| 140 | H | methyl | ethyl | 137 | 1.16 | 371.27 |
| 141 | H | ethyl | ethyl | 138 | 1.18 | 385.33 |
| 142 | OCH$_3$ | H | H | 139 | 1.09 | 359.23 |

Examples 143 to 145

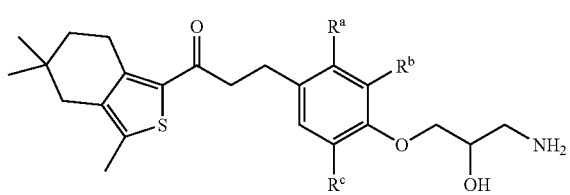

The following Examples are prepared in analogy to Example 33:

| Example | R$^a$ | R$^b$ | R$^c$ | prepared from Example | LC-MS $t_R$ (min) | [M + H]$^+$ |
|---------|-------|-------|-------|----------------------|-------------------|-------------|
| 143 | H | methyl | ethyl | 140 | 0.91 | 444.38 |
| 144 | H | ethyl | ethyl | 141 | 0.92 | 458.38 |
| 145 | OCH$_3$ | H | H | 142 | 0.88 | 432.31 |

Examples 146 to 150

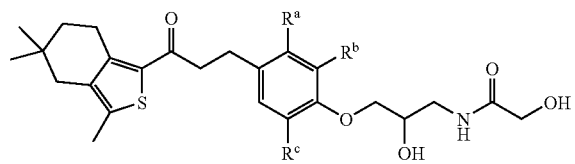

To a solution of glycolic acid (1.5 eq.) in DCM (10 mL), TBTU (1.3 eq.) and DIPEA (4.0 eq.) is added. The mixture is stirred at rt for 10 min before the appropriate 3-[4-(3-amino-2-hydroxy-propoxy)-phenyl]-1-(3,5,5-trimethyl-4,5,6,7-tetrahydro-benzo[c]thiophen-1-yl)-propan-1-one (0.5-1.0 mmol, 1. eq.) is added. Stirring is continued at rt for 1 h before another portion of glycolic acid (0.7 eq.) and TBTU (0.6 eq.) is added. The mixture is stirred for another hour, is diluted with DCM and washed with sat. aq. NaHCO$_3$ solution. The wash solutions are extracted back with DCM. The combined organic extracts are dried over MgSO$_4$, filtered and the solvent is evaporated. The crude product is purified by chromatography on prep. TLC plates using DCM containing 5% of methanol to give the desired 2-hydroxy-N-(2-hydroxy-3-{4-[3-oxo-3-(3,5,5-trimethyl-4,5,6,7-tetrahydro-benzo[c]thiophen-1-yl)-propyl]-phenoxy}-propyl)-acetamide as an almost colourless foam.

| Example | R$^a$ | R$^b$ | R$^c$ | prepared from Example | LC-MS $t_R$ (min) | [M + H]$^+$ |
|---------|-------|-------|-------|----------------------|-------------------|-------------|
| 146 | H | methyl | methyl | 33 | 1.00 | 488.17 |
| 147 | H | methyl | ethyl | 143 | 1.03 | 502.19 |
| 148 | H | ethyl | ethyl | 144 | 1.05 | 516.21 |
| 149 | H | Cl | OCH$_3$ | 54 | 1.00 | 524.11 |
| 150 | OCH$_3$ | H | H | 145 | 0.97 | 490.14 |

Example 148

$^1$H NMR (CDCl$_3$): δ 6.91 (s, 2H), 4.19 8 s, 2H), 4.18-4.10 (m, 1H), 3.84-3.70 (m, 3H), 3.51-3.40 (m, 1H), 3.09-2.91 (m, 6H), 2.62 (q, J=7.6 Hz, 4H), 2.38 (s, 3H), 2.28 (s, 2H), 1.53 (t, J=6.4 Hz, 2H), 1.21 (t, J=7.6 Hz, 6H), 0.96 (s, 6H).

Examples 151 and 152

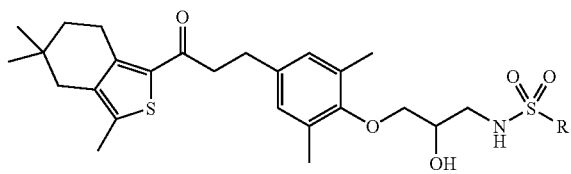

To a solution of 3-(3,5-dimethyl-4-oxiranylmethoxy-phenyl)-1-(3,5,5-trimethyl-4,5,6,7-tetrahydro-benzo[c]thiophen-1-yl)-propan-1-one (0.2-0.5 mmol, 1 eq.) in DMSO (2 mL) the appropriate alkanesulfonamide potassium salt (3.0 eq.) is added. The mixture is stirred at 50° C. for 20 h before it is diluted with EA (75 mL) and washed with 10% aq. citric acid solution followed by water. The organic extract is dried over MgSO$_4$, filtered and the solvent is evaporated. The crude product is chromatographed on prep. TLC plates with DCM containing 10% of methanol to afford the desired N-(3-{2,6-dimethyl-4-[3-oxo-3-(3,5,5-trimethyl-4,5,6,7-tetrahydro-benzo[c]thiophen-1-yl)-propyl]-phenoxy}-2-hydroxy-propyl)-alkanesulfonamide as a beige foam.

|         |        | LC-MS        |           |
|---------|--------|--------------|-----------|
| Example | R      | $t_R$ (min)  | [M + H]$^+$ |
| 151     | methyl | 1.06         | 508.27    |
| 152     | ethyl  | 1.09         | 522.30    |

Example 151

$^1$H NMR(CDCl$_3$): δ 6.88 (s, 2H), 4.83 (t br, J=6 Hz, 1H), 4.22-4.13 (m, 1H), 3.85-3.75 (m, 2H), 3.50-3.42 (m, 1H), 3.36-3.27 (, 1H), 3.06-3.00 (m, 6H), 2.95-2.88 (m, 2H), 2.79 (d br, J=4 Hz, 1H), 2.38 (s, 3H), 2.28 (s, 2H), 2.24 (s, 6H), 1.53 (t, J=6.4 Hz, 2H), 0.97 (s, 6H).

Examples 153 and 154

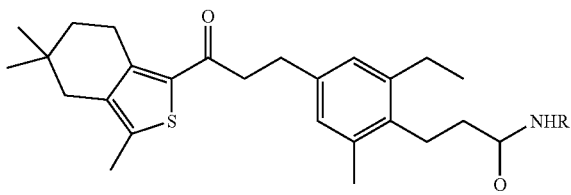

To a solution of 3-{2-ethyl-6-methyl-4-[3-oxo-3-(3,5,5-trimethyl-4,5,6,7-tetrahydro-benzo[c]thiophen-1-yl)-propyl]-phenyl}-propionic acid (8.5 mg, 20 μmol) in DMF (0.5 mL), TBTU (7 mg, 22 μmol) and DIPEA (9 mg, 66 μmol) is added. The mixture is stirred at rt for 5 min before the appropriate amine (100 μmol) is added. Stirring is continued at rt for 1 h. The mixture is treated with formic acid (25 μL), diluted with acetonitrile (0.5 mL) and separated by prep. HPLC (Waters Symmetry C18 19×50 mm 5 μm, 20-100% acetonitrile in water containing 0.5% formic acid) to afford the desired amide as a colourless resin.

|         |          | LC-MS        |           |
|---------|----------|--------------|-----------|
| Example | R        | $t_R$ (min)  | [M + H]$^+$ |
| 153     | HN⁀⁀OH   | 1.09         | 470.30    |
| 154     | HN⁀(OH)⁀OH | 1.03       | 499.92    |

Examples 155 to 179

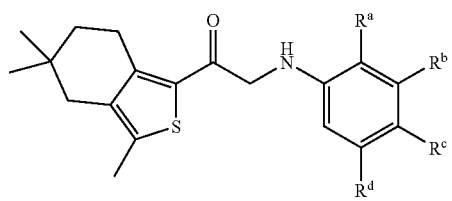

To the appropriate anilines (50 μmol, 2 eq.) and K$_2$CO$_3$ (10.5 mg, 75 μmol) a solution of 2-bromo-1-(3,5,5-trimethyl-4,5,6,7-tetrahydro-benzo[c]thiophen-1-yl)-ethanone (7.5 mg, 25 μmol) in acetone (0.7 mL) is added. The suspension is stirred at rt for 18 h before it is filtered. The solvent of the filtrate is evaporated and the crude product is purified by prep. HPLC (Symmetry C18 5 μm, 19×50 mm, 20-95% acetonitrile in water containing 0.5% formic acid) to give the desired 2-phenylamino-1-(3,5,5-trimethyl-4,5,6,7-tetrahydro-benzo[c]thiophen-1-yl)-ethanone.

|  |  |  |  |  | LC-MS | |
|---|---|---|---|---|---|---|
| Example | $R^a$ | $R^b$ | $R^c$ | $R^d$ | $t_R$ (min) | $[M + H]^+$ |
| 155 | H | H | H | H | 1.13 | 314.38 |
| 156 | CH₃ | H | H | H | 1.17 | 328.30 |
| 157 | CH₂CH₃ | H | H | H | 1.20 | 342.39 |
| 158 | H | CH₃ | H | CH₃ | 1.16 | 342.33 |
| 159 | H | CF₃ | H | H | 1.19 | 382.32 |
| 160 | OCH₃ | H | H | H | 1.16 | 344.32 |
| 161 | H | H | OCH₃ | H | 1.02 | 344.31 |
| 162 | CH₃ | H | OCH₃ | H | 1.11 | 358.35 |
| 163 | OCH₃ | H | OCH₃ | H | 1.07 | 374.25 |
| 164 | OCH₃ | H | H | CF₃ | 1.21 | 412.12 |
| 165 | H | H | OCH₃ | CF₃ | 1.17 | 412.29 |
| 166 | H | H | ⌇⌇O~~~OH | H | 1.02 | 358.34 |
| 167 | H | H | ⌇⌇O~~~OH | H | 0.93 | 374.35 |
| 168 | H | H | O~~~OH | H | 0.95 | 388.31 |
| 169 | H | H | O-CH(CH₃)-OH | H | 0.96 | 388.34 |
| 170 | H | H | O-CH₂-CH(OH)-CH₂OH | H | 0.87 | 404.28 |
| 171 | H | H | O-CH₂CH₂-N(CH₃)₂ | H | 0.71 | 401.32 |
| 172 | H | H | O-CH₂CH₂-morpholine | H | 0.86 | 443.36 |
| 173 | CH₃ | H | O~~~OH | H | 1.02 | 388.30 |
| 174 | CH₃ | H | O~~~OH | H | 1.04 | 402.24 |
| 175 | CH₃ | H | O-CH(CH₃)-OH | H | 1.05 | 402.23 |
| 176 | CH₃ | H | O-CH₂-CH(OH)-CH₂OH | H | 0.95 | 418.23 |
| 177 | CH₃ | H | O-CH₂-CH(OH)-CH₂OH | H | 0.95 | 418.26 |
| 178 | CH₃ | H | O-CH₂CH₂-N(CH₃)₂ | H | 0.72 | 415.40 |
| 179 | CH₃ | H | O-CH₂CH₂-morpholine | H | 0.90 | 457.42 |

Examples 180 to 185

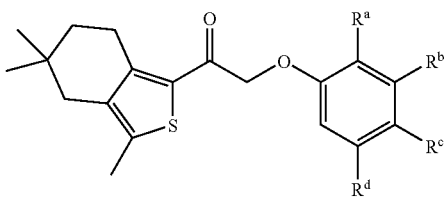

To the appropriate phenols (50 µmol, 2 eq.) and $K_2CO_3$ (10.5 mg, 75 µmol) a solution of 2-bromo-1-(3,5,5-trimethyl-4,5,6,7-tetrahydro-benzo[c]thiophen-1-yl)-ethanone (7.5 mg, 25 µmol) in acetone (0.7 mL) is added. The suspension is stirred at rt for 18 h before it is filtered. The solvent of the filtrate is evaporated and the crude product is purified by prep. HPLC (Symmetry C18 5 µm, 19×50 mm, 20-95% acetonitrile in water containing 0.5% formic acid) to give the desired 2-phenoxy-1-(3,5,5-trimethyl-4,5,6,7-tetrahydro-benzo[c]thiophen-1-yl)-ethanone.

| | | | | LC-MS | |
|---|---|---|---|---|---|
| Example | $R^a$ | $R^b$ | $R^c$ | $R^d$ | $t_R$ (min) | $[M + H]^+$ |
| 180 | H | H | H | H | 1.13 | 315.26 |
| 181 | H | $CH_3$ | H | $CH_3$ | 1.18 | 343.28 |
| 182 | $OCH_3$ | H | H | H | 1.12 | 345.26 |
| 183 | H | $CF_3$ | H | H | 1.18 | 383.30 |
| 184 | H | H | ⌒⌒OH | H | 1.05 | 359.32 |
| 185 | $OCH_3$ | H | —$CH_2OH$ | H | 1.02 | 375.34 |

Examples 186 to 188

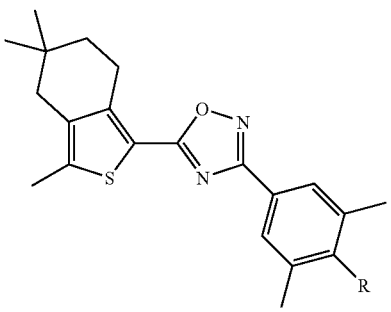

The following Examples are prepared in analogy to previous Examples using Example C and Hydroxyamidine 1:

| | | prepared in analogy to | LC-MS | |
|---|---|---|---|---|
| Example | R | Example | $t_R$ (min) | $[M + H]^+$ |
| 186 | OH | 127 | 1.21 | 369.26 |
| 187 | O–CH₂–CH(OH)–CH₂–NH₂ | 128 | 0.94 | 442.28 |
| 188 | O–CH₂–CH(OH)–CH₂–NH–C(O)–CH₂–OH | 129 | 1.08 | 500.45 |

Example 186

$^1$H NMR ($D_6$-DMSO): δ 8.91 (s, 1H), 7.60 (s, 2H), 3.04 (t, J=7.0 Hz, 2H), 2.36 (s, 3H), 2.34 (s, 2H), 2.23 (s, 6H), 1.57 (t, J=7.0 Hz, 2H), 0.96 (s, 6H).

Examples 189 to 192

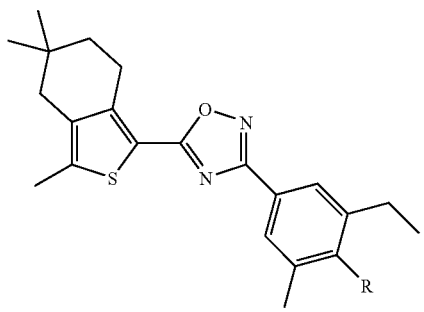

The following Examples are prepared in analogy to previous Examples using Example C and Hydroxyamidine 2:

| | | prepared in analogy to | LC-MS | |
|---|---|---|---|---|
| Example | R | Example | $t_R$ (min) | $[M + H]^+$ |
| 189 | OH | 127 | 1.23 | 383.27 |
| 190 | O–CH₂–CH(OH)–CH₂–NH₂ | 128 | 0.95 | 456.47 |

-continued

| Example | R | prepared in analogy to Example | LC-MS $t_R$ (min) | $[M + H]^+$ |
|---|---|---|---|---|
| 191 | (structure with O, NH, OH, HO) | 129 | 1.10 | 514.41 |
| 192 | (structure with O, NH, OH, HO) | 130 | 1.09 | 528.52 |

Examples 193 and 194

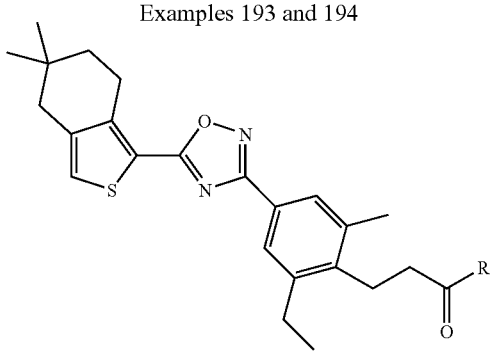

The following Examples are prepared in analogy to previous Examples using Intermediate 3:

| Example | R | prepared in analogy to Example | LC-MS $t_R$ (min) | $[M + H]^+$ |
|---|---|---|---|---|
| 193 | HN-CH2CH2-OH | 135 | 1.15 | 482.36 |
| 194 | HN-CH(CH2OH)-CH2OH | 136 | 1.09 | 512.31 |

Examples 195 to 199

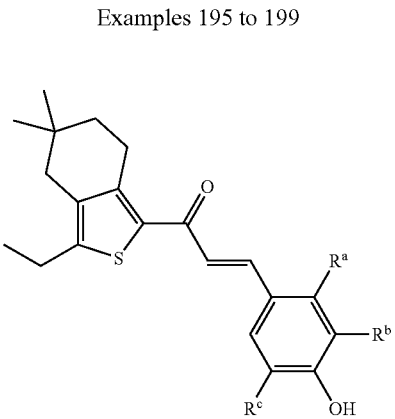

The following Examples are prepared in analogy to previous Examples using Example C and commercially available benzaldehydes or the described Aldehydes 1 and 2:

| Example | $R^a$ | $R^b$ | $R^c$ | prepared in analogy to Example | LC-MS $t_R$ (min) | $[M + H]^+$ |
|---|---|---|---|---|---|---|
| 195 | H | methyl | ethyl | 22 | 1.19 | 383.29 |
| 196 | H | ethyl | ethyl | 22 | 1.21 | 397.33 |
| 197 | H | methyl | Cl | 22 | 1.19 | 389.2 |
| 198 | H | OCH$_3$ | Cl | 22 | 1.16 | 405.04 |
| 199 | OCH$_3$ | H | H | 139 | 1.11 | 371.38 |

Example 198

$^1$H NMR (CDCl$_3$): δ 7.60 (d, J=15.2 Hz, 1H), 7.28 (d, J=1.8 Hz, 1H), 7.15 (d, J=15.2 Hz, 1H), 6.99 (d, J=1.8 Hz, 1H), 6.04 (s, 1H), 3.98 (s, 3H), 3.15 (t, J=6.4 Hz, 2H), 2.78 (q, J=7.6 Hz, 2H), 2.34 (s, 2H), 1.58 8t, J=6.4 Hz, 2H), 1.32 (t, J=7.6 Hz, 3H), 0.99 (s, 6H).

Example 200

3-[4-(3-Amino-2-hydroxy-propoxy)-3-chloro-5-methyl-phenyl]-1-(3-ethyl-5,5-dimethyl-4,5,6,7-tetrahydro-benzo[c]thiophen-1-yl)-propenone is prepared in analogy to Example 33 starting from Example 197; LC-MS: $t_R$=0.93 min, $[M+1]^+$=462.30.

Examples 201 to 205

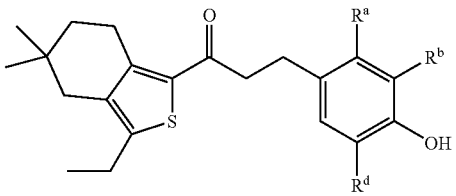

The following examples are prepared from previous examples in analogy to Example 23:

|         |          |       |       |         | prepared from | LC-MS      |            |
|---------|----------|-------|-------|---------|---------|------------|
| Example | $R^a$    | $R^b$ | $R^c$ | Example | $t_R$ (min) | $[M + H]^+$ |
| 201     | H        | methyl | ethyl | 195     | 1.17    | 385.31     |
| 202     | H        | ethyl  | ethyl | 196     | 1.19    | 399.34     |
| 203     | H        | methyl | Cl    | 197     | 1.16    | 391.23     |
| 204     | H        | OCH₃   | Cl    | 198     | 1.13    | 407.16     |
| 205     | OCH₃     | H      | H     | 199     | 1.10    | 373.09     |

Examples 206 to 210

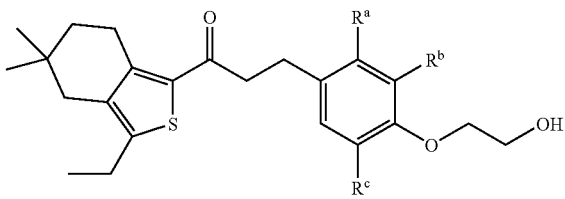

The following examples are prepared from previous examples in analogy to Example 66:

|         |          |       |       |         | prepared from | LC-MS      |            |
|---------|----------|-------|-------|---------|---------|------------|
| Example | $R^a$    | $R^b$ | $R^c$ | Example | $t_R$ (min) | $[M + H]^+$ |
| 206     | H        | methyl | ethyl | 201     | 1.16    | 429.38     |
| 207     | H        | ethyl  | ethyl | 202     | 1.18    | 443.36     |
| 208     | H        | methyl | Cl    | 203     | 1.15    | 435.03     |
| 209     | H        | OCH₃   | Cl    | 204     | 1.18    | 451.09     |
| 210     | OCH₃     | H      | H     | 205     | 1.12    | 417.12     |

Example 208

¹H NMR (CDCl₃): δ 7.09 (d, J=2.3 Hz, 1H), 6.95 (d, J=2.3 Hz, 1H), 4.05-4.00 (m, 2H), 3.97-3.90 (m, 2H), 3.09-3.00 (m, 4H), 2.97-2.90 (m, 2H), 2.72 (q, J=7.6 Hz, 2H), 2.30 (s, 2H), 2.29 (s, 3H), 1.54 (t, J=6.4 Hz, 2H), 1.27 (t, J=7.6 Hz, 3H), 0.97 (s, 6H).

Examples 211 to 214

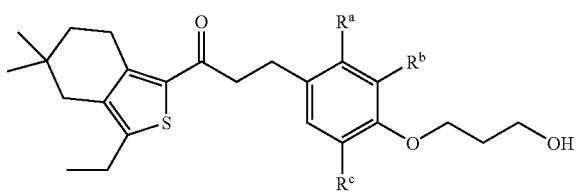

The following examples are prepared from previous examples in analogy to Example 68:

|         |          |       |       |         | prepared from | LC-MS      |            |
|---------|----------|-------|-------|---------|---------|------------|
| Example | $R^a$    | $R^b$ | $R^c$ | Example | $t_R$ (min) | $[M + H]^+$ |
| 211     | H        | methyl | ethyl | 201     | 1.17    | 443.21     |
| 212     | H        | ethyl  | ethyl | 202     | 1.19    | 457.39     |
| 213     | H        | OCH₃   | Cl    | 204     | 1.14    | 465.32     |
| 214     | OCH₃     | H      | H     | 205     | 1.13    | 431.35     |

Examples 215 to 217

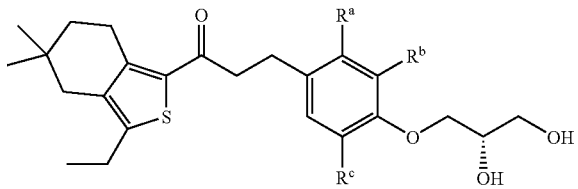

The following examples are prepared from previous examples in analogy to Example 68:

|         |          |       |       |         | prepared from | LC-MS      |            |
|---------|----------|-------|-------|---------|---------|------------|
| Example | $R^a$    | $R^b$ | $R^c$ | Example | $t_R$ (min) | $[M + H]^+$ |
| 215     | H        | methyl | ethyl | 201     | 1.09    | 459.37     |
| 216     | H        | ethyl  | ethyl | 202     | 1.12    | 473.39     |
| 217     | OCH₃     | H      | H     | 205     | 1.04    | 447.32     |

Examples 218 to 223

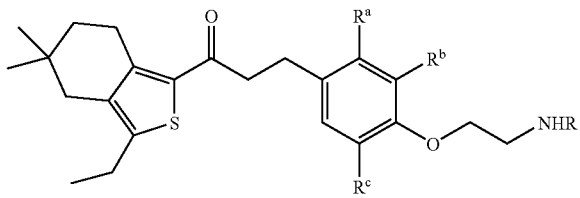

The following examples are prepared in analogy to Example 112 using previous examples:

| Example | $R^a$ | $R^b$ | $R^c$ | R | prepared from Example | $t_R$ (min) | $[M + H]^+$ |
|---|---|---|---|---|---|---|---|
| 218 | H | $CH_3$ | $CH_2CH_3$ | H | 201 | 0.94 | 428.15 |
| 219 | H | $CH_2CH_3$ | $CH_2CH_3$ | H | 202 | 0.97 | 442.35 |
| 220 | H | $CH_3$ | Cl | H | 203 | 0.93 | 434.21 |
| 221 | H | $OCH_3$ | Cl | H | 204 | 0.92 | 450.13 |
| 222 | $OCH_3$ | H | H | H | 205 | 0.89 | 416.33 |
| 223 | H | $CH_3$ | $CH_3$ | $CH_3$ | 65 | 0.94 | 428.30 |

Example 220

$^1$H NMR (CDCl$_3$): δ 7.03 (d, J=1.8 Hz, 1H), 6.952 (d, J=1.8 Hz, 1H), 3.92 (t, J=4.7 Hz, 2H), 3.11-3.00 (m, 6H), 2.96-2.89 (m, 2H), 2.73 (q, J=7.6 Hz, 2H), 2.30 (s, 2H), 2.28 (s, 3H), 1.54 8t, J=6.4 Hz, 2H), 1.27 (t, J=7.6 Hz, 3H), 0.97 8 s, 6H).

Examples 224 to 230

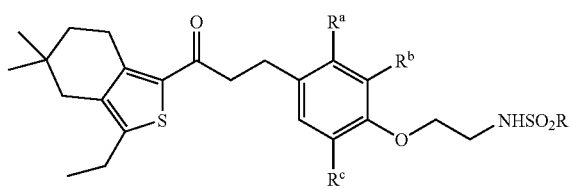

A solution of the substituted 3-[4-(2-amino-ethoxy)-phenyl]-1-(3-ethyl-5,5-dimethyl-4,5,6,7-tetrahydro-benzo[c]thiophen-1-yl)-propan-1-one (50-200 µmol, 1 eq.) in DCM (2 mL) is treated with DIPEA (1.6 eq.) followed by the appropriate alkane sulfonylchloride (1.2 eq.). The reaction mixture is stirred at rt for 4 h, diluted with DCM and washed with brine followed by water. The organic extract is dried over MgSO$_4$, filtered and the solvent of the filtrate is evaporated. The crude product is chromatographed on prep. TLC plates with either DCM containing 5-10% of methanol or heptane:EA 1:1 to furnish the desired N-(2-{4-[3-(3-ethyl-5,5-dimethyl-4,5,6,7-tetrahydro-benzo[c]thiophen-1-yl)-3-oxo-propyl]-phenoxy}-ethyl)-alkane-sulfonamide as an almost colourless to pale yellow resin.

| Example | $R^a$ | $R^b$ | $R^c$ | R | prepared from Example | $t_R$ (min) | $[M + H]^+$ |
|---|---|---|---|---|---|---|---|
| 224 | H | $CH_3$ | $CH_3$ | $CH_3$ | 112 | 1.15 | 492.15 |
| 225 | H | $CH_3$ | $CH_2CH_3$ | $CH_3$ | 218 | 1.16 | 506.37 |
| 226 | H | $CH_3$ | $CH_2CH_3$ | $CH_2CH_3$ | 218 | 1.18 | 520.39 |
| 227 | H | $CH_2CH_3$ | $CH_2CH_3$ | $CH_3$ | 219 | 1.17 | 520.35 |
| 228 | H | $CH_3$ | Cl | $CH_3$ | 220 | 1.16 | 512.33 |
| 229 | H | $OCH_3$ | Cl | $CH_3$ | 221 | 1.14 | 528.18 |
| 230 | $OCH_3$ | H | H | $CH_3$ | 222 | 1.12 | 494.38 |

Example 225

$^1$H NMR (CDCl$_3$): δ 6.92-6.88 (m, 2H), 4.91 (t br, J=6 Hz, 1H), 3.88 (t, J=5.2 Hz, 2H), 3.52 (q, J=5.3 Hz, 2H), 3.09-3.02 (m, 6H), 2.98-2.90 (m, 2H), 2.72 (q, J=7.6 Hz, 2H), 2.61 (q, J=7.6 Hz, 2H), 2.30 (s, 2H), 2.25 (s, 3H), 1.54 (t, J=7.6 Hz, 3H), 1.22 (t, J=7.6 Hz, 3H), 0.96 (s, 6H).

Examples 231 to 237

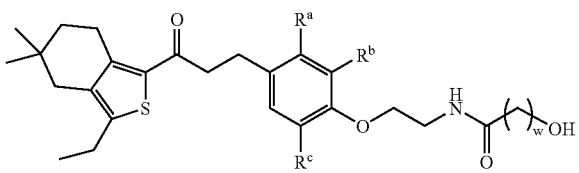

To a solution of the appropriately substituted 3-[4-(2-amino-ethoxy)-phenyl]-1-(3-ethyl-5,5-dimethyl-4,5,6,7-tetrahydro-benzo[c]thiophen-1-yl)-propan-1-one (0.1-2 mmol, 1 eq.) in DCM (2-20 mL), DIPEA (4 eq.) and TBTU (1.4 eq.) followed by either glycolic acid or 3-hydroxy-propionic acid (1.5 eq.) is added. The mixture is stirred at rt for 1-3 h before it is diluted with DCM, washed with sat. aq. NaHCO$_3$, dried over MgSO$_4$, and filtered. The solvent of the filtrate is evaporated and the crude product is purified either by chromatography on prep. TLC-plates or by CC on silica gel eluting with DCM containing 5-10% of methanol to give the desired N-(2-{4-[3-(3-ethyl-5,5-dimethyl-4,5,6,7-tetrahydro-benzo[c]thiophen-1-yl)-3-oxo-propyl]-phenoxy}-ethyl)-hydroxy-alkylamide as an almost colourless to pale yellow resin.

| Example | $R^a$ | $R^b$ | $R^c$ | w | prepared from Example | LC-MS $t_R$ (min) | $[M + H]^+$ |
|---|---|---|---|---|---|---|---|
| 231 | H | CH₃ | CH₃ | 1 | 112 | 1.10 | 472.48 |
| 232 | H | CH₃ | CH₃ | 2 | 112 | 1.09 | 486.41 |
| 233 | H | CH₃ | CH₂CH₃ | 1 | 218 | 1.11 | 486.40 |
| 234 | H | CH₂CH₃ | CH₂CH₃ | 1 | 219 | 1.14 | 500.38 |
| 235 | H | CH₃ | Cl | 1 | 220 | 1.12 | 492.38 |
| 236 | H | OCH₃ | Cl | 1 | 221 | 1.10 | 508.15 |
| 237 | OCH₃ | H | H | 1 | 222 | 1.07 | 474.37 |

Example 231

¹H NMR (CDCl₃): δ 7.01 (t br, J=5 Hz, 1H), 6.88 (s, 2H), 4.16 (d, J=3.5 Hz, 2H), 3.86 (t, J=4.7 Hz, 2H), 3.71 (q, J=5.3 Hz, 2H), 3.09-3.00 (m, 4H), 2.95-2.88 (m, 2H), 2.73 (q, J=7.6 Hz, 2H), 2.67 (t br, J=4 Hz, 1H), 2.30 (s, 2H), 2.24 (s, 6H), 1.55 (t, J=6.4 Hz, 2H), 1.27 (t, J=7.6 Hz, 3H), 0.97 (s, 6H).

Examples 238 to 250

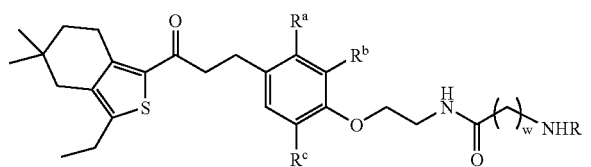

To a solution of the appropriate BOC-protected amino acid (1.5 eq.) in DCM (2-20 mL), TBTU (1.4 eq.) and DIPEA (4 eq.) is added. The mixture is stirred at rt for 10 min before a solution of the appropriately substituted 3-[4-(2-amino-ethoxy)-phenyl]-1-(3-ethyl-5,5-dimethyl-4,5,6,7-tetrahydro-benzo[c]thiophen-1-yl)-propan-1-one (0.1-2 mmol, 1 eq.) in DCM (2-5 mL) is added. The mixture is stirred at rt for 1-3 h before it is diluted with DCM, washed with sat. aq. NaHCO₃, dried over MgSO₄, and filtered. The solvent of the filtrate is evaporated and the residue is dissolved in 4 N HCl in dioxane. The mixture is stirred at rt for 45 to 90 min before it s diluted with DCM, washed with sat. aq. NaHCO₃, dried over MgSO₄ and filtered. The solvent of the filtrate is evaporated and the crude product is purified by chromatography on prep. TLC-plates using DCM containing 5-10% of 7 N NH₃ in methanol to give the desired amino-N-(2-{4-[3-(3-ethyl-5,5-dimethyl-4,5,6,7-tetrahydro-benzo[c]thiophen-1-yl)-3-oxo-propyl]-phenoxy}-ethyl)-alkylamide as a pale yellow resin.

| Example | $R^a$ | $R^b$ | $R^c$ | R | w | prepared from Example | LC-MS $t_R$ (min) | $[M + H]^+$ |
|---|---|---|---|---|---|---|---|---|
| 238 | H | CH₃ | CH₃ | H | 1 | 112 | 0.92 | 471.37 |
| 239 | H | CH₃ | CH₃ | H | 2 | 112 | 0.92 | 485.42 |
| 240 | H | CH₃ | CH₃ | CH₃ | 1 | 112 | 0.93 | 485.40 |
| 241 | H | CH₃ | CH₃ | CH₃ | 2 | 112 | 0.93 | 499.45 |
| 242 | H | CH₃ | CH₂CH₃ | H | 1 | 218 | 0.92 | 485.21 |
| 243 | H | CH₃ | CH₂CH₃ | CH₃ | 1 | 218 | 0.95 | 499.44 |
| 244 | H | CH₃ | CH₂CH₃ | CH₃ | 2 | 218 | 0.95 | 513.47 |
| 245 | H | CH₂CH₃ | CH₂CH₃ | CH₃ | 1 | 219 | 0.96 | 513.44 |
| 246 | H | OCH₃ | Cl | H | 1 | 221 | 0.91 | 507.27 |
| 247 | H | OCH₃ | Cl | CH₃ | 1 | 221 | 0.92 | 521.18 |
| 248 | H | OCH₃ | Cl | CH₃ | 2 | 221 | 0.93 | 535.19 |
| 249 | OCH₃ | H | H | | 1 | 1 | 222 | 0.91 | 487.19 |
| 250 | OCH₃ | H | H | | 2 | 1 | 222 | 0.91 | 501.22 |

Example 243

$^1$H NMR (CDCl$_3$): δ 7.78 (s br, 1H), 6.90 (s, 1H), 6.88 (s, 1H), 3.83 (t, J=5.0 Hz, 2H), 3.69 (q, J=5.2 Hz, 2H), 3.30 (s, 2H), 3.10-3.00 (m, 4H), 2.98-2.90 (m, 2H), 2.72 (q, J=7.6 Hz, 2H), 2.61 (q, J=7.6 Hz, 2H), 2.47 (s, 3H), 2.30 (s, 2H), 2.25 (s, 3H), 1.54 8t, J=6.4 Hz, 2H), 1.25 (t, J=7.6 Hz, 3H), 1.23 (t, J=7.6 Hz, 3H), 0.97 (s, 6H).

Examples 251 to 270

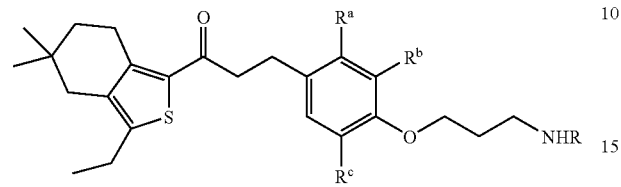

The following examples are prepared in analogy to previous examples starting from Example 119.

| Ex. | R$^a$ | R$^b$ | R$^c$ | R | prepared in analogy to Example | LC-MS t$_R$(min) | [M + H]$^+$ |
|---|---|---|---|---|---|---|---|
| 251 | H | CH$_3$ | CH$_3$ | CH$_3$ | 223 | 0.96 | 442.32 |
| 252 | H | CH$_3$ | CH$_3$ | SO$_2$CH$_3$ | 224 | 1.15 | 506.07 |
| 253 | H | CH$_3$ | CH$_3$ | SO$_2$CH$_2$CH$_3$ | 224 | 1.18 | 520.42 |
| 254 | H | CH$_3$ | CH$_3$ | COCH$_2$OH | 231 | 1.12 | 486.46 |
| 255 | H | CH$_3$ | CH$_3$ | COCH$_2$NHCH$_3$ | 238 | 0.94 | 499.26 |
| 256 | H | CH$_3$ | CH$_2$CH$_3$ | H | 119 | 0.96 | 442.42 |
| 257 | H | CH$_3$ | CH$_2$CH$_3$ | COCH$_2$OH | 231 | 1.13 | 500.25 |
| 258 | H | CH$_3$ | CH$_2$CH$_3$ | COCH$_2$NHCH$_3$ | 238 | 0.95 | 513.42 |
| 259 | H | CH$_3$ | CH$_2$CH$_3$ | COCH$_2$CH$_2$NHCH$_3$ | 238 | 0.96 | 527.30 |
| 260 | H | CH$_2$CH$_3$ | CH$_2$CH$_3$ | H | 119 | 0.97 | 456.37 |
| 261 | H | CH$_2$CH$_3$ | CH$_2$CH$_3$ | COCH$_2$OH | 231 | 1.15 | 514.46 |
| 262 | H | CH$_2$CH$_3$ | CH$_2$CH$_3$ | COCH$_2$NHCH$_3$ | 238 | 0.97 | 527.44 |
| 263 | H | OCH$_3$ | Cl | H | 119 | 0.93 | 464.30 |
| 264 | H | OCH$_3$ | Cl | SO$_2$CH$_3$ | 224 | 1.15 | 542.25 |
| 265 | H | OCH$_3$ | Cl | COCH$_2$OH | 231 | 1.10 | 522.27 |
| 266 | H | OCH$_3$ | Cl | COCH$_2$NH$_2$ | 238 | 0.92 | 521.28 |
| 267 | H | OCH$_3$ | Cl | COCH$_2$NHCH$_3$ | 238 | 0.93 | 535.29 |
| 268 | OCH$_3$ | H | H | H | 119 | 0.92 | 430.35 |
| 269 | OCH$_3$ | H | H | SO$_2$CH$_3$ | 224 | 1.13 | 508.36 |
| 270 | OCH$_3$ | H | H | COCH$_2$OH | 231 | 1.09 | 488.43 |

Example 254

$^1$H NMR (CDCl$_3$): δ 6.88 (s, 2H), 4.10 (s, 2H), 3.84 (t, J=5.9 Hz, 2H), 3.61 (q, J=5.9 Hz, 2H), 3.08-3.00 (m, 4H), 2.95-2.88 (m, 2H), 2.72 (q, J=7.6 Hz, 2H), 2.42 (s br, 1H), 2.30 (s, 2H), 2.24 (s, 6H), 2.03 (p, J=6.4 Hz, 2H), 1.54 8t, J=6.4 Hz, 2H), 1.27 (t, J=7.6 Hz, 3H), 0.97 (s, 6H).

Examples 271 to 319

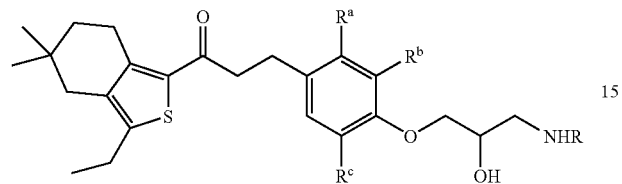

The following examples are prepared in analogy to previous examples starting from Example 65:

| Ex. | R$^a$ | R$^b$ | R$^c$ | R | prepared in analogy to Example | t$_R$(min) | [M + H]$^+$ |
|---|---|---|---|---|---|---|---|
| 271 | H | CH$_3$ | CH$_3$ | H | 33 | 0.92 | 444.30 |
| 272 | H | CH$_3$ | CH$_3$ | CH$_3$ | 34 | 0.95 | 458.10 |
| 273 | H | CH$_3$ | CH$_2$CH$_3$ | H | 33 | 0.94 | 458.42 |
| 274 | H | CH$_2$CH$_3$ | CH$_2$CH$_3$ | H | 33 | 0.95 | 472.46 |
| 275 | H | CH$_3$ | Cl | H | 33 | 0.92 | 464.06 |
| 276 | H | OCH$_3$ | Cl | H | 33 | 0.90 | 480.08 |
| 277 | OCH$_3$ | H | H | H | 33 | 0.89 | 446.32 |
| 278 | H | CH$_3$ | CH$_3$ | SO$_2$CH$_3$ | 151 | 1.10 | 522.42 |
| 279 | H | CH$_3$ | CH$_3$ | SO$_2$CH$_2$CH$_3$ | 151 | 1.11 | 536.11 |
| 280 | H | CH$_3$ | CH$_3$ | SO$_2$NHCH$_3$ | 151 | 1.09 | 537.10 |
| 281 | H | CH$_3$ | CH$_2$CH$_3$ | SO$_2$CH$_3$ | 151 | 1.11 | 536.14 |
| 282 | H | CH$_3$ | CH$_2$CH$_3$ | SO$_2$CH$_2$CH$_3$ | 151 | 1.13 | 550.29 |
| 283 | H | CH$_3$ | CH$_2$CH$_3$ | SO$_2$NHCH$_3$ | 151 | 1.10 | 551.33 |
| 284 | H | CH$_2$CH$_3$ | CH$_2$CH$_3$ | SO$_2$CH$_3$ | 151 | 1.14 | 550.41 |
| 285 | H | CH$_2$CH$_3$ | CH$_2$CH$_3$ | SO$_2$CH$_2$CH$_3$ | 151 | 1.10 | 542.00 |
| 286 | H | OCH$_3$ | Cl | SO$_2$CH$_3$ | 151 | 1.09 | 558.08 |
| 287 | H | OCH$_3$ | Cl | SO$_2$CH$_2$CH$_3$ | 151 | 1.11 | 572.18 |
| 288 | H | OCH$_3$ | Cl | SO$_2$NHCH$_3$ | 151 | 1.08 | 573.07 |
| 289 | OCH$_3$ | H | H | SO$_2$CH$_3$ | 151 | 1.06 | 524.33 |
| 290 | H | CH$_3$ | CH$_3$ | CH$_2$COOCH$_3$ | 42 | 0.97 | 516.46 |
| 291 | H | CH$_3$ | CH$_3$ | CH$_2$CH$_2$COO—CH$_3$ | 42 | 0.98 | 530.46 |
| 293 | H | CH$_3$ | CH$_3$ | CH$_2$COOCH$_2$—CH$_3$ | 42 | 0.99 | 530.55 |
| 294 | H | CH$_3$ | CH$_3$ | CH$_2$CH$_2$COO—CH$_2$CH$_3$ | 42 | 1.00 | 544.48 |
| 297 | H | CH$_3$ | CH$_2$CH$_3$ | CH$_2$CH$_2$OH | 37 | 0.93 | 502.23 |
| 298 | H | CH$_3$ | CH$_3$ | COCH$_2$OH | 231 | 0.92 | 444.29 |
| 299 | H | CH$_3$ | CH$_2$CH$_3$ | COCH$_2$OH | 231 | 1.05 | 516.42 |
| 300 | H | CH$_2$CH$_3$ | CH$_2$CH$_3$ | COCH$_2$OH | 231 | 1.08 | 530.39 |
| 301 | H | CH$_3$ | Cl | COCH$_2$OH | 231 | 1.04 | 522.06 |
| 302 | H | OCH$_3$ | Cl | COCH$_2$OH | 231 | 1.04 | 538.35 |
| 303 | OCH$_3$ | H | H | COCH$_2$OH | 231 | 1.01 | 504.24 |
| 304 | H | CH$_3$ | CH$_3$ | COCH$_2$NH$_2$ | 238 | 0.90 | 501.16 |
| 305 | H | CH$_3$ | CH$_3$ | COCH$_2$NHCH$_3$ | 238 | 0.91 | 515.28 |
| 306 | H | CH$_3$ | CH$_3$ | COCH$_2$CH$_2$NH—CH$_3$ | 238 | 0.91 | 529.28 |
| 307 | H | CH$_3$ | CH$_2$CH$_3$ | COCH$_2$NH$_2$ | 238 | 0.93 | 515.49 |
| 308 | H | CH$_3$ | CH$_2$CH$_3$ | COCH$_2$NHCH$_3$ | 238 | 0.93 | 529.28 |
| 309 | H | CH$_3$ | CH$_2$CH$_3$ | COCH$_2$CH$_2$NH—CH$_3$ | 238 | 0.91 | 543.26 |
| 310 | H | CH$_2$CH$_3$ | CH$_2$CH$_3$ | COCH$_2$NHCH$_3$ | 238 | 0.92 | 543.40 |
| 311 | H | CH$_2$CH$_3$ | CH$_2$CH$_3$ | COCH$_2$CH$_2$NH—CH$_3$ | 238 | 0.93 | 557.40 |
| 312 | H | CH$_3$ | Cl | COCH$_2$NH$_2$ | 238 | 0.89 | 521.14 |
| 313 | H | CH$_3$ | Cl | COCH$_2$NHCH$_3$ | 238 | 0.92 | 535.50 |
| 314 | H | CH$_3$ | Cl | COCH$_2$CH$_2$NH—CH$_3$ | 238 | 0.92 | 549.40 |
| 315 | H | OCH$_3$ | Cl | COCH$_2$NH$_2$ | 238 | 0.89 | 537.11 |
| 316 | H | OCH$_3$ | Cl | COCH$_2$NHCH$_3$ | 238 | 0.90 | 551.13 |
| 317 | H | OCH$_3$ | Cl | COCH$_2$CH$_2$NH—CH$_3$ | 238 | 0.90 | 565.15 |
| 318 | OCH$_3$ | H | H | COCH$_2$NHCH$_3$ | 238 | 0.89 | 517.21 |
| 319 | OCH$_3$ | H | H | COCH$_2$CH$_2$NH—CH$_3$ | 238 | 0.89 | 531.20 |

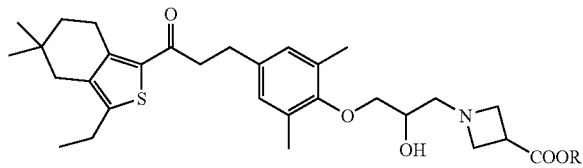

| Example | R | prepared in analogy to Example | LC-MS $t_R$ (min) | $[M + H]^+$ |
|---|---|---|---|---|
| 292 | CH$_3$ | 42 | 0.98 | 542.48 |
| 295 | CH$_2$CH$_3$ | 42 | 0.99 | 556.54 |
| 296 | H | 42 | 0.94 | 528.08 |

Example 295

As Formate Salt $^1$H NMR (CDCl$_3$): δ 8.32 (s br, 1H), 6.87 (s, 2H), 5.92 (s br, 1H), 4.50-4.30 (m, 3H), 4.23 (q, J=7.0 Hz, 2H), 4.11 (dd, J=8.2, 10.0 Hz, 1H), 4.03 (dd, J=7.6, 10.0 Hz, 1H), 3.81-3.65 (m, 3H), 3.41 (dd, J=2.9, 12.9 Hz, 1H), 3.31 (dd, J=2.9, 12.3 Hz, 1H), 3.08-3.00 (4H), 2.95-2.88 (m, 2H), 2.72 (q, J=7.6 Hz, 2H), 2.30 8 s, 2H), 2.22 (s, 6H), 1.54 (t, J=6.4 Hz, 2H), 1.29 (t, J=7.6 Hz, 3H), 1.26 (t, J=7.6 Hz, 3H), 0.97 (s, 6H).

Example 320

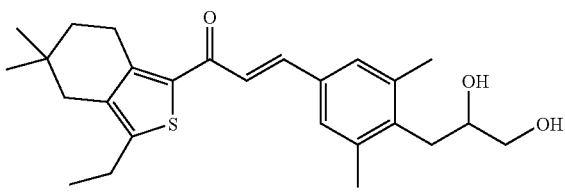

a) A solution of 2,5-dibromoxylene (8.0 g, 30.3 mmol) in diethyl ether (120 mL) is cooled to −78° C. and then treated with n-buthyllithium (20 mL, 1.6 M in hexane). After stirring for 40 min, DMF (6 mL) is slowly added. The mixture is warmed to rt and stirred for 1 h. The mixture is cooled again to −78° C. before another portion of n-butyllithium (5 mL) is added. The reaction mixture is allowed to warm to rt and stirred for another hour. The reaction is quenched by adding 5% aq. HCl. The mixture is extracted with EA, and the extract is concentrated in vacuo. The crude product is purified by CC on silica gel eluting with heptane:EA 5:1 to give 4-bromo-3,5-dimethyl-benzaldehyde (8.2 g) as a white soft solid.

b) A solution of 4-bromo-3,5-dimethyl-benzaldehyde (8.15 g, 38.25 mmol), p-toluenesulfonic acid (50 mg) and 1,3-propanediol (9.5 mL) in toluene (100 mL) is heated to 110° C. for 3 h. The reaction flask is equipped with a Dean-Stark apparatus and heating is continued at 110° C. for 16 h. The reaction mixture is cooled to rt, washed with sat. aq. NaHCO$_3$ and the solvent is removed in vacuo. The crude product is purified by CC on silica gel eluting with heptane: EA 9:1 to give 2-(4-bromo-3,5-dimethyl-phenyl)-[1,3]dioxane (5.97 g) as a colourless oil.

c) The corresponding Grignard-reagent is prepared form 2-(4-bromo-3,5-dimethyl-phenyl)-[1,3]dioxane (2.5 g, 9.22 mmol) and Mg (258 mg, 10.6 mmol) in THF (50 mL). To this reagent allylbromide (1.23 g, 10.14 mmol) is added dropwise at rt. The reaction mixture becomes warm (40° C.) and it is stirred for 16 h. The reaction is quenched by adding water. The mixture is extracted with EA. The organic extract is dried over MgSO$_4$, filtered and concentrated. The crude product is purified by CC on silica gel eluting with heptane:EA 10:1 to give 2-(4-allyl-3,5-dimethyl-phenyl)-[1,3]dioxane (1.8 g) as a colourless oil; LC-MS: $t_R$=1.02 min, [M+1]$^+$=233.22, $^1$H NMR (CDCl$_3$): δ 7.12 (s, 2H), 5.94-5.80 (m, 1H), 5.44 s, 1H), 4.95 (dd, J=1.8, 10.0 Hz, 1H), 4.80 (dd, J=1.8, 17.0 Hz, 1H), 4.30-4.21 (m, 2H), 4.04-3.92 (m, 2H), 3.40-3.34 (m, 2H), 2.32-2.26 (m, 8H).

d) A solution of 2-(4-allyl-3,5-dimethyl-phenyl)-[1,3]dioxane (790 mg, 3.4 mmol) in acetone (10 mL) is treated with OsO$_4$ (1 mL of a 2.5% solution in tert. butanol), NMO hydrate (551 mg, 4.08 mmol) and water (0.5 mL). The mixture is stirred at rt for 2.5 h before it is diluted with DCM, washed with 10% aq. citric acid solution (2×50 mL), dried over MgSO$_4$, filtered and evaporated. The product is crystallized from DCM/heptane to give 3-(4-[1,3]dioxan-2-yl-2,6-dimethyl-phenyl)-propane-1,2-diol (335 mg) as a grey powder; $^1$H NMR (CDCl$_3$): δ 7.15 (s, 2H), 5.42 8 s, 1H), 4.26 (dd, J=4.6, 10.6 Hz, 2H), 3.98 (dt, J$_d$=1.8 Hz, J$_t$=12.3 Hz, 2H), 3.92-3.81 (m, 2H), 3.66 (dd, J=2.9, 11.1 Hz, 1H), 3.55 (dd, J=7.0 11.1 Hz, 1H), 2.88 (dd, J=8.8, 14.1 Hz, 1H), 2.74 (dd, J=5.3, 13.5 Hz, 1H), 2.34 (s, 6H), 2.30-2.14 (m, 2H), 1.90 (s br, 2H).

e) A solution of 3-ethyl-5,5-dimethyl-4,5,6,7-tetrahydro-benzo[c]thiophene-1-carboxylic acid (65 mg, 0.275 mmol) and 3-(4-[1,3]dioxan-2-yl-2,6-dimethyl-phenyl)-propane-1,2-diol (95 mg, 0.356 mmol) in ethanol (2 mL) and 4 N HCl in isopropanol (0.5 mL) is stirred at rt for 1 week. The solvent is evaporated and the crude product is purified by chromatography on prep. TLC plates with EA to give 3-[4-(2,3-dihydroxy-propyl)-3,5-dimethyl-phenyl]-1-(3-ethyl-5,5-dimethyl-4,5,6,7-tetrahydro-benzo[c]thiophen-1-yl)-propenone (82 mg) as a yellow resin; LC-MS: $t_R$=1.11 min, [M+1]= 427.36.

Example 321

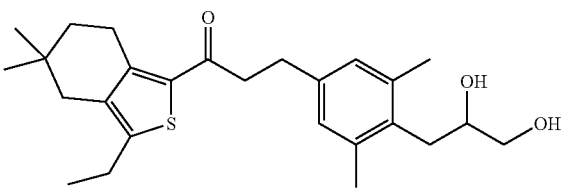

To a solution of 3-[4-(2,3-dihydroxy-propyl)-3,5-dimethyl-phenyl]-1-(3-ethyl-5,5-dimethyl-4,5,6,7-tetrahydro-benzo[c]thiophen-1-yl)-propenone (82 mg) in ethanol (5 mL), Pd/C (30 mg, 10% Pd) is added and the suspension is stirred for 18 h at rt under 1 bar of H$_2$. The catalyst is filtered off and the solvent of the filtrate is evaporated. The crude product is purified by chromatography on prep. TLC plates with EA to afford 3-[4-(2,3-dihydroxy-propyl)-3,5-dimethyl-phenyl]-1-(3-ethyl-5,5-dimethyl-4,5,6,7-tetrahydro-benzo

[c]thiophen-1-yl)-propan-1-one (15 mg) as beige resin; LC-MS: $t_R$=1.10 min, [M+1]=429.38.

Examples 322 to 333

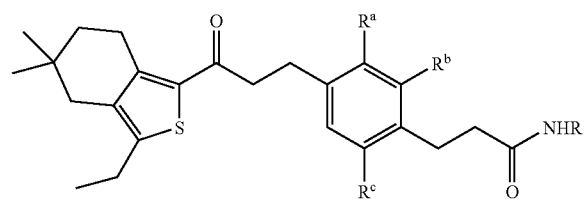

The following examples are prepared starting from Intermediate 4 and Intermediate 5, respectively, and the appropriate amines in analogy to Example 135. Amino acids are coupled as their carboxylic acid esters which are cleaved in a second step following the coupling reaction by stirring the corresponding ester in methanol in the presence of 2 N aq. NaOH at rt for 1 h. The reaction mixtures are separated by prep. HPLC (Phenomenex Gemini C18, 5 μm 110 A, 20-95% acetonitrile in water containing 0.5% of formic acid) to afford the desired 3-{4-[3-(3-ethyl-5,5-dimethyl-4,5,6,7-tetrahydro-benzo[c]thiophen-1-yl)-3-oxo-propyl]-phenyl}-propionamides as colourless resins.

| Example | $R^a$ | $R^b$ | $R^c$ | R | LC-MS $t_R$ (min) | [M + H]$^+$ |
|---|---|---|---|---|---|---|
| 322 | H | CH$_3$ | CH$_3$ | H | 1.14 | 426.35 |
| 323 | H | CH$_3$ | CH$_3$ | CH$_2$CH$_2$OH | 1.09 | 470.41 |
| 324 | H | CH$_3$ | CH$_3$ | CH$_2$CH$_2$CH$_2$OH | 1.11 | 484.50 |
| 325 | H | CH$_3$ | CH$_3$ | CH(CH$_2$OH)$_2$ | 1.04 | 500.07 |
| 326 | H | CH$_3$ | CH$_3$ | CH$_2$COOCH$_3$ | 1.15 | 498.40 |
| 327 | H | CH$_3$ | CH$_3$ | CH$_2$CH$_2$COOCH$_3$ | 1.16 | 512.43 |
| 328 | H | CH$_3$ | CH$_3$ | CH$_2$COOH | 1.08 | 484.39 |
| 329 | H | CH$_3$ | CH$_3$ | CH$_2$CH$_2$COOH | 1.09 | 498.39 |
| 330 | H | CH$_3$ | CH$_2$CH$_3$ | CH$_2$CH$_2$OH | 1.10 | 484.46 |
| 331 | H | CH$_3$ | CH$_2$CH$_3$ | CH(CH$_2$OH)$_2$ | 1.05 | 514.45 |
| 332 | H | CH$_3$ | CH$_2$CH$_3$ | CH$_2$COOCH$_3$ | 1.16 | 512.45 |
| 333 | H | CH$_3$ | CH$_2$CH$_3$ | CH$_2$COOH | 1.05 | 514.45 |

Example 334

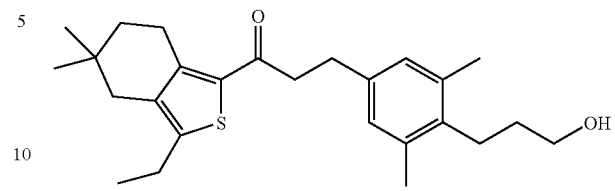

1-(3-Ethyl-5,5-dimethyl-4,5,6,7-tetrahydro-benzo[c]thiophen-1-yl)-3-[4-(3-hydroxy-propyl)-3,5-dimethyl-phenyl]-propenone is prepared in analogy to Example 15 by condensing Example R and Aldehyde 7; LC-MS: $t_R$=1.19 min, [M+1]$^+$=411.48.

Example 335

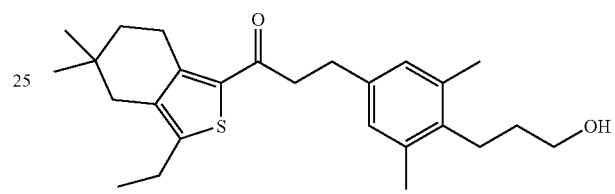

In analogy to Example 16, hydrogenation of Example 334 affords 1-(3-ethyl-5,5-dimethyl-4,5,6,7-tetrahydro-benzo[c]thiophen-1-yl)-3-[4-(3-hydroxy-propyl)-3,5-dimethyl-phenyl]-propan-1-one; LC-MS: $t_R$=1.17 min, [M+1]$^+$=413.40.

Example 336

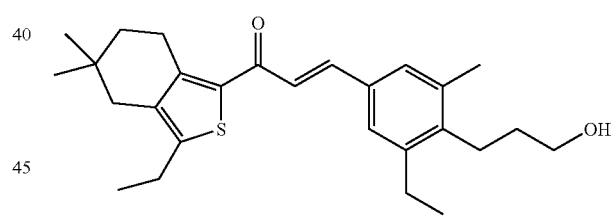

1-(3-Ethyl-5,5-dimethyl-4,5,6,7-tetrahydro-benzo[c]thiophen-1-yl)-3-[4-(3-hydroxy-propyl)-3-ethyl-5-methyl-phenyl]-propenone is prepared in analogy to Example 15 by condensing Example R and Aldehyde 8; LC-MS: $t_R$=1.21 min, [M+1]$^+$=425.40.

Example 337

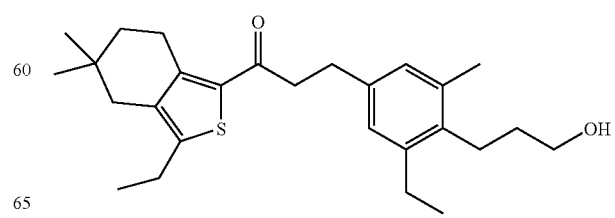

In analogy to Example 16, hydrogenation of Example 336 affords 1-(3-ethyl-5,5-dimethyl-4,5,6,7-tetrahydro-benzo[c]thiophen-1-yl)-3-[4-(3-hydroxy-propyl)-3-ethyl-5-methyl-phenyl]-propan-1-one; LC-MS: $t_R$=1.19 min, $[M+1]^+$= 427.40.

Example 338

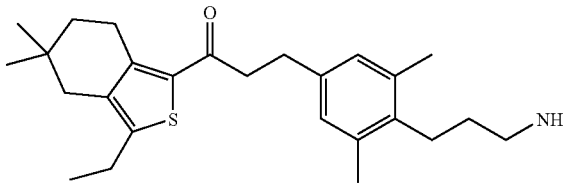

a) A solution of 1-(3-ethyl-5,5-dimethyl-4,5,6,7-tetrahydro-benzo[c]thiophen-1-yl)-3-[4-(3-hydroxy-propyl)-3,5-dimethyl-phenyl]-propan-1-one (135 mg, 0.328 mmol, Example 335) in DCM is treated with DIPEA (70 mg, 0.525 mmol) followed by methanesulfonylchloride (45 mg, 0.394 mmol). The mixture is stirred at rt for 1.5 h before it is diluted with DCM and washed with 0.5 M aq. citric acid solution followed by brine. The organic extract is dried over MgSO$_4$, filtered and the solvent of the filtrate is evaporated to give methanesulfonic acid 3-{4-[3-(3-ethyl-5,5-dimethyl-4,5,6,7-tetrahydro-benzo[c]thiophen-1-yl)-3-oxo-propyl]-2,6-dimethyl-phenyl}-propyl ester (165 mg) as a yellow resin; LC-MS: $t_R$=1.20 min, $[M+1]^+$=491.36.

b) A solution of methanesulfonic acid 3-{4-[3-(3-ethyl-5,5-dimethyl-4,5,6,7-tetrahydro-benzo[c]thiophen-1-yl)-3-oxo-propyl]-2,6-dimethyl-phenyl}-propyl ester (160 mg, 0.326 mmol) in 7 N NH$_3$ in methanol is stirred at 70° C. for 16 h in a sealed vial. The solvent is removed and the residue is purified by CC on silica gel eluting with DCM containing 7% of methanol to give 3-[4-(3-amino-propyl)-3,5-dimethyl-phenyl]-1-(3-ethyl-5,5-dimethyl-4,5,6,7-tetrahydro-benzo[c]thiophen-1-yl)-propan-1-one (101 mg) as a pale yellow resin; LC-MS: $t_R$=0.95 min, $[M+1]^+$=412.36; $^1$H NMR (CDCl$_3$): δ 6.87 (s, 2H), 3.09-3.00 (m, 4H), 2.97-2.88 (m, 4H), 2.76-2.60 (m, 6H), 2.30 (s, 2H), 2.28 (s, 6H), 1.80-1.70 (m, 2H), 1.54 (t, J=7.0 Hz, 2H), 1.26 (t, J=7.6 Hz, 3H), 0.96 (s, 6H).

Example 339

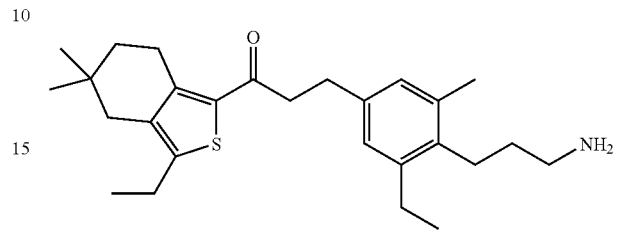

3-[4-(3-Amino-propyl)-3-ethyl-5-methyl-phenyl]-1-(3-ethyl-5,5-dimethyl-4,5,6,7-tetrahydro-benzo[c]thiophen-1-yl)-propan-1-one is prepared in analogy to Example 338 starting from Example 337; LC-MS: $t_R$=0.97 min, $[M+1]^+$=426.45.

Examples 340 to 351

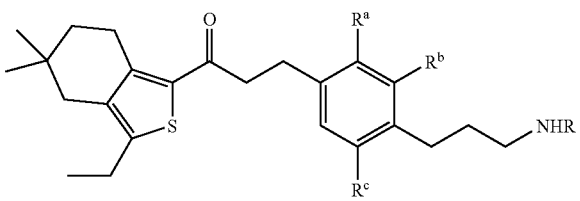

The following examples are prepared either from Example 338 or from Example 339 in analogy to previous examples:

| Ex. | $R^a$ | $R^b$ | $R^c$ | R | prepared in analogy to Example | LC-MS $t_R$(min) | $[M + H]^+$ |
|---|---|---|---|---|---|---|---|
| 340 | H | CH$_3$ | CH$_3$ | COCH$_2$OH | 231 | 1.12 | 470.45 |
| 341 | H | CH$_3$ | CH$_3$ | COCH$_2$CH$_2$OH | 231 | 1.11 | 484.39 |
| 342 | H | CH$_3$ | CH$_3$ | COCH$_2$NH$_2$ | 238 | 0.96 | 469.44 |
| 343 | H | CH$_3$ | CH$_3$ | COCH$_2$NHCH$_3$ | 238 | 0.97 | 483.47 |
| 344 | H | CH$_3$ | CH$_3$ | COCH$_2$CH$_2$NH$_2$ | 238 | 0.97 | 483.44 |
| 345 | H | CH$_3$ | CH$_3$ | COCH$_2$CH$_2$NHCH$_3$ | 238 | 0.97 | 497.42 |
| 346 | H | CH$_3$ | CH$_2$CH$_3$ | COCH$_2$OH | 231 | 1.14 | 484.44 |
| 347 | H | CH$_3$ | CH$_2$CH$_3$ | COCH$_2$CH$_2$OH | 231 | 1.13 | 498.43 |
| 348 | H | CH$_3$ | CH$_2$CH$_3$ | COCH$_2$NH$_2$ | 238 | 0.97 | 483.40 |
| 349 | H | CH$_3$ | CH$_2$CH$_3$ | COCH$_2$NHCH$_3$ | 238 | 0.98 | 497.50 |
| 350 | H | CH$_3$ | CH$_2$CH$_3$ | COCH$_2$CH$_2$NH$_2$ | 238 | 0.98 | 497.49 |
| 351 | H | CH$_3$ | CH$_2$CH$_3$ | COCH$_2$CH$_2$NHCH$_3$ | 238 | 0.99 | 511.47 |

Example 352

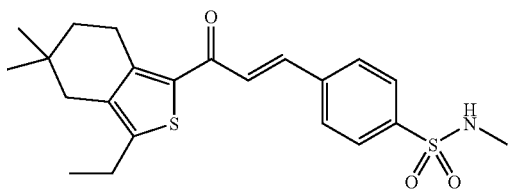

4-[3-(3-Ethyl-5,5-dimethyl-4,5,6,7-tetrahydro-benzo[c] thiophen-1-yl)-3-oxo-propenyl]-N-methyl-benzenesulfonamide is prepared in analogy to Example 15 by condensing Example R and Aldehyde 9; LC-MS: $t_R$=1.12 min, $[M+1]^+$= 418.25.

Example 353

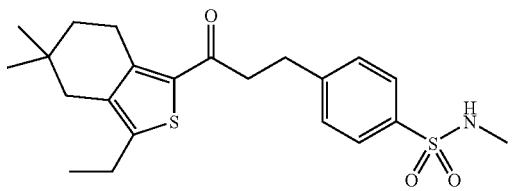

In analogy to Example 16, hydrogenation of Example 352 affords 4-[3-(3-ethyl-5,5-dimethyl-4,5,6,7-tetrahydro-benzo [c]thiophen-1-yl)-3-oxo-propyl]-N-methyl-benzenesulfonamide; LC-MS: $t_R$=1.11 min, $[M+1]^+$=420.25.

Example 354

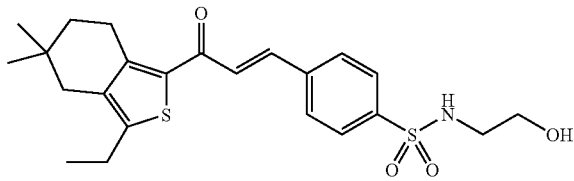

4-[3-(3-Ethyl-5,5-dimethyl-4,5,6,7-tetrahydro-benzo[c] thiophen-1-yl)-3-oxo-propenyl]-N-(2-hydroxy-ethyl)-benzenesulfonamide is prepared in analogy to Example 15 by condensing Example R and Aldehyde 10; LC-MS: $t_R$=1.06 min, $[M+1]^+$=448.42.

Example 355

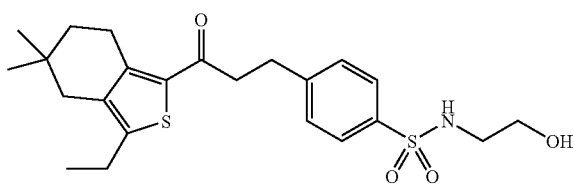

In analogy to Example 16, hydrogenation of Example 354 affords 4-[3-(3-ethyl-5,5-dimethyl-4,5,6,7-tetrahydro-benzo [c]thiophen-1-yl)-3-oxo-propyl]-N-(2-hydroxy-ethyl)-benzenesulfonamide; LC-MS: $t_R$=1.03 min, $[M+1]^+$=450.25.

Example 356

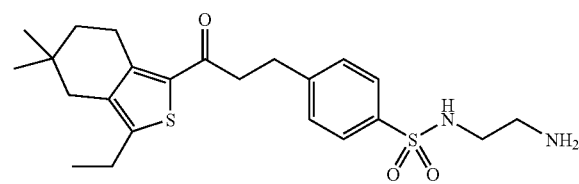

In analogy to Example 83, mesylating the alcohol functionality in Example 355 and subsequent substitution of the thus obtained mesylate with $NH_3$ in methanol at 65° C. affords N-(2-amino-ethyl)-4-[3-(3-ethyl-5,5-dimethyl-4,5,6, 7-tetrahydro-benzo[c]thiophen-1-yl)-3-oxo-propyl]-benzenesulfonamide; LC-MS: $t_R$=0.88 min, $[M+1]^+$=449.28.

Example 357

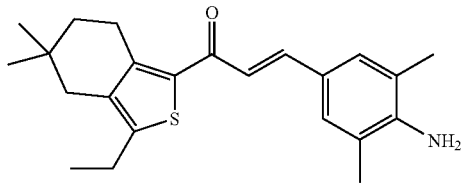

3-(4-Amino-3,5-dimethyl-phenyl)-1-(3-ethyl-5,5-dimethyl-4,5,6,7-tetrahydro-benzo[c]thiophen-1-yl)-propenone is obtained as a yellow oil by condensing Example R and Aldehyde 11 under basic conditions as described for Intermediate 2; LC-MS: $t_R$=1.17 min, $[M+1]^+$=368.30.

Example 358

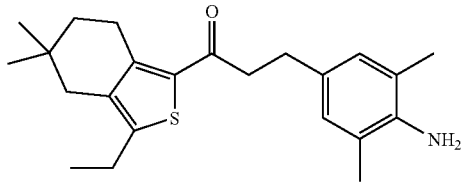

In analogy to Example 16, hydrogenation of Example 357 affords 3-(4-amino-3,5-dimethyl-phenyl)-1-(3-ethyl-5,5-dimethyl-4,5,6,7-tetrahydro-benzo[c]thiophen-1-yl)-propan-1-one; LC-MS: $t_R$=0.98 min, $[M+1]^+$=370.32.

Examples 359 to 363

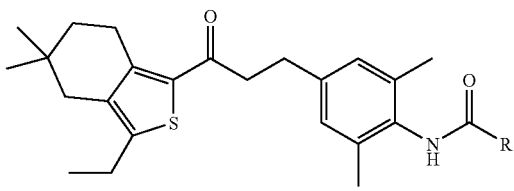

In case R constitutes an hydroxyalkane: To a solution of 3-(4-amino-3,5-dimethyl-phenyl)-1-(3-ethyl-5,5-dimethyl-4,5,6,7-tetrahydro-benzo[c]thiophen-1-yl)-propan-1-one (7.5 mg, 20 µmol) in THF:DMF 1:1 (1 mL) the appropriate hydroxyalkylcarboxylic acid (50 µmol) and EDC (9.5 mg, 50 µmol) is added. The mixture is stirred at 50° C. for 16 h and then separated by prep. HPLC (Waters Symmetry, 50×20 mm ID, 5 µm, 20-95% acetonitrile in water containing 0.5% of formic acid) to afford the desired N-{4-[3-(3-ethyl-5,5-dimethyl-4,5,6,7-tetrahydro-benzo[c]thiophen-1-yl)-3-oxo-propyl]-2,6-dimethyl-phenyl}-amide as a colourless resin.

In case R constitutes an aminoalkane: To a solution of 3-(4-amino-3,5-dimethyl-phenyl)-1-(3-ethyl-5,5-dimethyl-4,5,6,7-tetrahydro-benzo[c]thiophen-1-yl)-propan-1-one (7.5 mg, 20 µmol) and DIPEA (5 mg, 40 µmol) in THF (0.2 mL) chloroacetylchloride (2.5 mg, 22 µmol) is added. The mixture is stirred at rt for 2 h before the appropriate amine (60 µmol) is added. The mixture is stirred at 70° C. for 12 h before it is diluted with acetic acid (0.2 mL) and methanol (0.25 mL) and separated by prep. HPLC (Waters Symmetry, 50×20 mm ID, 5 µm, 20-95% acetonitrile in water containing 0.5% of formic acid) to afford the desired N-{4-[3-(3-ethyl-5,5-dimethyl-4,5,6,7-tetrahydro-benzo[c]thiophen-1-yl)-3-oxo-propyl]-2,6-dimethyl-phenyl}-amide as a colourless resin.

| | | LC-MS | |
|---|---|---|---|
| Example | R | $t_R$ (min) | $[M + H]^+$ |
| 359 | $CH_2OH$ | 1.20 | 428.34 |
| 360 | $CH_2CH_2OH$ | 1.19 | 442.40 |
| 361 | $CH_2NH_2$ | 0.91 | 427.38 |
| 362 | $CH_2NHCH_3$ | 09.2 | 441.44 |
| 363 | $CH_2N(CH_3)_2$ | 0.93 | 455.45 |

Example 364

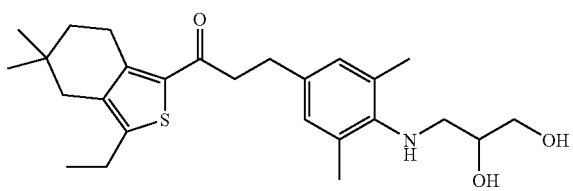

a) To a solution of 3-(4-amino-3,5-dimethyl-phenyl)-1-(3-ethyl-5,5-dimethyl-4,5,6,7-tetrahydro-benzo[c]thiophen-1-yl)-propan-1-one (296 mg, 0.80 mmol) in DMF (5 mL) allyl-bromide (121 mg, 1.00 mmol) and $NaHCO_3$ (144 mg, 1.71 mmol) is added. The mixture is stirred at 80° C. for 4 h before it is filtered. The filtrate is separated by prep. HPLC (Waters Xterra C18 75×30 mm 10 µm, 10-95% acetonitrile in water containing 0.8% of diethylamine) to afford 3-(4-allylamino-3,5-dimethyl-phenyl)-1-(3-ethyl-5,5-dimethyl-4,5,6,7-tetrahydro-benzo[c]thiophen-1-yl)-propan-1-one (80 mg) as a yellow resin; LC-MS: $t_R$=0.98 min, $[M+1]^+$=410.20.

b) To a solution of 3-(4-allylamino-3,5-dimethyl-phenyl)-1-(3-ethyl-5,5-dimethyl-4,5,6,7-tetrahydro-benzo[c]thiophen-1-yl)-propan-1-one (80 mg, 0.195 mmol) and NMO (69 mg, 0.507 mmol) in acetone (11.5 mL) and water (1.65 mL), a 2.5 M solution of $OsO_4$ in tert. butanol (88 µL, 7 µmol) is added. The mixture is stirred at rt for 18 h and then separated by prep. HPLC (Waters Symmetry C18 19×50 mm 5 µm, 10-95% acetonitrile in water containing 0.5% of 25% aq. $NH_3$) to afford 3-[4-(2,3-dihydroxy-propylamino)-3,5-dimethyl-phenyl]-1-(3-ethyl-5,5-dimethyl-4,5,6,7-tetrahydro-benzo[c]thiophen-1-yl)-propan-1-one (52 mg) as a pyle yellow solid; LC-MS: $t_R$=0.90 min, $[M+1]^+$=444.41; $^1$H NMR ($CDCl_3$): δ 6.98 (s, 2H), 3.92-3.84 (m, 1H), 3.80 (dd, J=3.5, 11.1 Hz, 1H), 3.72 (dd, J=4.7, 11.1 Hz, 1H), 3.14-2.88 (m, 7H), 2.72 (q, J=7.6 Hz, 2H), 2.30 (s, 2H), 2.29 (s, 6H), 1.54 (t, J=6.4 Hz, 2H), 1.26 (t, J=7.6 Hz, 3H), 0.96 (s, 6H).

Examples 365 to 367

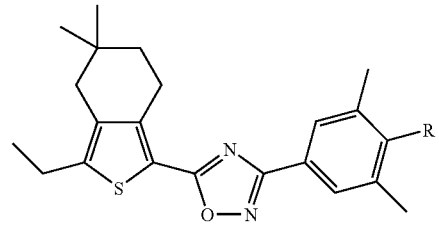

The following examples are prepared in analogy to previous examples using Example E and Hydroxyamidine 1:

| | | prepared in analogy to Example | LC-MS | |
|---|---|---|---|---|
| Example | R | | $t_R$ (min) | $[M + H]^+$ |
| 365 | OH | 127 | 1.22 | 383.32 |
| 366 | ![](O\~\~\~NH2, HO) | 128 | 0.95 | 456.39 |
| 367 | C(O)CH2OH, HO) | 129 | 1.11 | 514.34 |

Examples 368 to 370

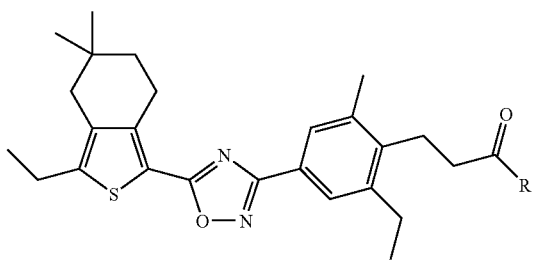

The following examples are prepared in analogy to previous examples using Intermediate 6:

| Example | R | prepared in analogy to Example | LC-MS $t_R$ (min) | [M + H]⁺ |
|---|---|---|---|---|
| 368 | HN⌒OH | 135 | 1.17 | 496.46 |
| 369 | HN⌒CH(OH)CH₂OH | 136 | 1.13 | 526.29 |
| 370 | HN⌒CH(OH)CH₂OH | 136 | 1.12 | 526.30 |

Example 371

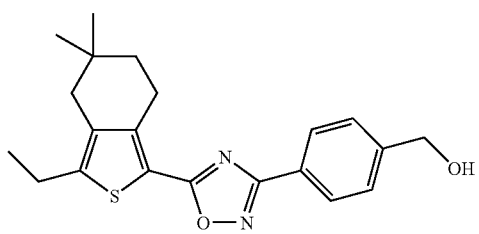

{4-[5-(3-Ethyl-5,5-dimethyl-4,5,6,7-tetrahydro-benzo[c]thiophen-1-yl)-[1,2,4]oxadiazol-3-yl]-phenyl}-methanol is prepared starting from Example E and Hydroxyamidine 4 in analogy to Example 127; LC-MS: $t_R$=1.15 min, [M+1]⁺= 369.26.

Example 372

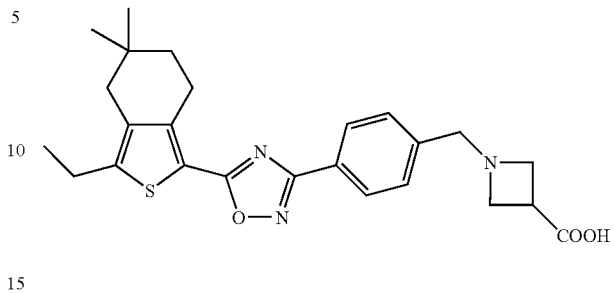

a) To a cold solution (−70° C.) of oxalyl chloride (169 mg, 1.34 mmol) and DMSO (209 mg, 2.67 mmol) in DCM (4 mL) a solution of {4-[5-(3-ethyl-5,5-dimethyl-4,5,6,7-tetrahydro-benzo[c]thiophen-1-yl)-[1,2,4]oxadiazol-3-yl]-phenyl}-methanol (410 mg, 1.11 mmol) in DCM (5 mL) is added. The mixture is warmed to −40° C. within 30 min and then triethylamine (394 mg, 3.89 mmol) is added. Stirring is continued at −40° C. for 1 h, then at rt. The reaction is quenched by adding water and the mixture is extracted with diethyl ether. The organic extract is dried over MgSO₄, filtered and the solvent of the filtrate is evaporated. The crude product is purified by chromatography on prep. TLC plates with heptane:EA 3:1 to give 4-[5-(3-ethyl-5,5-dimethyl-4,5,6,7-tetrahydro-benzo[c]thiophen-1-yl)-[1,2,4]oxadiazol-3-yl]-benzaldehyde (180 mg) as a white solid; LC-MS: $t_R$=1.24 min, [M+1]⁺=367.24.

b) To a solution of 4-[5-(3-ethyl-5,5-dimethyl-4,5,6,7-tetrahydro-benzo[c]thiophen-1-yl)-[1,2,4]oxadiazol-3-yl]-benzaldehyde (180 mg, 0.49 mmol) in DCM (10 mL) and methanol (10 mL) azetidine-3-carboxylic acid (60 mg, 0.589 mmol) and NaBH(OAc)₃ (104 mg, 0.491 mmol) is added at 5° C. The reaction mixture is stirred at 5° C. for 3 h. The solvent is evaporated and the crude product is purified by chromatography on prep. TLC plates using DCM containing 20% of methanol to give 1-{4-[5-(3-ethyl-5,5-dimethyl-4,5,6,7-tetrahydro-benzo[c]thiophen-1-yl)-[1,2,4]oxadiazol-3-yl]-benzyl}-azetidine-3-carboxylic acid (50 mg) as a pale yellow solid; LC-MS: $t_R$=0.93 min, [M+1]⁺=452.27.

Examples 373 to 399

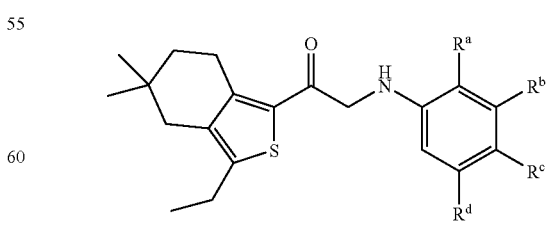

The following examples are prepared in analogy to Example 155 starting from Bromoketone 2 and the appropriate anilines:

| Example | $R^a$ | $R^b$ | $R^c$ | $R^d$ | $t_R$ (min) | $[M+H]^+$ |
|---|---|---|---|---|---|---|
| 373 | H | H | H | H | 1.15 | 328.28 |
| 374 | CH₃ | H | H | H | 1.19 | 342.31 |
| 375 | CH₂CH₃ | H | H | H | 1.22 | 356.36 |
| 376 | H | CH₃ | H | CH₃ | 1.19 | 356.30 |
| 377 | H | CF₃ | H | H | 1.21 | 396.35 |
| 378 | OCH₃ | H | H | H | 1.18 | 358.38 |
| 379 | H | H | OCH₃ | H | 1.05 | 358.27 |
| 380 | CH₃ | H | OCH₃ | H | 1.14 | 372.32 |
| 381 | OCH₃ | H | OCH₃ | H | 1.09 | 388.40 |
| 382 | OCH₃ | H | H | CF₃ | 1.23 | 426.23 |
| 383 | H | OCH₃ | H | CF₃ | 1.21 | 426.20 |
| 384 | H | H | OCH₃ | CF₃ | 1.19 | 426.29 |
| 385 | CH₃ | H | H | CF₃ | 1.23 | 410.18 |
| 386 | H | H | (R/S)-OCH₂CH(OH)— (propan-2-ol ether, dashed bond) | H | 1.05 | 372.29 |
| 387 | H | H | —OCH₂CH₂OH | H | 0.96 | 388.37 |
| 388 | H | H | —OCH₂CH₂CH₂OH | H | 0.98 | 402.24 |
| 389 | H | H | —OCH₂CH(OH)CH₃ | H | 0.99 | 402.23 |
| 390 | H | H | —OCH₂CH(OH)CH₂OH (S) | H | 0.90 | 418.19 |
| 391 | H | H | —OCH₂CH₂N(CH₃)₂ | H | 0.73 | 415.30 |
| 392 | H | H | —OCH₂CH₂-morpholinyl | H | 0.88 | 457.40 |
| 393 | CH₃ | H | —OCH₂CH₂OH | H | 1.05 | 402.28 |
| 394 | CH₃ | H | —OCH₂CH₂CH₂OH | H | 1.07 | 416.30 |
| 395 | CH₃ | H | —OCH₂CH(OH)CH₃ | H | 1.05 | 402.23 |
| 396 | CH₃ | H | —OCH₂CH(OH)CH₂OH (S) | H | 0.95 | 418.23 |
| 397 | CH₃ | H | —OCH₂CH(OH)CH₂OH (R) | H | 0.95 | 418.26 |
| 398 | CH₃ | H | —OCH₂CH₂N(CH₃)₂ | H | 0.74 | 429.37 |
| 399 | CH₃ | H | —OCH₂CH₂-morpholinyl | H | 0.92 | 471.47 |

Examples 400 to 407

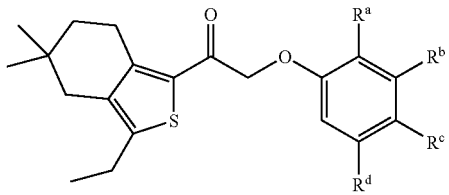

The following examples are prepared in analogy to Example 180 starting from Bromoketone 2 and the appropriate phenols:

| Example | $R^a$ | $R^b$ | $R^c$ | $R^d$ | LC-MS $t_R$ (min) | $[M+H]^+$ |
|---|---|---|---|---|---|---|
| 400 | H | H | H | H | 1.16 | 329.30 |
| 401 | H | CH$_3$ | H | CH$_3$ | 1.20 | 357.27 |
| 402 | OCH$_3$ | H | H | H | 1.14 | 359.32 |
| 403 | CH$_2$CH$_3$ | H | H | H | 1.21 | 357.30 |
| 404 | H | CF$_3$ | H | H | 1.20 | 397.30 |
| 405 | H | H | OCH$_3$ | H | 1.15 | 359.31 |
| 406 | H | H | ⁓⁓⁓OH (propyl-OH) | H | 1.08 | 373.32 |
| 407 | OCH$_3$ | H | —CH$_2$OH | H | 1.05 | 389.30 |

Example 408

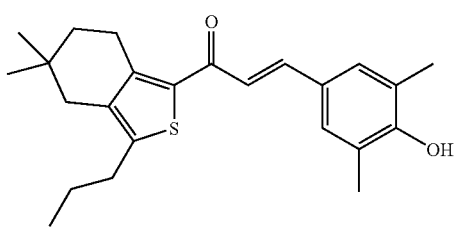

1-(5,5-Dimethyl-3-propyl-4,5,6,7-tetrahydro-benzo[c]thiophen-1-yl)-3-(4-hydroxy-3,5-dimethyl-phenyl)-propenone is prepared in analogy to Example 22 by condensing Example V and 3,5-dimethyl-4-hydroxybenzaldehyde; LC-MS: $t_R$=1.20 min, $[M+1]^+$=383.31.

Example 409

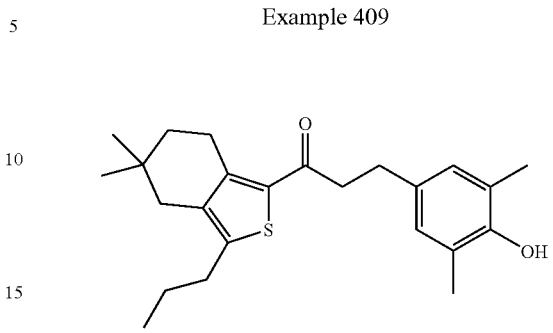

1-(5,5-Dimethyl-3-propyl-4,5,6,7-tetrahydro-benzo[c]thiophen-1-yl)-3-(4-hydroxy-3,5-dimethyl-phenyl)-propanone is prepared in analogy to Example 23 from Example 408; LC-MS: $t_R$=1.18 min, $[M+1]^+$=385.38; $^1$H NMR (CDCl$_3$): δ 6.85 (s, 2H), 4.50 (s br, 1H), 3.07-3.00 (m, 4H), 2.93-2.86 (m, 2H), 2.70-2.64 (m, 2H), 2.30 (s, 2H), 2.22 (s, 6H), 1.72-1.59 (m, 2H), 1.54 (t, J=6.4 Hz, 2H), 0.98 (t, J=7.6 Hz, 3H), 0.95 (s, 6H).

Examples 410 to 418

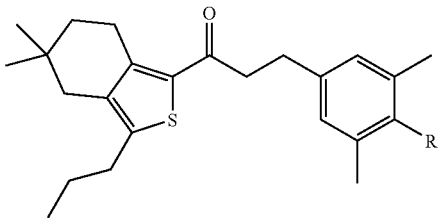

The following examples are prepared in analogy to previous examples starting from Example 409:

| Example | R | prepared in analogy to Example | LC-MS $t_R$ (min) | $[M+H]^+$ |
|---|---|---|---|---|
| 410 | –O–CH$_2$CH$_2$–OH | 24 | 1.17 | 429.43 |
| 411 | –O–CH$_2$CH(OH)CH$_3$ | 25 | 1.20 | 443.36 |
| 412 | –O–CH$_2$CH$_2$CH$_2$–OH | 26 | 1.19 | 443.35 |
| 413 | –O–CH$_2$CH(OH)CH$_2$OH | 27 | 1.11 | 459.37 |

-continued

| Example | R | prepared in analogy to Example | LC-MS $t_R$ (min) | [M + H]+ |
|---|---|---|---|---|
| 414 | -CH2-OH) | 28 | 1.11 | 459.43 |
| 415 | -CH2-O-Me) | 29 | 1.19 | 473.39 |
| 416 | 2) | 30 | 1.01 | 456.48 |
| 417 | | 31 | 1.03 | 482.44 |
| 418 | | 32 | 1.01 | 498.43 |

Example 419

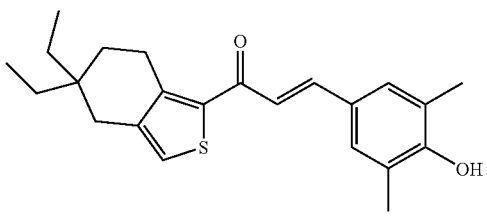

1-(5,5-Diethyl-4,5,6,7-tetrahydro-benzo[c]thiophen-1-yl)-3-(4-hydroxy-3,5-dimethyl-phenyl)-propenone is prepared in analogy to Example 22 by condensing Example W and 3,5-dimethyl-4-hydroxybenzaldehyde; LC-MS: $t_R$=1.17 min, [M+1]+=369.27, $^1$H NMR (CD$_3$OD): 7.62 (d, J=15.2 Hz, 1H), 7.34 (s, 1H), 7.28 (s, 2H), 7.23 (d, J=15.2 Hz, 1H), 3.07 (t, J=6.4 Hz, 2H), 2.53 (s, 2H), 2.24 (s, 6H), 1.63 (t, J=7.0 Hz, 2H), 1.42-1.25 (m, 4H), 0.86 (t, J=7.6 Hz, 6H).

Example 420

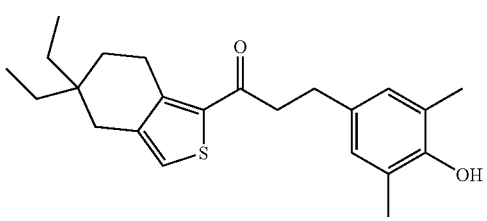

1-(5,5-Diethyl-4,5,6,7-tetrahydro-benzo[c]thiophen-1-yl)-3-(4-hydroxy-3,5-dimethyl-phenyl)-propanone is prepared in analogy to Example 23 from Example 419; LC-MS: $t_R$=1.16 min, [M+1]+=371.40; $^1$H NMR (CDCl$_3$): δ $^1$H NMR (CD$_3$OD): δ 7.26 (s, 1H), 6.76 (s, 2H), 3.08-3.01 (m, 2H), 2.95 (t, J=7.0 Hz, 2H), 2.82 (t, J=7.6 Hz, 2H), 2.49 (s, 2H), 2.16 (s, 6H), 1.60 (t, J=6.4 Hz, 2H), 1.38-1.20 (m, 4H), 0.84 (t, 7.6 Hz, 6H).

Example 421

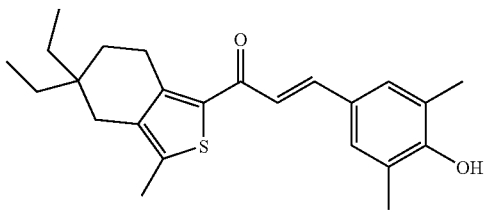

1-(5,5-Diethyl-3-methyl-4,5,6,7-tetrahydro-benzo[c]thiophen-1-yl)-3-(4-hydroxy-3,5-dimethyl-phenyl)-propenone is prepared in analogy to Example 22 by condensing Example X and 3,5-dimethyl-4-hydroxybenzaldehyde; LC-MS: $t_R$=1.20 min, [M+1]+383.30.

Example 422

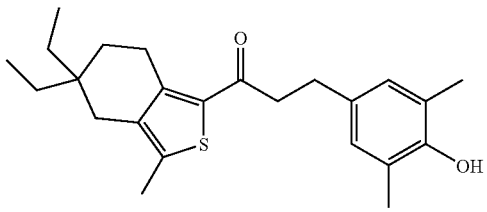

Hydrogenation of Example 421 in analogy to Example 23 affords 1-(5,5-diethyl-3-methyl-4,5,6,7-tetrahydro-benzo[c]thiophen-1-yl)-3-(4-hydroxy-3,5-dimethyl-phenyl)-propan-1-one; LC-MS: $t_R$=1.19 min, [M+1]+=385.27.

Example 423

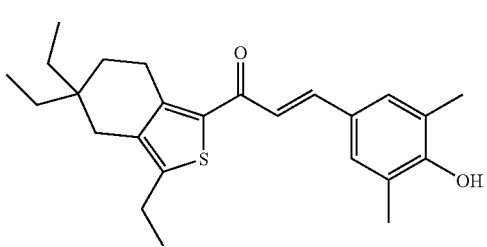

3-(4-Hydroxy-3,5-dimethyl-phenyl)-1-(3,5,5-triethyl-4,5,6,7-tetrahydro-benzo[c]thiophen-1-yl)-propenone is prepared in analogy to Example 22 by condensing Example X and 3,5-dimethyl-4-hydroxybenzaldehyde; LC-MS: $t_R$=1.22 min, [M+1]$^+$=397.32.

Example 424

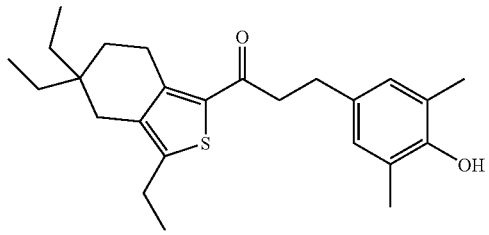

Hydrogenation of Example 421 in analogy to Example 23 affords 3-(4-hydroxy-3,5-dimethyl-phenyl)-1-(3,5,5-triethyl-4,5,6,7-tetrahydro-benzo[c]thiophen-1-yl)-propan-1-one; LC-MS: $t_R$=1.21 min, [M+1]$^+$=399.35.

Examples 425 to 430

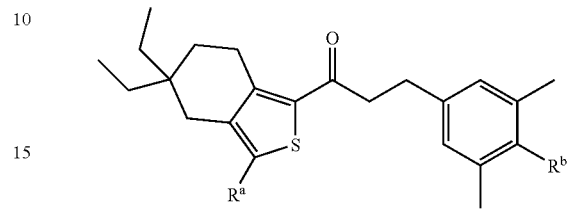

The following examples are prepared in analogy to previous examples starting from Example 420, 422, or 424:

| Ex. | R$^a$ | R$^b$ | starting from Example | prepared in analogy to Example | LC-MS $t_R$ (min) | [M + H]$^+$ |
|---|---|---|---|---|---|---|
| 425 | H | | 420 | 27 | 1.09 | 445.50 |
| 426 | CH$_3$ | | 422 | 27 | 1.11 | 459.40 |
| 427 | CH$_3$ | | 422 | 33 | 0.94 | 458.28 |
| 428 | CH$_3$ | | 422 | 146 | 1.06 | 516.48 |
| 429 | CH$_2$CH$_3$ | | 424 | 33 | 0.96 | 472.39 |
| 430 | CH$_2$CH$_3$ | | 424 | 146 | 1.09 | 530.41 |

Example 428

$^1$H NMR (CDCl$_3$): δ 7.16 (t br, J=6 Hz, 1H), 6.86 (s, 2H), 4.15-4.07 (m, 3H), 3.82-3.68 (m, 3H), 3.50-3.40 (m, 1H), 3.05-2.85 (m, 6H), 2.33 (s, 3H), 2.26 (s, 2H), 2.22 (s, 6H), 1.54 (t, J=7.0 Hz, 2H), 1.40-1.18 (m, 4H), 0.82 (t, J=7.6 Hz, 6H).

Example 431

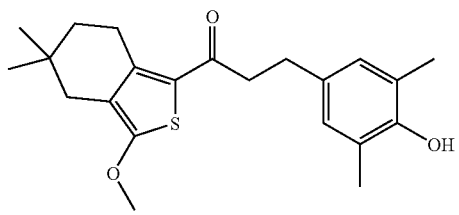

Hydrogenation of Example 126 following the procedure given in Example 23 affords 3-(4-hydroxy-3,5-dimethyl-phenyl)-1-(3-methoxy-5,5-dimethyl-4,5,6,7-tetrahydro-benzo[c]thiophen-1-yl)-propan-1-one; LC-MS: t$_R$=1.12 min, [M+1]$^+$=373.29.

Examples 432 to 434

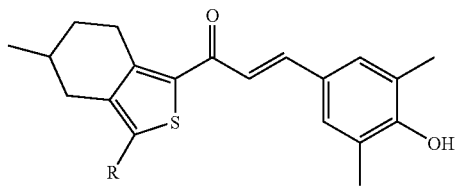

The following examples are prepared by condensing either Example AA, AC or AE with 4-hydroxy-3,5-dimethylbenzaldehyde in analogy to the procedure described in Example 22:

| | | starting from | LC-MS | |
|---|---|---|---|---|
| Example | R | Example | t$_R$ (min) | [M + H]$^+$ |
| 432 | H | AA | 1.12 | 327.26 |
| 433 | CH$_3$ | AC | 1.15 | 341.28 |
| 434 | CH$_2$CH$_3$ | AE | 1.17 | 355.29 |

Examples 435 to 437

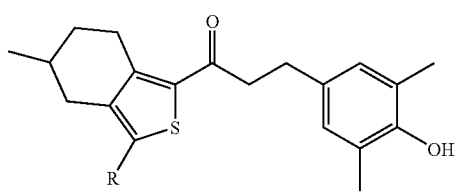

The following examples are prepared by hydrogenation of previous examples following the procedure given in Example 23:

| | | starting from | LC-MS | |
|---|---|---|---|---|
| Example | R | Example | t$_R$ (min) | [M + H]$^+$ |
| 435 | H | 432 | 1.10 | 329.30 |
| 436 | CH$_3$ | 433 | 1.13 | 343.29 |
| 437 | CH$_2$CH$_3$ | 434 | 1.15 | 357.34 |

Examples 438 to 440

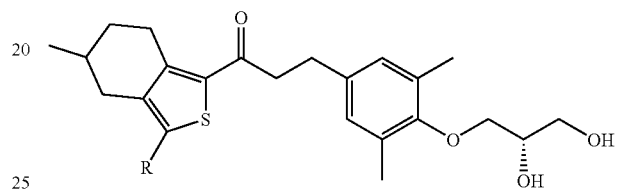

The following examples are prepared by alkylation of the previous examples following the procedure given in Example 27:

| | | starting from | LC-MS | |
|---|---|---|---|---|
| Example | R | Example | t$_R$ (min) | [M + H]$^+$ |
| 438 | H | 435 | 1.02 | 403.33 |
| 439 | CH$_3$ | 436 | 1.04 | 417.33 |
| 440 | CH$_2$CH$_3$ | 437 | 1.07 | 431.40 |

Example 438

$^1$H NMR (CD$_3$OD): δ 7.25 (s, 1H9, 6.85 (s, 2H), 4.00-3.92 (m, 1H), 3.82-3.61 (m, 4H), 3.25 (ddd, J=2.9, 5.3, 18.8 Hz, 1H), 3.09-3.03 (m, 2H), 2.90-2.75 (m, 4H), 2.30-2.20 (m, 7H), 1.92-1.70 (m, 2H), 1.40-1.26 (m, 1H), 1.05 (d, J=6.4 Hz, 3H).

Example 441

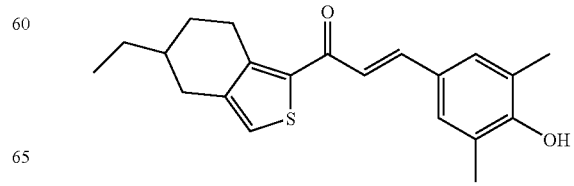

1-(5-Ethyl-4,5,6,7-tetrahydro-benzo[c]thiophen-1-yl)-3-(4-hydroxy-3,5-dimethyl-phenyl)-propenone is prepared by condensing Example AG with 4-hydroxy-3,5-dimethylbenzaldehyde in analogy to the procedure described in Example 22; LC-MS: $t_R$=1.15 min, $[M+1]^+$=341.24.

Example 442

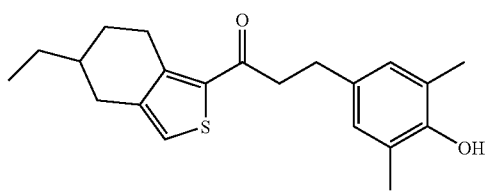

1-(5-Ethyl-4,5,6,7-tetrahydro-benzo[c]thiophen-1-yl)-3-(4-hydroxy-3,5-dimethyl-phenyl)-propan-1-one is prepared by hydrogenation of Example 441 following the procedure given in Example 23; LC-MS: $t_R$=1.14 min, $[M+1]^+$=343.27.

Example 443

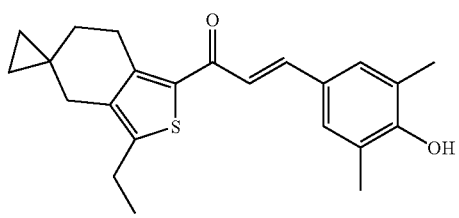

3-[4-((S)-2,3-Dihydroxy-propoxy)-3,5-dimethyl-phenyl]-1-(5-ethyl-4,5,6,7-tetrahydro-benzo[c]thiophen-1-yl)-propan-1-one is prepared by alkylation of Example 442 with (S)-3-chloro-propane-1,2-diol following the procedure given in Example 27; LC-MS: $t_R$=1.05 min, $[M+1]^+$=417.39.

Example 444

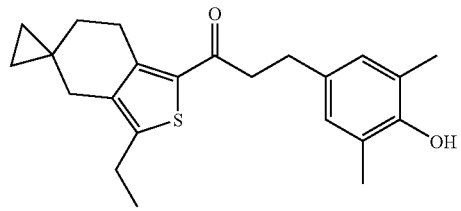

1-(3-Ethyl-5,5-ethylene-4,5,6,7-tetrahydro-benzo[c]thiophen-1-yl)-3-(4-hydroxy-3,5-dimethyl-phenyl)-propenone is prepared by condensing Example AJ with 4-hydroxy-3,5-dimethylbenzaldehyde in analogy to the procedure described in Example 22; LC-MS: $t_R$=1.16 min, $[M+1]^+$=367.29.

Example 445

1-(3-Ethyl-5,5-ethylene-4,5,6,7-tetrahydro-benzo[c]thiophen-1-yl)-3-(4-hydroxy-3,5-dimethyl-phenyl)-propanone is prepared by hydrogenation of Example 444 following the procedure given in Example 23; LC-MS: $t_R$=1.15 min, $[M+1]^+$=369.33.

Examples 446 to 454

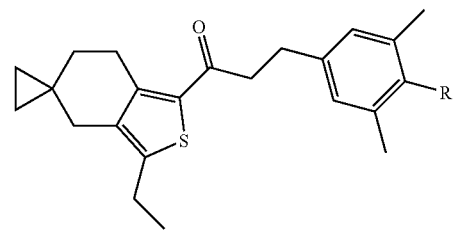

The following examples are prepared in analogy to previous examples starting from Example 445

| Example | R | prepared in analogy to Example | LC-MS $t_R$ (min) | $[M+H]^+$ |
|---|---|---|---|---|
| 446 | ～O～OH | 24 | 1.13 | 413.29 |
| 447 | ～O～OH (Me) | 25 | 1.16 | 427.39 |
| 448 | ～O～～OH | 26 | 1.15 | 427.41 |
| 449 | ～O～(OH)～OH | 27 | 1.06 | 443.41 |

-continued

| Example | R | prepared in analogy to Example | LC-MS $t_R$ (min) | [M + H]$^+$ |
|---|---|---|---|---|
| 450 | | 28 | 1.07 | 443.39 |
| 451 | | 29 | 1.15 | 457.46 |
| 452 | | 30 | 0.97 | 440.45 |
| 453 | | 31 | 1.00 | 466.35 |
| 454 | | 32 | 0.97 | 482.41 |

Examples 455 to 458

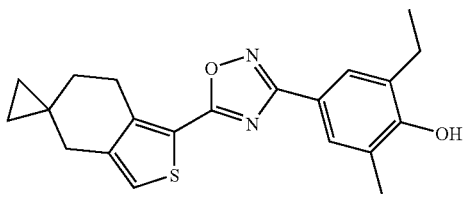

The following Examples are prepared in analogy to previous examples using Example AH and Hydroxyamidine 1:

| Example | R | prepared in analogy to Example | LC-MS $t_R$ (min) | [M + H]$^+$ |
|---|---|---|---|---|
| 455 | OH | 127 | 1.16 | 353.19 |
| 456 | | 128 | 0.91 | 467.41 |
| 457 | | 129 | 1.02 | 484.41 |
| 458 | | 130 | 1.01 | 498.33 |

Example 455

$^1$H NMR (D$_6$-DMSO): δ 8.94 (s, 1H), 7.63 8 s, 2H), 7.59 (s, 1H), 3.15 (t, J=6.4 Hz, 2H), 2.61 (s, 2H), 2.25 (s, 6H), 1.64 (t, J=6.4 Hz, 2H), 0.48-0.36 (m, 4H).

Example 459

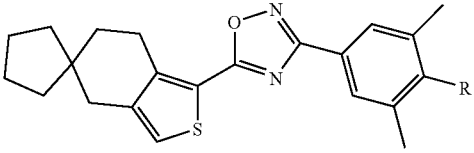

4-[5-(5,5-Ethylene-4,5,6,7-tetrahydro-benzo[c]thiophen-1-yl)-[1,2,4]oxadiazol-3-yl]-2-ethyl-6-methyl-phenol is prepared from Example AH and Hydroxyamidine 2 in analogy to Example 127; LC-MS: $t_R$=1.18 min, [M+1]$^+$=367.35.

Examples 460 to 463

The following Examples are prepared in analogy to previous examples using Example AK and Hydroxyamidine 1:

| Example | R | prepared in analogy to Example | LC-MS $t_R$ (min) | $[M + H]^+$ |
|---|---|---|---|---|
| 460 | OH | 127 | 1.21 | 381.29 |
| 461 | -CH2-NH2) | 128 | 0.95 | 454.40 |
| 462 | -CH2-NH-CO-CH2-OH) | 129 | 1.09 | 512.43 |
| 463 | -CH2-NH-CO-CH2CH2-OH) | 130 | 1.07 | 526.43 |

Examples 464 to 467

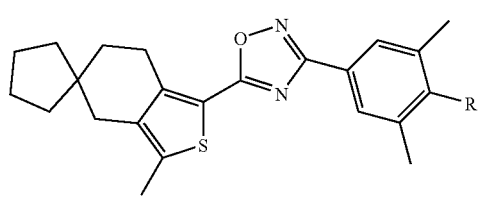

The following Examples are prepared in analogy to previous examples using Example AL and Hydroxyamidine 1:

| Example | R | prepared in analogy to Example | LC-MS $t_R$ (min) | $[M + H]^+$ |
|---|---|---|---|---|
| 464 | OH | 127 | 1.24 | 395.25 |
| 465 | -CH2-NH2) | 128 | 0.97 | 468.46 |
| 466 | -CH2-NH-CO-CH2-OH) | 129 | 1.12 | 526.45 |
| 467 | -CH2-NH-CO-CH2CH2-OH) | 130 | 1.11 | 540.53 |

Examples 468 to 471

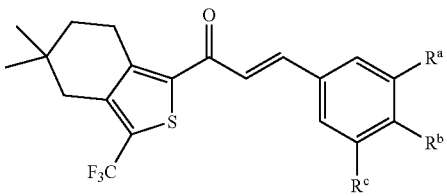

The following examples are prepared by condensing Example AM with the appropriate Aldehydes under acidic conditions as described for Example 22 or with Aldehyde 11 under basic conditions as described for Intermediate 2:

| Example | Aldehyde used | $R^a$ | $R^b$ | $R^c$ | LC-MS $t_R$ (min) | $[M+H]^+$ |
|---|---|---|---|---|---|---|
| 468 | 4-hydroxy-3,5-dimethylbenzaldehyde | $CH_3$ | OH | $CH_3$ | 1.22 | 409.32 |
| 469 | 1 | $CH_3$ | OH | $CH_2CH_3$ | 1.23 | 423.36 |
| 470 | 2 | $CH_2CH_3$ | OH | $CH_2CH_3$ | 1.24 | 437.27 |
| 471 | 11 | $CH_3$ | $NH_2$ | $CH_3$ | 1.21 | 408.17 |

Examples 472 to 475

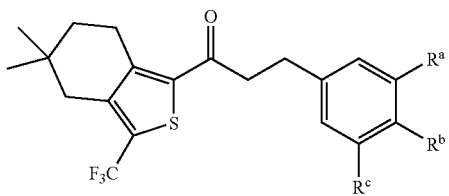

The following examples are prepared by hydrogenation of previous examples following the procedure given in Example 23;

| Example | prepared from example | $R^a$ | $R^b$ | $R^c$ | LC-MS $t_R$ (min) | $[M+H]^+$ |
|---|---|---|---|---|---|---|
| 472 | 468 | $CH_3$ | OH | $CH_3$ | 1.18 | 411.36 |
| 473 | 469 | $CH_3$ | OH | $CH_2CH_3$ | 1.20 | 425.29 |
| 474 | 470 | $CH_2CH_3$ | OH | $CH_2CH_3$ | 1.21 | 439.25 |
| 475 | 471 | $CH_3$ | $NH_2$ | $CH_3$ | 1.03 | 410.21 |

Example 472

$^{19}F$ NMR ($CDCl_3$): δ-133.8.

Examples 476 and 477

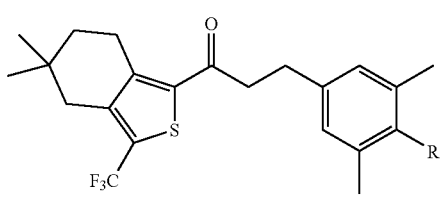

The following examples are prepared in analogy to previous examples starting from Example 472:

| Example | R | prepared in analogy to Example | LC-MS $t_R$ (min) | $[M+H]^+$ |
|---|---|---|---|---|
| 476 | 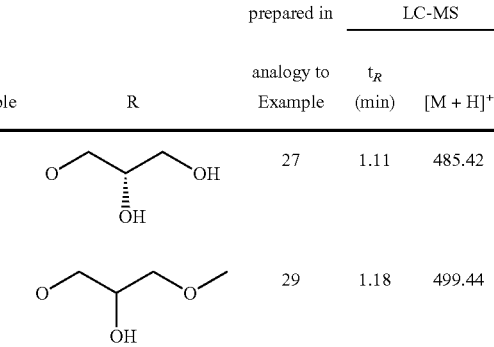 | 27 | 1.11 | 485.42 |
| 477 | | 29 | 1.18 | 499.44 |

Examples 478 to 493
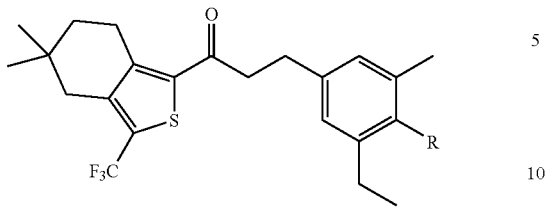
The following examples are prepared in analogy to previous examples starting from Example 473:
| Example | R | prepared in analogy to Example | $t_R$ (min) | [M + H]$^+$ |
|---|---|---|---|---|
| 478 | O-CH2-CH2-OH | 24 | 1.19 | 469.25 |
| 479 | O-CH2-CH(OH)-CH3 | 25 | 1.21 | 483.34 |
| 480 | O-CH2-CH2-CH2-OH | 26 | 1.21 | 483.33 |
| 481 | O-CH2-CH(OH)-CH2-OH (S) | 27 | 1.14 | 499.39 |
| 482 | O-CH2-CH(OH)-CH2-OH (R) | 28 | 1.12 | 499.28 |
| 483 | O-CH2-CH(OH)-CH2-O-CH3 | 29 | 1.21 | 513.39 |
| 484 | O-CH2-CH2-N(CH3)2 | 30 | 1.02 | 496.42 |
| 485 | O-CH2-CH2-pyrrolidine | 31 | 1.04 | 522.36 |
| 486 | O-CH2-CH2-morpholine | 32 | 1.03 | 538.36 |
| 487 | O-CH2-CH(OH)-CH2-NH2 | 128 | 0.96 | 498.36 |
| 488 | O-CH2-CH(OH)-CH2-NH-C(O)-CH2-OH | 129 | 1.09 | 556.40 |

| Example | R | prepared in analogy to Example | LC-MS $t_R$ (min) | $[M + H]^+$ |
|---|---|---|---|---|
| 489 | ![structure] | 130 | 1.08 | 570.31 |
| 490 | ![structure] | 238 | 0.95 | 555.39 |
| 491 | ![structure] | 238 | 0.96 | 569.46 |
| 492 | ![structure] | 238 | 0.95 | 569.41 |
| 493 | ![structure] | 238 | 0.96 | 583.41 |

Example 482

$^1$H NMR (CDCl$_3$): δ 6.91-6.86 (m, 2H), 4.11-4.05 (m, 1H), 3.87-3.75 (m, 4H), 3.14-3.02 (m, 4H), 2.98-2.92 (m, 2H), 2.63 (q, J=7.6 Hz, 2H), 2.56 (d, J=1.2 Hz, 2H), 2.26 (s, 3H), 1.57 (t, J=6.4 Hz, 2H), 1.21 (t, J=7.6 Hz, 3H), 0.98 (s, 6H).

Examples 494 to 500

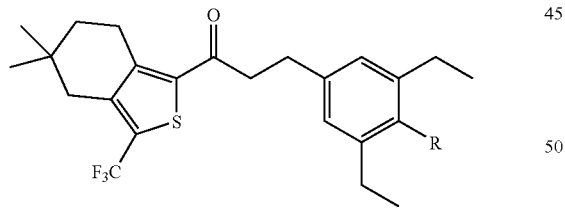

The following examples are prepared in analogy to previous examples starting from Example 474:

| Example | R | prepared in analogy to Example | LC-MS $t_R$ (min) | $[M + H]^+$ |
|---|---|---|---|---|
| 494 | ![structure] | 128 | 0.97 | 512.08 |

-continued

| Example | R | prepared in analogy to Example | LC-MS $t_R$ (min) | [M + H]$^+$ |
|---|---|---|---|---|
| 495 | (3-hydroxy-2-hydroxypropyl)-NH-C(O)-CH2-OH | 129 | 1.11 | 570.50 |
| 496 | (3-hydroxy-2-hydroxypropyl)-NH-C(O)-CH2CH2-OH | 130 | 1.10 | 584.31 |
| 497 | (3-hydroxy-2-hydroxypropyl)-NH-C(O)-CH2-NH2 | 238 | 0.96 | 569.38 |
| 498 | (3-hydroxy-2-hydroxypropyl)-NH-C(O)-CH2-NHCH3 | 238 | 0.97 | 583.33 |
| 499 | (3-hydroxy-2-hydroxypropyl)-NH-C(O)-CH2CH2-NH2 | 238 | 0.96 | 583.37 |
| 500 | (3-hydroxy-2-hydroxypropyl)-NH-C(O)-CH2CH2-NHCH3 | 238 | 0.97 | 597.45 |

Example 501

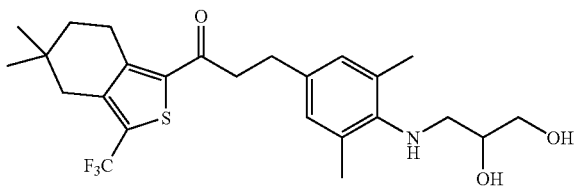

3-[4-(2,3-Dihydroxy-propylamino)-3,5-dimethyl-phenyl]-1-(5,5-dimethyl-3-trifluoromethyl-4,5,6,7-tetrahydro-benzo[c]thiophen-1-yl)-propan-1-one is prepared in analogy to Example 364 starting from Example 475; LC-MS: $t_R$=0.92 min, [M+1]$^+$=484.32.

Examples 502 to 505

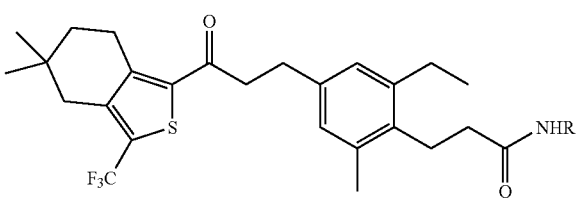

The following examples are prepared in analogy to Example 322 using Intermediate 7:

| Example | R | LC-MS $t_R$ (min) | [M + H]$^+$ |
|---|---|---|---|
| 502 | ![](OH, OH branched) | 1.09 | 554.30 |
| 503 | ![](OH, HO branched) | 1.08 | 554.33 |
| 504 | CH$_2$COOCH$_3$ | 1.18 | 552.37 |
| 505 | CH$_2$COOH | 1.12 | 538.86 |

Example 506

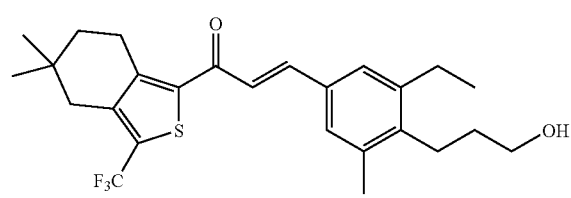

1-(5,5-Dimethyl-3-trifluoromethyl-4,5,6,7-tetrahydro-benzo[c]thiophen-1-yl)-3-[3-ethyl-4-(3-hydroxy-propyl)-5-methyl-phenyl]-propenone is prepared in analogy to Example 15 by condensing Example AM and Aldehyde 8; LC-MS: $t_R$=1.23 min, [M+1]$^+$=465.24.

Example 507

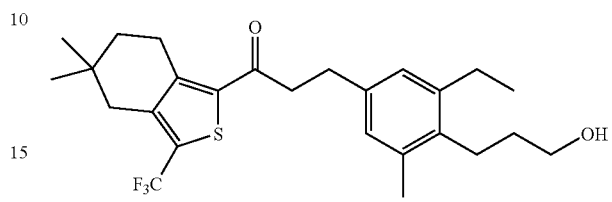

In analogy to Example 16, hydrogenation of Example 506 affords 1-(5,5-dimethyl-3-trifluoromethyl-4,5,6,7-tetrahydro-benzo[c]thiophen-1-yl)-3-[3-ethyl-4-(3-hydroxy-propyl)-5-methyl-phenyl]-propan-1-one; LC-MS: $t_R$=1.20 min, [M+1]$^+$=467.42.

Example 508

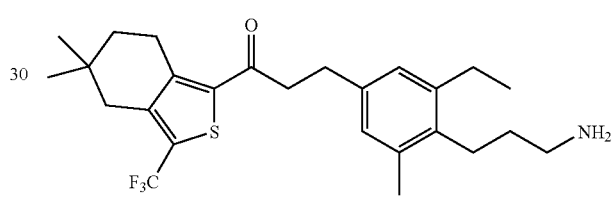

3-[4-(3-Amino-propyl)-3-ethyl-5-methyl-phenyl]-1-(5,5-dimethyl-3-trifluoromethyl-4,5,6,7-tetrahydro-benzo[c]thiophen-1-yl)-propan-1-one is prepared from Example 507 in analogy to Example 338; LC-MS: $t_R$=1.00 min, [M+1]$^+$=466.25.

Examples 509 to 514

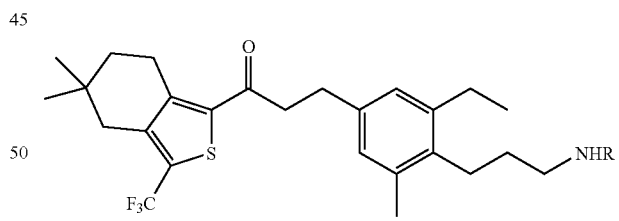

| Example | R | prepared in analogy to Example | LC-MS $t_R$ (min) | [M + H]$^+$ |
|---|---|---|---|---|
| 509 | COCH$_2$OH | 231 | 1.16 | 524.29 |
| 510 | COCH$_2$CH$_2$OH | 231 | 1.15 | 538.40 |
| 511 | COCH$_2$NH$_2$ | 238 | 0.99 | 523.45 |
| 512 | COCH$_2$NHCH$_3$ | 238 | 1.01 | 537.48 |
| 513 | COCH$_2$CH$_2$NH$_2$ | 238 | 0.99 | 537.45 |
| 514 | COCH$_2$CH$_2$NHCH$_3$ | 238 | 1.01 | 551.47 |

Examples 515 to 523

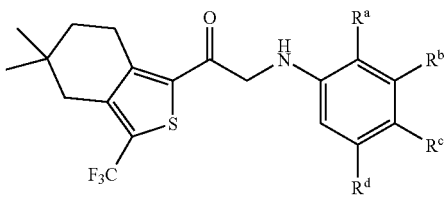

The following examples are prepared in analogy to Example 155 starting from Bromoketone 3 and the appropriate anilines:

| Example | $R^a$ | $R^b$ | $R^c$ | $R^d$ | $t_R$ (min) | LC-MS $[M+H]^+$ |
|---|---|---|---|---|---|---|
| 515 | H | H | H | H | 1.16 | 368.22 |
| 516 | CH$_3$ | H | H | H | 1.19 | 382.33 |
| 517 | H | CH$_3$ | H | CH$_3$ | 1.19 | 396.19 |
| 518 | OCH$_3$ | H | H | H | 1.18 | 398.29 |
| 519 | H | H | OCH$_3$ | H | 1.12 | 398.26 |
| 520 | CH$_3$ | H | OCH$_3$ | H | 1.17 | 412.29 |
| 521 | H | CF$_3$ | OCH$_3$ | H | 1.19 | 466.07 |
| 522 | CH$_3$ | H | H | OCH$_3$ | 1.18 | 412.31 |
| 523 | H | H | ⋯CH₂CH₂OH | H | 1.08 | 412.17 |

Example 524

GTPγS Assay to Determine EC$_{50}$ Values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 µM GDP (Sigma, G-7127), 2.5% DMSO (Fluka, 41644), 50 pM $^{35}$S-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of $^{35}$S-GTPγS. After addition of 50 µl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 µl MicroScint20 (Packard Biosciences, order #6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay.

Table 1 shows the EC$_{50}$ value of some compounds of the present invention. The EC$_{50}$ values were determined according to the method described above.

TABLE 1

| Compound of Example | EC$_{50}$ [nM] | Compound of Example | EC$_{50}$ [nM] |
|---|---|---|---|
| 27 | 2.4 | 269 | 1.8 |
| 41 | 2.8 | 271 | 1.7 |
| 62 | 5.9 | 296 | 1.0 |
| 66 | 2.5 | 312 | 0.8 |
| 71 | 5.9 | 339 | 1.8 |
| 77 | 1.8 | 351 | 3.4 |
| 79 | 3.7 | 356 | 8.0 |
| 80 | 0.6 | 378 | 6.1 |
| 114 | 4.1 | 414 | 4.2 |
| 129 | 3.8 | 423 | 7.6 |
| 149 | 5.1 | 457 | 6.2 |
| 210 | 1.1 | 501 | 2.6 |
| 230 | 2.9 | 489 | 2.9 |
| 247 | 3.1 | 517 | 9.7 |

Example 525

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of some compounds of the present invention to normotensive male Wistar rats as compared to a group of animals treated with vehicle only.

TABLE 2

| Compound of Example | Lymphocyte counts |
|---|---|
| 69 | −63% |
| 70 | −51% |
| 240 | −66% |
| 295 | −64% |
| 330 | −56% |
| 367 | −78% |

The invention claimed is:
1. A compound Formula (I)

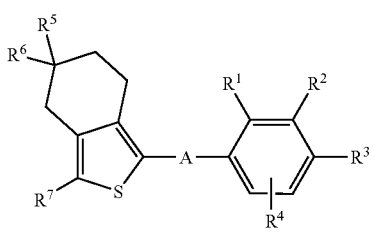

Formula (I)

wherein
A represents

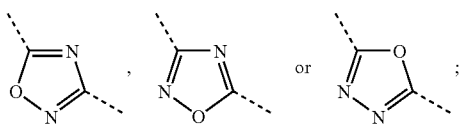

R¹ represents hydrogen, $C_{1-5}$-alkyl, $C_{1-5}$-alkoxy, or halogen;
R² represents hydrogen, $C_{1-5}$-alkyl, $C_{1-5}$-alkoxy, trifluoromethyl, trifluoromethoxy or halogen;
R³ represents hydrogen, hydroxy-$C_{1-5}$-alkyl, 2,3-dihydroxypropyl, di-(hydroxy-$C_{1-5}$-alkyl)-$C_{1-5}$-alkyl, —$CH_2$—$(CH_2)_k$—$NR^{31}R^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid, $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid, $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid, $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —$CH_2$—$(CH_2)_n$—$CONR^{31}R^{32}$, —CO—$NHR^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —$(CH_2)_n$CH(OH)—$CH_2$—$NR^{31}R^{32}$, hydroxy, $C_{1-5}$-alkoxy, fluoro-$C_{1-5}$-alkoxy, hydroxy-$C_{2-5}$-alkoxy, di-(hydroxy-$C_{1-5}$-alkyl)-$C_{1-5}$-alkoxy, 1-glyceryl, 2-glyceryl, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid, $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-($C_{1-5}$-alkylcarbamoyl)propoxy, 3-(2-hydroxyethylcarbamoyl)propoxy, —$OCH_2$—CH(OH)—$CH_2$—$NR^{31}R^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)_k$—$NHCOR^{34}$, —$(CH_2)_n$CH(OH)—$CH_2$—$NHCOR^{34}$, —$OCH_2$—$(CH_2)_m$—$NHCOR^{34}$, —$OCH_2$—CH(OH)—$CH_2$—$NHCOR^{34}$, or —$SO_2NHR^-$;
$R^{31}$ represents hydrogen, methyl, ethyl, 1-propyl, 2-propyl, 2-hydroxyethyl, 2-hydroxy-1-hydroxymethyl-ethyl, 2,3-dihydroxypropyl, 2-$C_{1-5}$-alkoxyethyl, 3-hydroxypropyl, 3-$C_{1-5}$-alkoxypropyl, 2-aminoethyl, 2-($C_{1-5}$-alkylamino)ethyl, 2-(di-($C_{1-5}$-alkyl)amino) ethyl, carboxymethyl, $C_{1-5}$-alkylcarboxymethyl, 2-carboxyethyl, or 2-($C_{1-5}$-alkylcarboxy)ethyl;
$R^{32}$ represents hydrogen, methyl, or ethyl;
$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;
$R^{34}$ represents hydroxymethyl, hydroxyethyl, aminomethyl, methylaminomethyl, dimethylaminomethyl, aminoethyl, 2-methylamino-ethyl, or 2-dimethylaminoethyl;
k represents the integer 1, 2, or 3;
m represents the integer 1 or 2;
n represents 0, 1, or 2;
$R^4$ represents hydrogen, $C_{1-5}$-alkyl or halogen;
$R^5$ represents methyl or ethyl;
$R^6$ represents methyl or ethyl;

or $R^5$ and $R^6$ together form a carbocyclic 3-, 4-, or 5-membered ring; and $R^7$ represents hydrogen, methyl, ethyl, n-propyl, isopropyl, trifluoromethyl, hydroxymethyl, methoxymethyl, methoxy, methylthio, hydroxycarbonyl, aminocarbonyl, mono- or di-($C_{1-5}$-alkyl)aminocarbonyl, amino, mono- or di-($C_{1-5}$-alkyl)amino, in free form or in an optically pure enantiomer, a mixture of enantiomers, a diastereomer, a mixture of diastereomers, a diastereomeric racemate, a mixtures of diastereomeric racemates, or a salt form.

2. The compound according to claim 1, wherein A represents

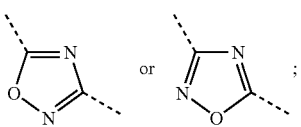

$R^3$ represents hydrogen, hydroxy-$C_{1-5}$-alkyl, 2,3-dihydroxypropyl, di-(hydroxy-$C_{1-5}$-alkyl)-$C_{1-5}$alkyl, —$CH_2$—$(CH_2)_k$—$NR^{31}R^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —$CH_2$—$(CH_2)_n$—$CONR^{31}R^{32}$, —CO—$NHR^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —$(CH_2)_n$CH(OH)—$CH_2$—$NR^{31}R^{32}$, hydroxy, $C_{1-5}$-alkoxy, fluoro-$C_{1-5}$-alkoxy, hydroxy-$C_{2-5}$-alkoxy, di-(hydroxy-$C_{1-5}$-alkyl)—$C_{1-5}$-alkoxy, 1-glyceryl, 2-glyceryl, 2-hydroxy-3-methoxypropoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-($C_{1-5}$-alkylcarbamoyl)propoxy, 3-(2-hydroxyethylcarbamoyl)propoxy, —$OCH_2$—CH(OH)—$CH_2$—$NR^{31}R^{32}$, 3-[(azetidine-3-carboxylic acid)-]-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)$—NHCOR$^{34}$, —$(CH_2)_n$CH(OH)—$CH_2$—NHCOR$^{34}$, —$OCH_2$—$(CH_2)_m$—NHCOR$^{34}$, or —$OCH_2$—CH(OH)—$CH_2$—NHCOR$^{34}$; and $R^{31}$ represents hydrogen, methyl, ethyl, 1-propyl, 2-propyl, 2-hydroxyethyl, 2-hydroxy-1-hydroxymethyl-ethyl, 2-$C_{1-5}$-alkoxyethyl, 3-hydroxypropyl, 3-$C_{1-5}$-alkoxypropyl, 2-aminoethyl, 2-($C_{1-5}$-alkylamino)ethyl, 2-(di-($C_{1-5}$-alkyl)amino)ethyl, carboxymethyl, $C_{1-5}$-alkylcarboxymethyl, 2-carboxyethyl, or 2-($C_{1-5}$-alkylcarboxy)ethyl;

and wherein k, m, n, $R^{32}$, $R^{33}$ and $R^{34}$ are as defined in claim 1.

3. The compound according to claim 1, wherein A represents

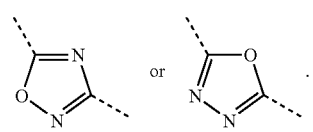

4. The compound according to claim 1, wherein $R^1$ and $R^4$ represent hydrogen and $R^2$ represents a methyl group.

5. The compound according to claim 1, wherein $R^1$ represents hydrogen, $R^2$ and $R^4$ represent a methyl group, and $R^4$ is in the ortho-position with respect to $R^3$.

6. The compound according to claim 1, wherein $R^1$ represents hydrogen, $R^2$ represents a methyl group, and $R^4$ represents an ethyl group in the ortho-position with respect to $R^3$.

7. The compound according to claim 1, wherein $R^1$ represents hydrogen, $R^2$ represents a methyl group, and $R^4$ represents chloro in the ortho-position with respect to $R^3$.

8. The compound according to claim 1, wherein $R^1$ and $R^4$ represent hydrogen and $R^2$ represents chloro.

9. The compound according to claim 1, wherein $R^1$ represents hydrogen, $R^2$ represents a methoxy group, and $R^4$ represents chloro or fluoro both in the ortho-position with respect to $R^3$.

10. The compound according to claim 1, wherein $R^1$ represents a methoxy group and $R^2$ and $R^4$ represent hydrogen.

11. The compound according to claim 1, wherein $R^3$ represents hydroxy-$C_{1-5}$-alkyl, 2,3-dihydroxypropyl, di-(hydroxy-$C_{1-5}$-alkyl)—$C_{1-5}$-alkyl, —$CH_2$—$(CH_2)_k$—$NR^{31}R^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid, $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid, $C_{1-5}$-alkylester)-1-yl]-ethyl, 3-[(pyrrolidine-3-carboxylic acid)-1-yl]-propyl, 3-[(pyrrolidine-3-carboxylic acid, $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —$CH_2$—$(CH_2)_n$—$CONR^-R^{32}$, —$CO$—$NHR^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, or —$(CH_2)_2CH(OH)$—$CH_2$—$NR^{31}R^{32}$, and wherein k, n, $R^{31}$ and $R^{32}$ are as defined in claim 1.

12. The compound according to claim 1, wherein $R^3$ represents hydroxy-$C_{1-5}$-alkyl, 2,3-dihydroxypropyl, di-(hydroxy-$C_{1-5}$-alkyl)—$C_{1-5}$-alkyl, —$CH_2$—$(CH_2)_k$—$NR^{31}R^{32}$, (azetidine-3-carboxylic acid)-1-yl-methyl, 2-[(azetidine-3-carboxylic acid)-1-yl]-ethyl, 3-((azetidine-3-carboxylic acid)-1-yl]-propyl, (pyrrolidine-3-carboxylic acid)-1-yl-methyl, (pyrrolidine-2-carboxylic acid)-1-yl-methyl, 2-[(pyrrolidine-3-carboxylic acid)-1-yl]-ethyl, 2-[(pyrrolidine-2-carboxylic acid)-1-yl]-ethyl, 3-[(pyrrolidine-3-carboxylic acid)-1-yl]-propyl, 3-[(pyrrolidine-2-carboxylic acid)-1-yl]-propyl, —$CO$—$NHR^{31}$, or —$(CH_2)_nCH(OH)$—$CH_2$—$NR^{31}R^{32}$, wherein $R^{31}$ represents hydrogen, methyl, 2-hydroxyethyl, 2-hydroxy-1-hydroxymethyl-ethyl, or 2-aminoethyl, $R^{32}$ represents hydrogen, and k and n are as defined in claim 1.

13. The compound according to claim 1, wherein $R^3$ represents hydroxy, hydroxy-$C_{2-5}$-alkoxy, di-(hydroxy-$C_{1-5}$-alkyl)—$C_{1-5}$-alkoxy, 1-glyceryl, 2-glyceryl, 2-hydroxy-3-methoxy-propoxy, —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl-propoxy, 2-morpholin-4-yl-ethoxy, 3-morpholin-4-yl-propoxy, 2-[(azetidine-3-carboxylic acid)-1-yl]-ethoxy, 2-((azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-((pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid, 5-alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —$O$—$CH_2$—$CONR^{31}R^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-($C_{1-5}$-alkylcarbamoyl)propoxy, 3-(2-hydroxyethylcarbamoyl)propoxy, —$OCH_2$—$CH(OH)$—$CH_2$—$NR^{31}R^{32}$, 3-[(azetidine-3-carboxylic acid)-1-yl 1-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, or 2-hydroxy-3-morpholin-4-yl-propoxy, and wherein m, $R^{31}$ and $R^{32}$ are as defined in claim 1.

14. The compound according to claim 1, wherein $R^3$ represents hydroxy, hydroxy-$C_{2-5}$-alkoxy, di-(hydroxy-$C_{1-5}$-alkyl)-$C_{1-5}$-alkoxy, 1-glyceryl, 2-glyceryl, 2-hydroxy-3-methoxy-propoxy, —$OCH_2$—$(CH_2)_m$—$NR^{31}R^{32}$, 2-[(azetidine-3-carboxylic acid)-1-yl]-ethoxy, 3-[(azetidine-3-carboxylic acid)-1-yl]-propoxy, —$O$—$CH_2$—$CONR^{32}$, $R^{32}$, 1-(1-(3-carboxy-azetidinyl))-1-oxo-2-ethoxy, 3-carbamoyl-propoxy, 3-($C_{1-5}$-alkylcarbamoyl)propoxy, 3-(2-hydroxyethylcarbamoyl)propoxy, —$OCH_2$—$CH(OH)$—$CH_2$—$NR^{31}R^{32}$, 3-[(azetidine-3-carboxylic acid)-1-yl]-2-hydroxypropoxy, 2-hydroxy-3-[(pyrrolidine-3-carboxylic acid)-1-yl]-propoxy, or 2-hydroxy-3-[(pyrrolidine-2-carboxylic acid)-1-yl]-propoxy, wherein $R^{31}$ represents hydrogen, methyl, 2-hydroxyethyl, 2-hydroxy-1-hydroxymethyl-ethyl, 2-aminoethyl, or 2-carboxyethyl, $R^{32}$ represents hydrogen, and wherein m is as defined in claim 1.

15. The compound according to claim 1, wherein $R^3$ represents —$CH$, —$(CH_2)_k$—$NHSO_2R^{33}$, —$(CH_2)_nCH(OH)$—$CH_2$—$NHSO_2R^{33}$, —$OCH_2$—$(CH_2)_m$—$NHSO_2R^{33}$, —$OCH_2$—$CH(OH)$—$CH_2$—$NHSO_2R^{33}$, —$CH_2$—$(CH_2)_k$—$NHCOR^{34}$, —$(CH_2)_nCH(OH)$—$CH_2$—$NHCOR^{34}$, —$OCH_2$—$(CH_2)_m NHCOR^{34}$, or —$OCH_2$—$CH(OH)$—$CH_2$—$NHCOR^{34}$ and wherein k, m, n, $R^{33}$ and $R^{34}$ are as defined in claim 1.

16. The compound according to claim 1, wherein $R^5$ and $R^6$ represent methyl, or together form a carbocyclic 3-, or 4-membered ring.

17. The compound according to claim 1, wherein $R^7$ represents methyl, ethyl, propyl or isopropyl.

18. The compound according to claim 1 selected from the group consisting of:

N-(3-{4-[5-(5,5-dimethyl-4,5,6,7-tetrahydro-benzo[c]thiophen-1-yl)-[1,2,4]oxadiazol-3-yl]-2,6-dimethyl-phenoxy}-2-hydroxy-propyl)-2-hydroxy-acetamide;

N-(3-{4-[5-(5,5-dimethyl-4,5,6,7-tetrahydro-benzo[c]thiophen-1-yl)-[1,2,4]oxadiazol-3-yl]-2-ethyl-6-methyl-phenoxy}-2-hydroxy-propyl)-2-hydroxy-acetamide;

N-(3-{4-[5-(5,5-dimethyl-4,5,6,7-tetrahydro-benzo[c]thiophen-1-yl)-[1,2,4]oxadiazol-3-yl]-2-ethyl-6-methyl-phenoxy}-2-hydroxy-propyl)-3-hydroxy-propionamide;

N-(3-{2-ethyl-6-methyl-4-[5-(3,5,5-trimethyl-4,5,6,7-tetrahydro-benzo[c]thiophen-1-yl)-[1,2,4]oxadiazol-3-yl]-phenoxy}-2-hydroxy-propyl)-2-hydroxy-acetamide;

N-(3-{4-[5-(3-ethyl-5,5-dimethyl-4,5,6,7-tetrahydro-benzo[c]thiopen-1-yl)-[1,2,4]oxadiazol-3-yl]-2,6-dimethyl-phenoxy}-2-hydroxy-propyl)-2-hydroxy-acetamide;

3-{2-ethyl-4-[5-(3-ethyl-5,5-dimethyl-4,5,6,7-tetrahydro-benzo[c]thiopen-1-yl) -[1,2,4]oxadiazol-3-yl]-6-methyl-phenyl}-N-(2-hydroxy-ethyl)-propionamide;

N-(3-{4-[5-(5,5-ethylene-4,5,6,7-tetrahydro-benzo[c]thiopen-1-yl)-[1,2,4]oxadiazol-3-yl]-2,6-dimethyl-phenoxy}-2-hydroxy-propyl)-2-hydroxy-acetamide.

19. A pharmaceutical composition comprising the compound according to claim 1 and a pharmaceutically acceptable carrier.

20. A method for treating a disease or disorder associated with an activated immune system, comprising administering to a patient in need thereof a pharmaceutically active amount of the compound of claim 1, wherein said disease or disorder is selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

* * * * *

UNITED STATES PATENT AND TRADEMARK OFFICE
CERTIFICATE OF CORRECTION

Page 1 of 1

PATENT NO. : 7,723,378 B2
APPLICATION NO. : 11/909429
DATED : May 25, 2010
INVENTOR(S) : Bolli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 34 days.

Signed and Sealed this
Fifteenth Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,723,378 B2  
APPLICATION NO. : 11/909429  
DATED : May 25, 2010  
INVENTOR(S) : Martin Bolli et al.

Page 1 of 1

It is certified that error appears in the above-identified patent and that said Letters Patent is hereby corrected as shown below:

Claim 1, column 146, line 44, replace "-$SO_2NHR$" with "-$SO_2NHR^{31}$";

Claim 1, column 147, line 10, replace "a mixtures" with "a mixture";

Claim 2, column 148, line 33, replace "-$CH_2$-($CH_2$-NH-" with "-$CH_2$-$(CH_2)_k$-NH-";

Claim 14, column 150, lines 34-35, replace "-O-$CH_2$-$CONR^{32}$, $R^{32}$" with "-O-$CH_2$-$CONR^{31}R^{32}$";

Claim 15, column 150, line 46, replace "-CH,-$(CH_2)_k$-$NHSO_2R^{33}$" with "-$CH_2$-$(CH_2)_k$-$NHSO_2R^{33}$";

Claim 18, column 151, line 15, replace "thyl-phenyl}-N-(2-hydroxy-ethyl)-propionamide;" with "thyl-phenyl}-N-(2-hydroxy-ethyl)-propionamide; and".

Signed and Sealed this  
Twelfth Day of April, 2011

David J. Kappos  
*Director of the United States Patent and Trademark Office*